United States Patent
Carrancio et al.

(10) Patent No.: US 10,245,258 B2
(45) Date of Patent: Apr. 2, 2019

(54) TREATMENT OF A HEMATOLOGIC MALIGNANCY WITH 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE

(71) Applicant: Celgene Corporation, Summit, NJ (US)

(72) Inventors: Soraya Carrancio, San Diego, CA (US); Paul Hollenbach, Castro Valley, CA (US); Antonia Lopez-Girona, San Diego, CA (US); Kyle MacBeth, San Francisco, CA (US); Michael Pourdehnad, San Francisco, CA (US); Irit Rappley, San Diego, CA (US); Gang Lu, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/614,434

(22) Filed: Jun. 5, 2017

(65) Prior Publication Data
US 2017/0348298 A1 Dec. 7, 2017

Related U.S. Application Data

(60) Provisional application No. 62/346,344, filed on Jun. 6, 2016.

(51) Int. Cl.
*A61K 31/454* (2006.01)
*A61K 9/19* (2006.01)
*A61K 9/00* (2006.01)

(52) U.S. Cl.
CPC .......... *A61K 31/454* (2013.01); *A61K 9/0019* (2013.01); *A61K 9/19* (2013.01)

(58) Field of Classification Search
CPC ................................ A61K 31/454; A61K 9/19
See application file for complete search history.

(56) References Cited

U.S. PATENT DOCUMENTS

| | | | |
|---|---|---|---|
| 9,499,514 B2 | 11/2016 | Hansen et al. | |
| 2004/0220144 A1 | 11/2004 | Zeldis | |
| 2009/0175869 A1 | 7/2009 | Holmlund et al. | |
| 2015/0157603 A1 | 6/2015 | Higgins et al. | |
| 2015/0216886 A1 | 8/2015 | MacBeth et al. | |
| 2017/0196847 A1 | 7/2017 | Hui et al. | |
| 2017/0197933 A1 | 7/2017 | Alexander et al. | |
| 2017/0197934 A1 | 7/2017 | Fernandez et al. | |
| 2017/0007590 A1 | 12/2017 | Cathers et al. | |

OTHER PUBLICATIONS

Barretina et al, "The Cancer Cell Line Encyclopedia enables predictive modelling of anticancer drug sensitivity," Nature, 483(7391):603-607 (2012).

Bennett et al., "Pharmacological profiles of acute myeloid leukemia treatments in patient samples by automated flow cytometry: a bridge to individualized medicine," Clin. Lymphoma Myeloma Leuk., 14(4):305-318 (2014).

Cheson et al., "Revised recommendations of the International Working Group for diagnosis, standardization of response criteria, treatment outcomes, and reporting standards for therapeutic trials in acute myeloid leukemia," J. Clin. Oncol., 21(24):4642-4649 (2003).

Foster, "Deuterium isotope effects in the metabolism of drugs and xenobiotics: implications for drug design," Adv. Drug Res., 14:1-40 (1985).

Gatlely et. al., "Deuterioglucose: alteration of biodistribution by an isotope effect," J. Nucl. Med., 27(3):388-394 (1986).

Gordon et al., "The metabolism of the abortifacient terpene, (R)-(+)-pulegone, to a proximate toxin, menthofuran," Drug Metab. Dispos., 15(5):589-594 (1987).

Hahn et al., "Subcutaneous 5-azacitidine treatment of naturally occurring canine urothelial carcinoma: a novel epigenetic approach to human urothelial carcinoma drug development," J. Urol., 187(1):302-309 (2012).

Koopman et al, "Annexin V for flow cytometric detection of phosphatidylserine expression on B cells undergoing apoptosis," Blood, 84(5):1415-1420 (1994).

Kushner et al., "Pharmacological uses and perspectives of heavy water and deuterated compounds," Can. J. Physiol. Pharmacol., 77:79-88 (1999).

Lijinsky et. al., "Dose-response studies in carcinogenesis by nitroso-n-methyl-n-(2-phenyl)ethylamine in rats and the effects of deuterium substitution," Fd. Chem. Toxic., 20:393-399 (1982).

Lijinsky et. al., "Dose-response studies with tnitrosoheptamethyleneimine and its α-deuterium-labeled derivative in F344 rats," J. Nat. Cancer Inst., 69(5):1127-1133 (1982).

Lowenberg, "Acute myeloid leukemia: the challenge of capturing disease variety," Hematology ASH Education Program, 2008(1):1-11 (2008).

Mangold et. al., "Effects of deuterium labeling on azido amino acid mutagenicity in *Salmonella typhimurium*," Mutation Res., 308:33-42 (1994).

Pfeifer, et al, "Simian virus 40 large tumor antigen-immortalized normal human liver epithelial cells express hepatocyte characteristics and metabolize chemical carcinogens," Proc. Natl. Acad. Sci. USA, 90(11):5123-5127 (1993).

Rajkumar et al., "Decade in review-haematological cancer: advances in biology and therapy," Nat. Rev. Clin. Oncol., 11:628-630 (2014).

Ritz et al., "Bioassay analysis using R," J. Statist. Software, 12(5):1-22 (2005).

Simon et al., "Accelerated titration designs for phase I clinical trials in oncology," J. Natl. Cancer Inst., 89(15):1138-1147 (1997).

Van Dongen et al, "EuroFlow: Resetting leukemia and lymphoma immunophenotyping. Basis for companion diagnostics and personalized medicine," Leukemia, 26(9):1899-1907 (2012).

(Continued)

*Primary Examiner* — Sahar Javanmard
(74) *Attorney, Agent, or Firm* — Jones Day

(57) ABSTRACT

Provided herein are methods of treating, preventing, managing, and/or ameliorating leukemia or myelodysplastic syndrome comprising administering 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, an isotopologue, pharmaceutically acceptable salt, tautomer, solvate, hydrate, co-crystal, clathrate, or polymorph thereof to a patient.

43 Claims, 36 Drawing Sheets

(56) References Cited

OTHER PUBLICATIONS

Van Dongen et al., "EuroFlow antibody panels for standardized n-dimensional flow cytometric immunophenotyping of normal, reactive and malignant leukocytes," Leukemia (9):1908-1975 (2012).
Wade, "Deuterium isotope effects on noncovalent interactions between molecules," Chem. Biol. Interact., 117(3):191-217 (1999).
Zello et. al., "Plasma and urine enrichments following infusion of L-[1-13C]phenylalanine and L-[ring-2H5]phenylalanine in humans: evidence for an isotope effect in renal tubular reabsorption," Metabolism, 43:487-491 (1994).

| | Target % P/Po | Change In Mass (%)-ref Sorption | Desorption | Hysteresis |
|---|---|---|---|---|
| Cycle 1 | 0.0 | 0.000 | −0.270 | |
| | 10.0 | 0.093 | −0.120 | −0.213 |
| | 20.0 | 0.241 | 0.009 | −0.232 |
| | 30.0 | 0.439 | 0.112 | −0.327 |
| | 40.0 | 0.595 | 0.292 | −0.303 |
| | 50.0 | 0.700 | 0.456 | −0.244 |
| | 60.0 | 0.798 | 0.599 | −0.198 |
| | 70.0 | 0.903 | 0.748 | −0.154 |
| | 80.0 | 0.977 | 0.886 | −0.091 |
| | 90.0 | 1.085 | 1.085 | |

TREATMENT OF A HEMATOLOGIC MALIGNANCY WITH 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE

1. RELATED APPLICATIONS

This application claims the benefit of U.S. provisional application No. 62/346,344, filed Jun. 6, 2016, the disclosure of which is incorporated by reference in its entirety.

2. FIELD

Provided herein are methods of treating, preventing, managing, and/or ameliorating a hematologic malignancy with 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, an isotopologue, pharmaceutically acceptable salt, tautomer, solvate, hydrate, co-crystal, clathrate, or polymorph thereof. Further provided is a compound for use in methods of treating, preventing, managing, and/or ameliorating a hematologic malignancy, wherein the compound is 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, an isotopologue, pharmaceutically acceptable salt, tautomer, solvate, hydrate, co-crystal, clathrate, or polymorph thereof.

3. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in *Nature Reviews Clinical Oncology* 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

With respect to chemotherapy, there is a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Twelfth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

There is a need for safe and efficacious dosages and dosing regimens for administration of anti-cancer agents, including 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, an isotopologue, pharmaceutically acceptable salt, tautomer, solvate, hydrate, co-crystal, clathrate, or polymorph thereof for treatment of hematologic malignancies, such as leukemia, Hodgkin's and non-Hodgkin's lymphoma, multiple myeloma, and myelodysplastic syndrome (MDS).

4. BRIEF SUMMARY

In one embodiment, provided herein are methods of treating, preventing, managing, and/or ameliorating hematologic malignancies, for example leukemia, by administering to a subject 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, an isotopologue, pharmaceutically acceptable salt, tautomer, solvate, hydrate, co-crystal, clathrate, or polymorph thereof ("Compound 1"). In one embodiment, the leukemia is acute myeloid leukemia (AML). In one embodiment, the AML is relapsed or refractory AML. In one embodiment, provided herein is a method of treating of AML by administering to a subject a 2-(4-chlorophenyl)-N-((2-(2,6-dioxopiperidin-3-yl)-1-oxoisoindolin-5-yl)methyl)-2,2-difluoroacetamide.

In one embodiment, provided herein are methods of treating, preventing, managing, and/or ameliorating a myelodysplastic syndrome (MDS) by administering to a subject a 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, an isotopologue, pharmaceutically acceptable salt, tautomer, solvate, hydrate, co-crystal, clathrate, or polymorph thereof ("Compound 1"). In one embodiment, the MDS is relapsed, resistant or refractory MDS. In one embodiment, provided herein is a method of treating of MDS by administering to a subject a 2-(4-chlorophenyl)-N-((2-(2,6-dioxopiperidin-3-yl)-1-oxoisoindolin-5-yl)methyl)-2,2-difluoroacetamide.

In one embodiment, provided herein are methods of treating, preventing, managing, and/or ameliorating hematologic malignancies by administering to a subject an effective amount of Compound 1 in a cycle, wherein the cycle comprises administering Compound 1 in a dose of about 0.1 mg to about 20 mg on days 1 to 5 of a 28 day cycle. In one embodiment, provided herein is a method of treating of AML by administering to a subject a 2-(4-chlorophenyl)-N-((2-(2,6-dioxopiperidin-3-yl)-1-oxoisoindolin-5-yl)methyl)-2,2-difluoroacetamide in a cycle, wherein the cycle comprises administering 2-(4-chlorophenyl)-N-((2-(2,6-dioxopiperidin-3-yl)-1-oxoisoindolin-5-yl)methyl)-2,2-difluoroacetamide in a dose of about 0.1 mg to about 20 mg on days 1 to 5 of a 28 day cycle. In one embodiment, provided herein is a method of treating of relapsed or refractory AML by administering to a subject a 2-(4-chlorophenyl)-N-((2-(2,6-dioxopiperidin-3-yl)-1-oxoisoindolin-5-yl)methyl)-2,2-difluoroacetamide in a cycle, wherein the cycle comprises administering 2-(4-chlorophenyl)-N-((2-(2, 6-dioxopiperidin-3-yl)-1-oxoisoindolin-5-yl)methyl)-2,2-difluoroacetamide in a dose of about 0.1 mg to about 20 mg on days 1 to 5 of a 28 day cycle. In one embodiment, provided herein is a method of treating of MDS by administering to a subject a 2-(4-chlorophenyl)-N-((2-(2,6-dioxopiperidin-3-yl)-1-oxoisoindolin-5-yl)methyl)-2,2-difluoroacetamide in a cycle, wherein the cycle comprises administering 2-(4-chlorophenyl)-N-((2-(2,6-dioxopiperidin-3-yl)-1-oxoisoindolin-5-yl)methyl)-2,2-difluoroacetamide in a dose of about 0.1 mg to about 20 mg on days 1 to 5 of a 28 day cycle.

In one embodiment, the subject is administered calcium, calcitriol, and/or vitamin D supplementation prior to administration of Compound 1. In one embodiment, the subject is administered calcium, calcitriol, and vitamin D supplementation at least 3 days prior to administration of Compound 1 on day 1 of the treatment cycle.

In one embodiment, Compound 1 is administered in a treatment cycle that includes an administration period of at least 2 days and a rest period of at least 1 day.

In one embodiment, the treatment cycle includes an administration period of at least 5 days in a 28 day cycle. In one embodiment, the treatment cycle includes an administration period of 5 days in a 28 day cycle.

In certain embodiments, provided herein are pharmaceutical compositions, single unit dosage forms, and kits comprising Compound 1 suitable for use in treating, preventing, ameliorating and/or managing leukemia, including AML, and more particularly relapsed or refractory AML. In certain embodiments, provided herein are pharmaceutical compositions, single unit dosage forms, and kits comprising Compound 1 suitable for use in treating, preventing, ameliorating and/or managing MDS. In certain embodiments, such compositions include Compound 1 optionally in combination with one or more other therapeutic agents. In certain embodiments, provided herein are pharmaceutical compositions, comprising Compound 1 for use in treating leukemia, including AML, and more particularly relapsed or refractory AML. In certain embodiments, provided herein are pharmaceutical compositions comprising Compound 1 for use in treating MDS. In certain embodiments, such compositions include Compound 1 optionally in combination with one or more other therapeutic agents.

These and other aspects of the subject matter described herein will become evident upon reference to the following detailed description.

5. BRIEF DESCRIPTION OF THE FIGURES

Figure 6:
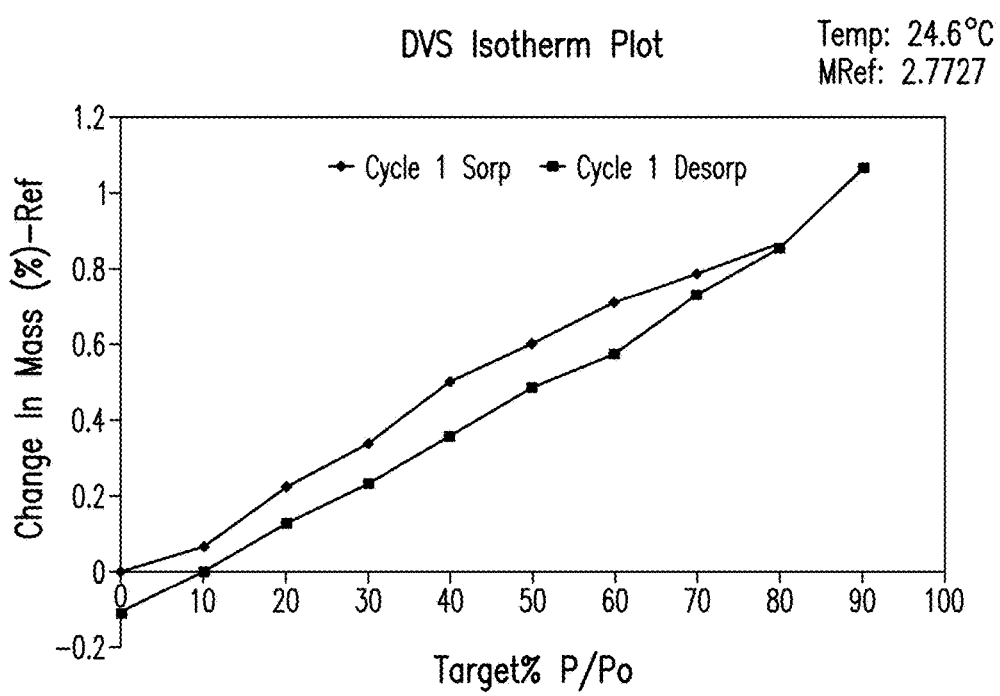

FIG. 6 provides a dynamic vapor sorption (DVS) isotherm plot of Form A of Compound 1.

Figure 7:
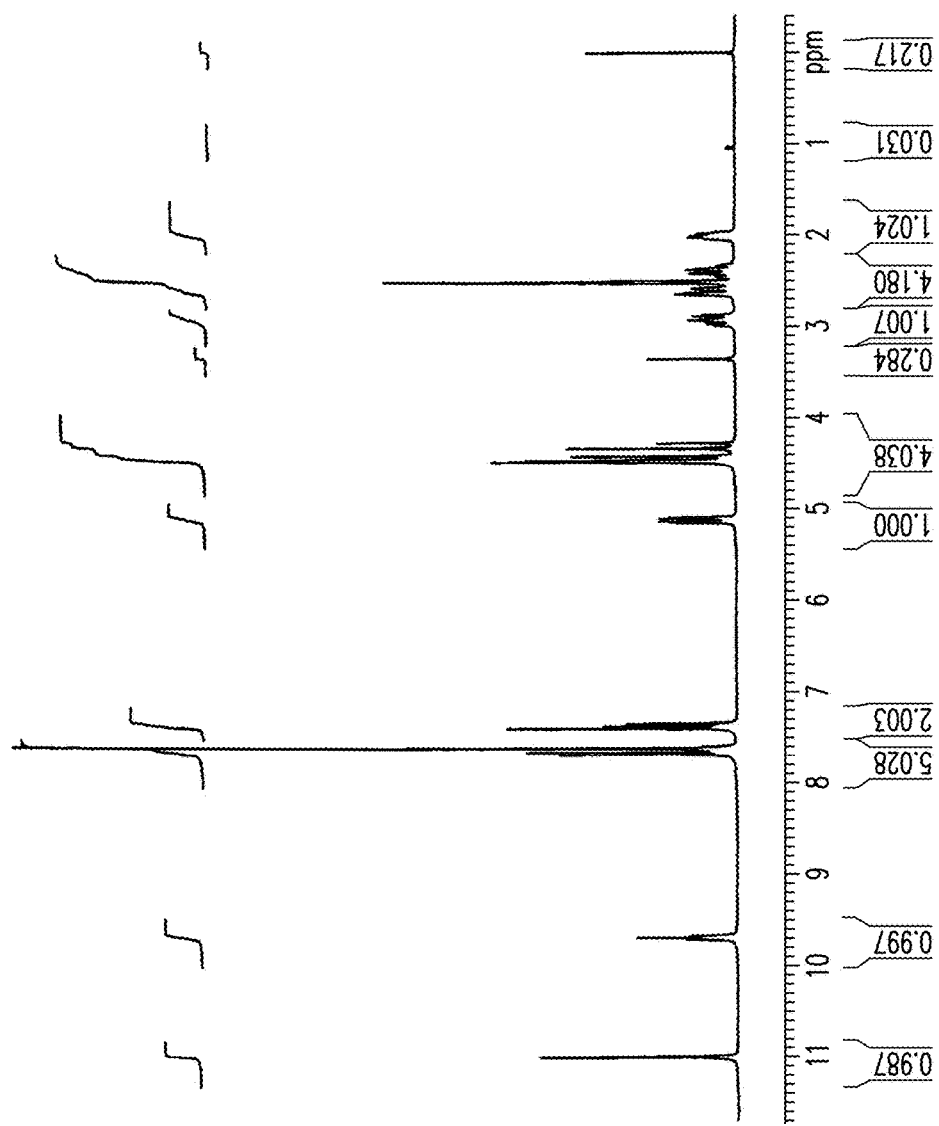

FIG. 7 provides a $^1$H NMR spectrum of Form A of Compound 1.

Figure 8:
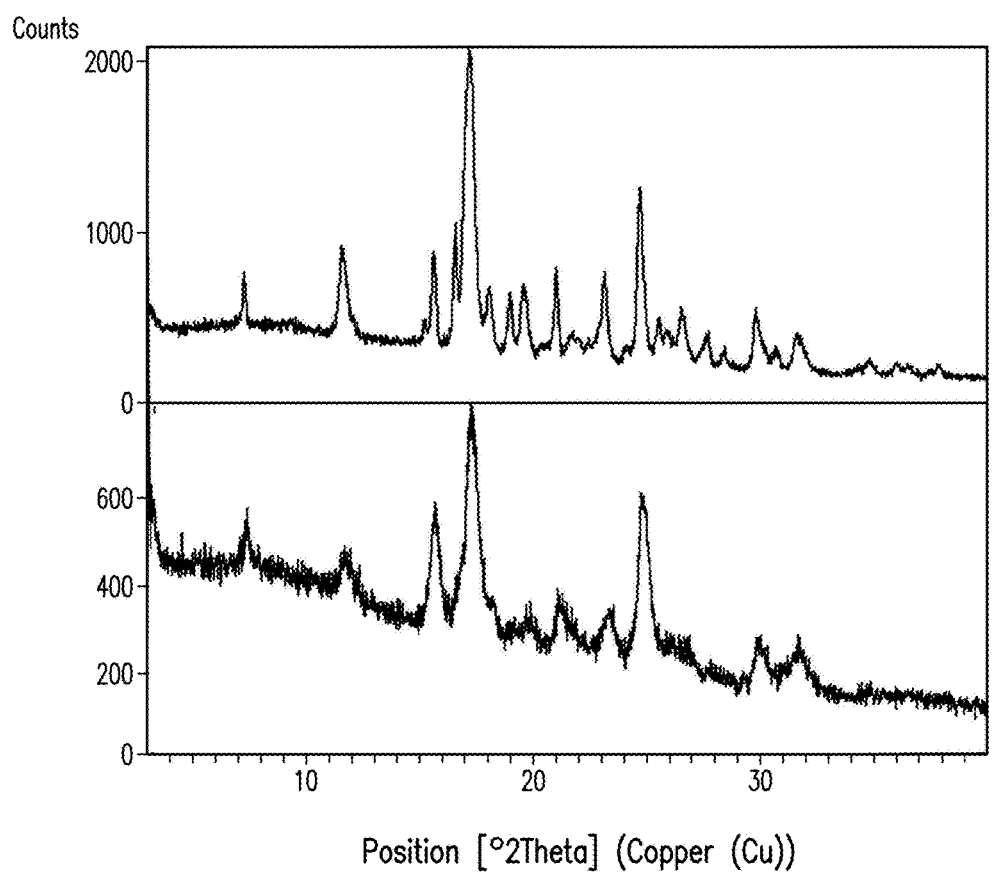

FIG. 8 depicts the comparison of the X-ray powder diffractogram plots of Form A of Compound 1 before (a) and after (b) compression.

Figure 9:
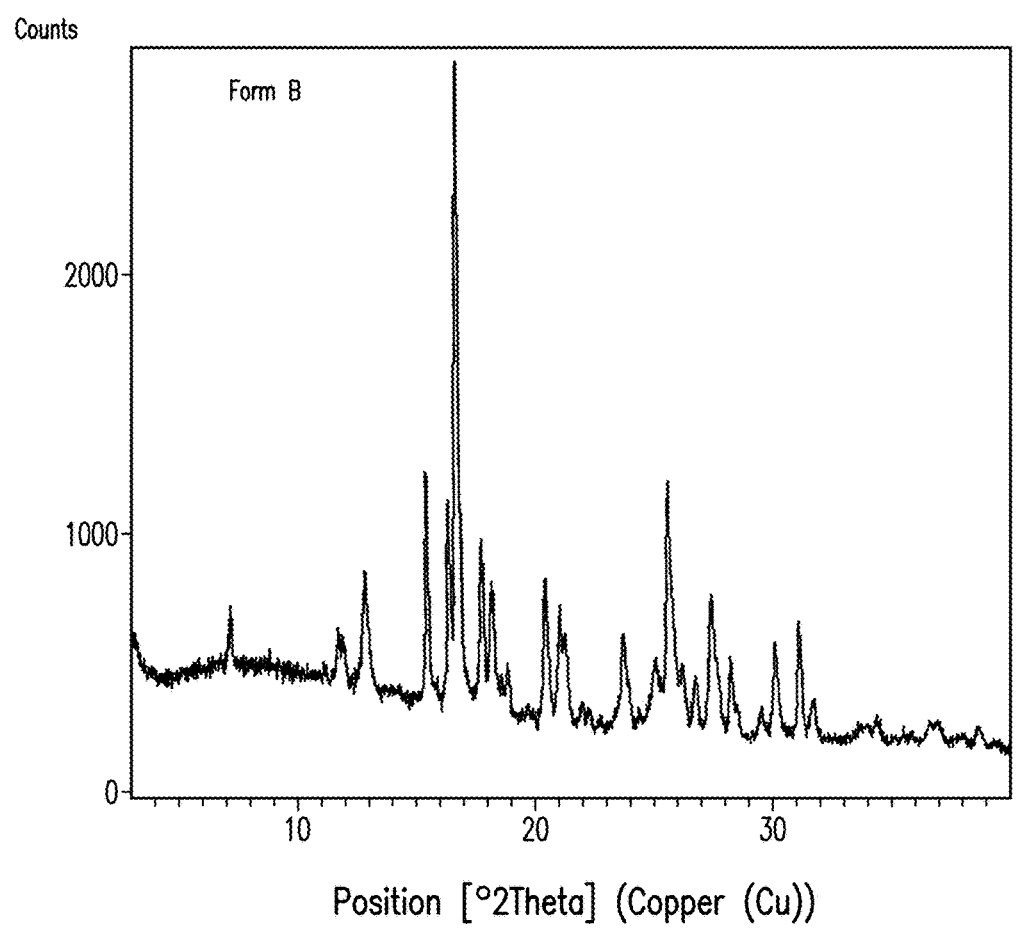

FIG. 9 depicts an XRPD plot of Form B of Compound 1.

Figure 10:
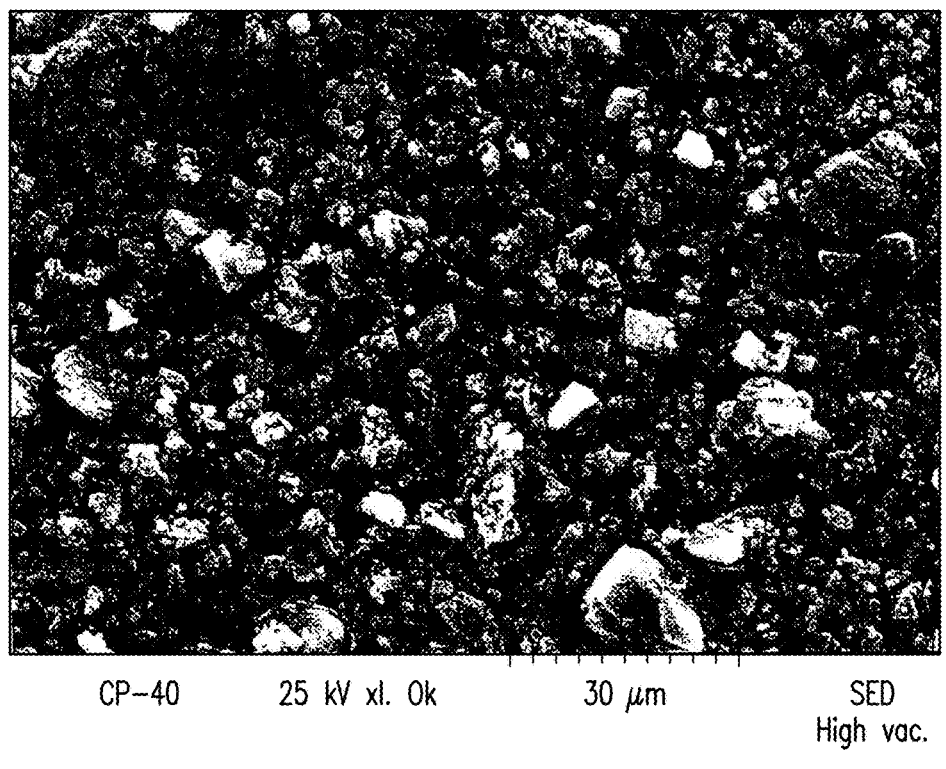

FIG. 10 depicts a SEM image of Form B of Compound 1.

Figure 11:
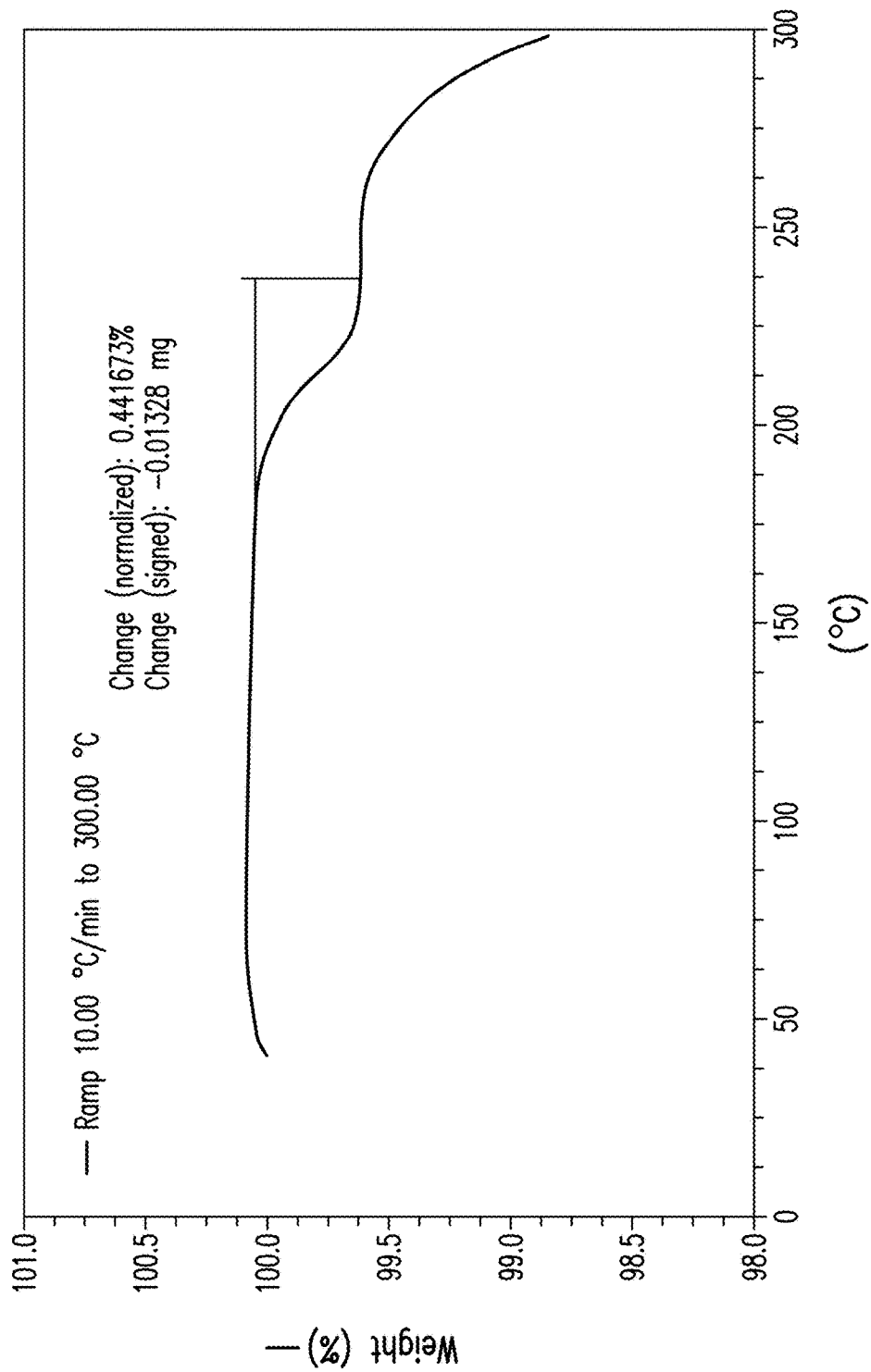

FIG. 11 depicts a TGA thermogram plot of Form B of Compound 1.

Figure 12:
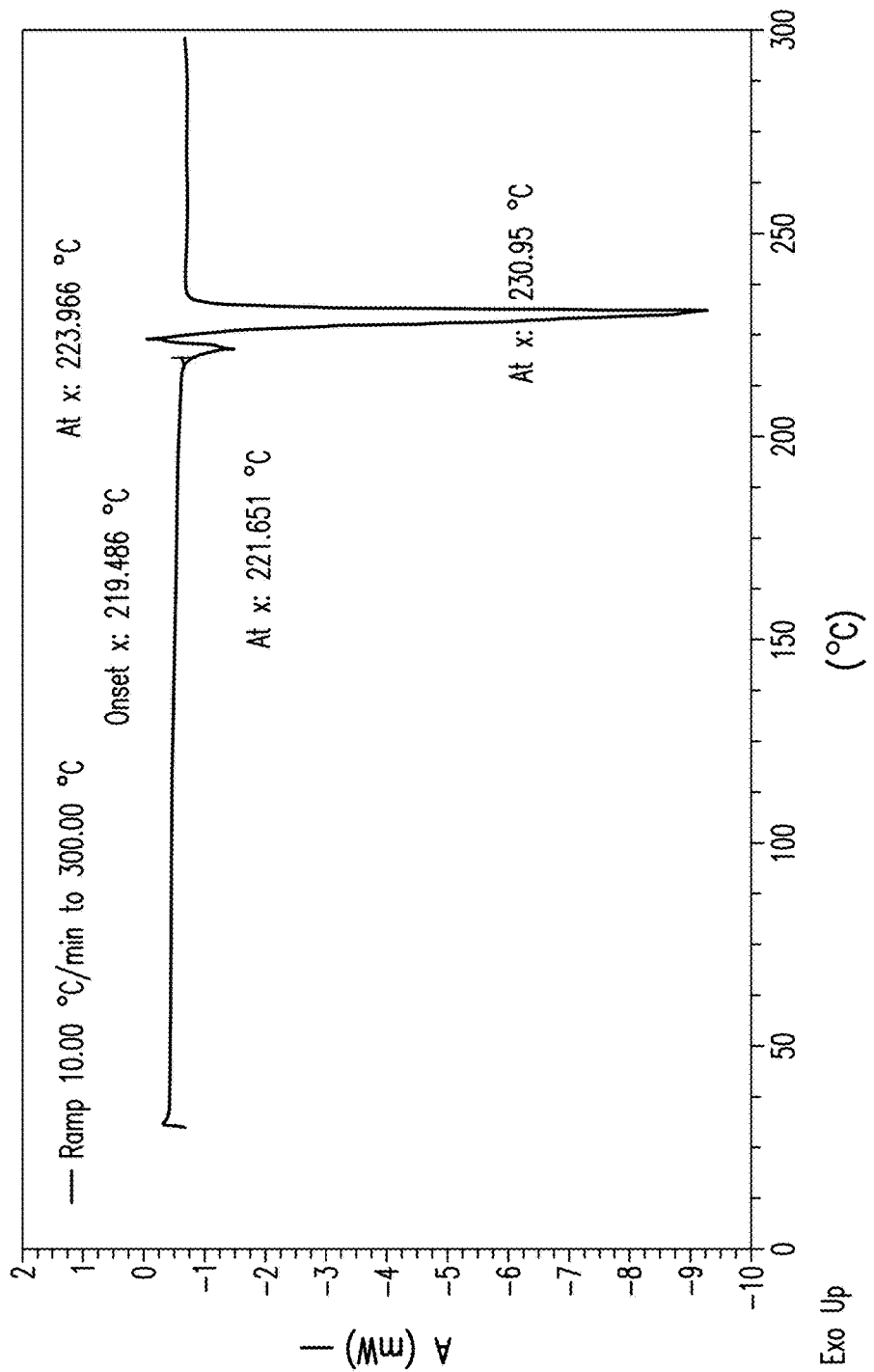

FIG. 12 depicts a DSC thermogram plot of Form B of Compound 1.

Figure 13:
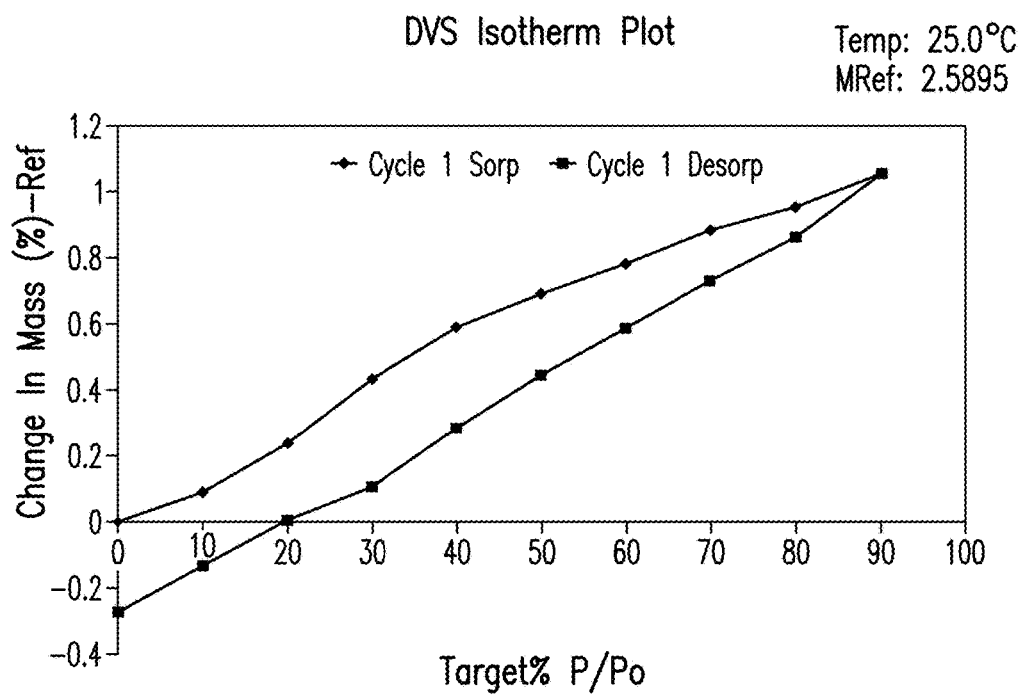

FIG. 13 provides a DVS isothterm plot of Form B of Compound 1.

Figure 14:
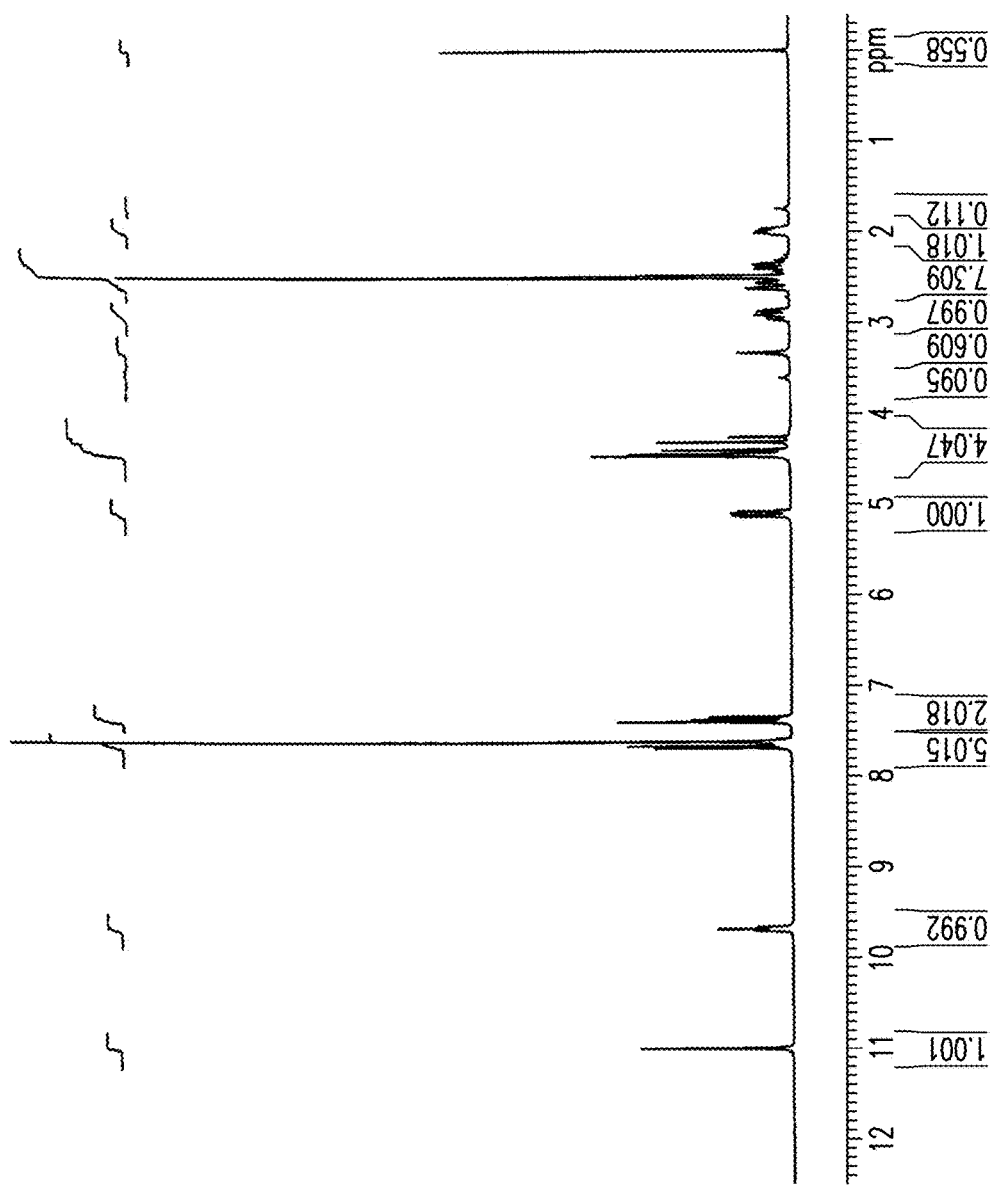

FIG. 14 provides a $^1$H NMR spectrum of Form B of Compound 1.

Figure 15:
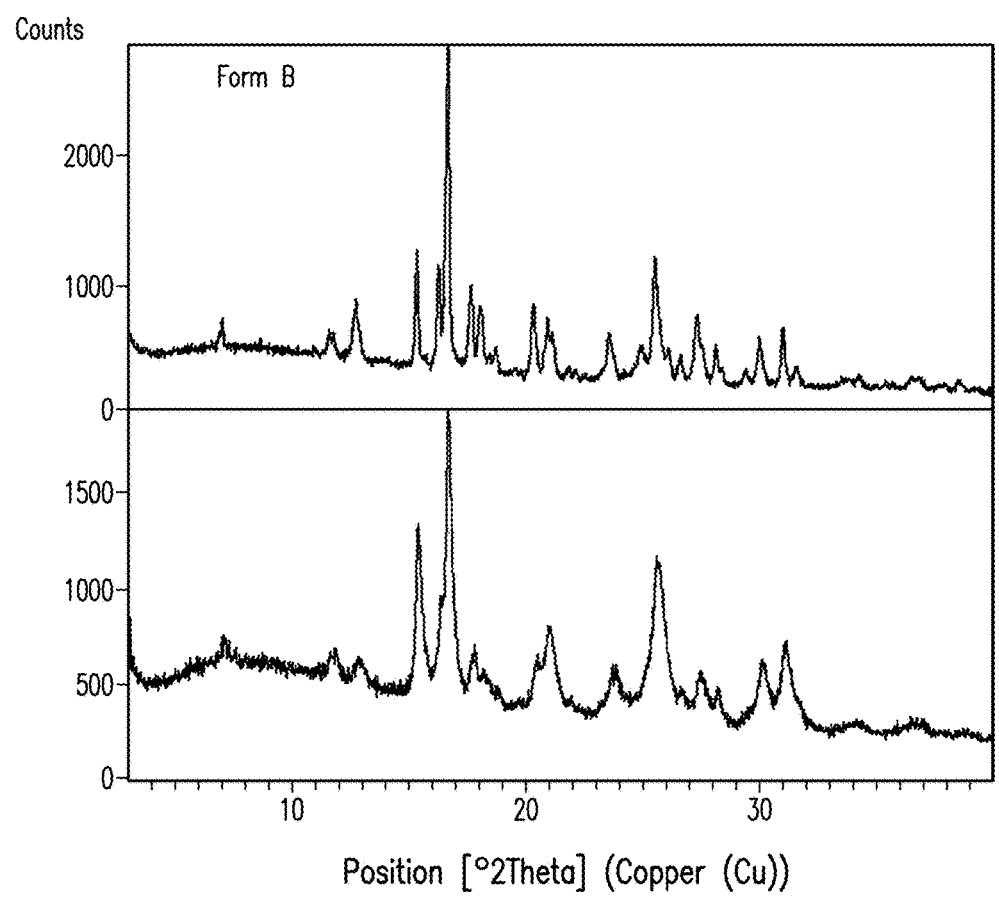

FIG. 15 depicts the comparison of the X-ray powder diffractogram plots of Form B of Compound 1 before (a) and after (b) compression.

Figure 16:
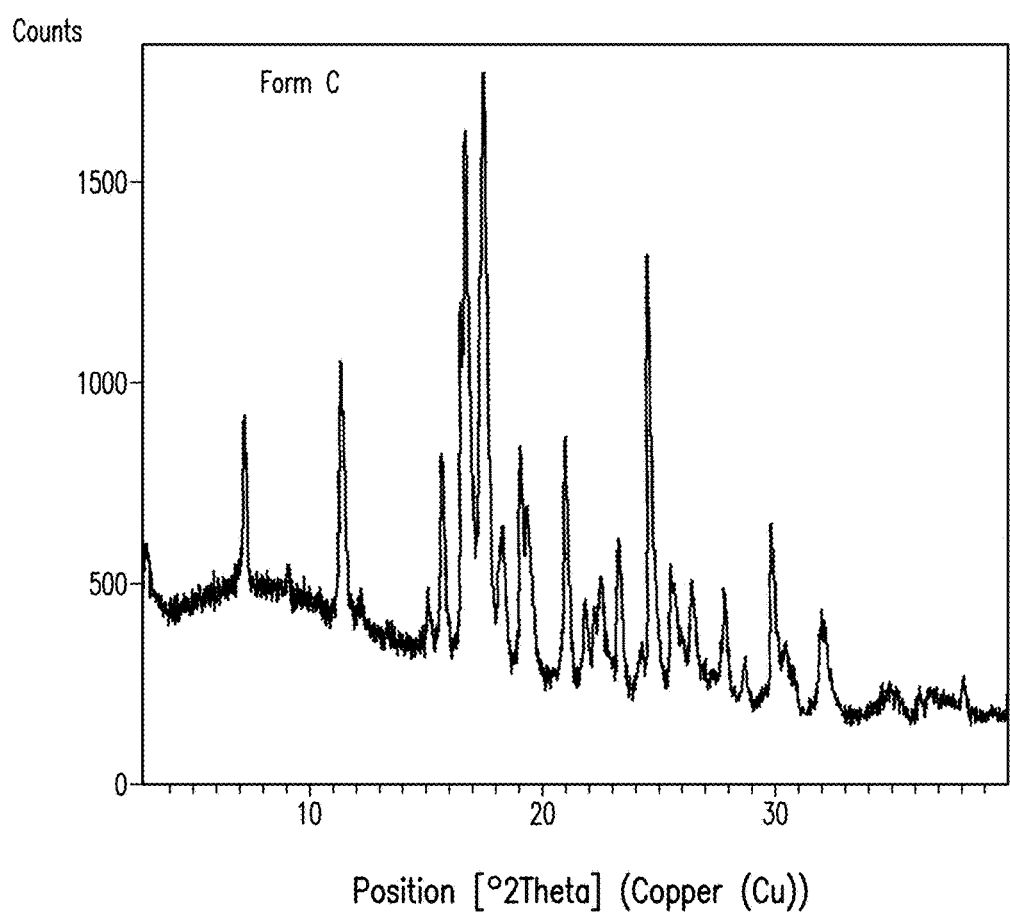

FIG. 16 depicts an XRPD plot of Form C of Compound 1.

Figure 17:
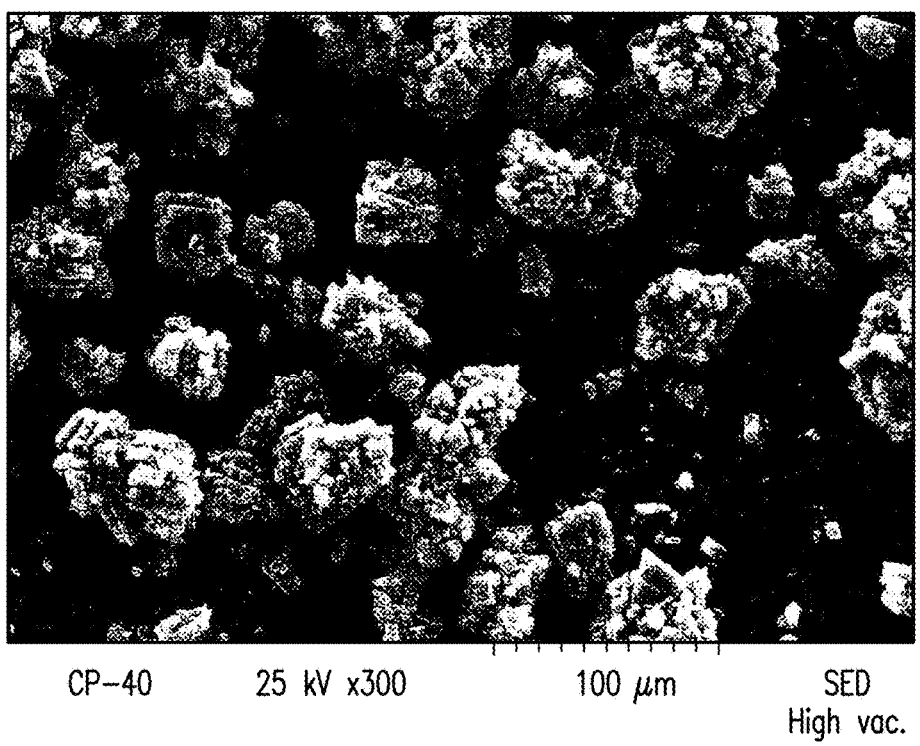

FIG. 17 depicts a SEM image of Form C of Compound 1.

Figure 18:
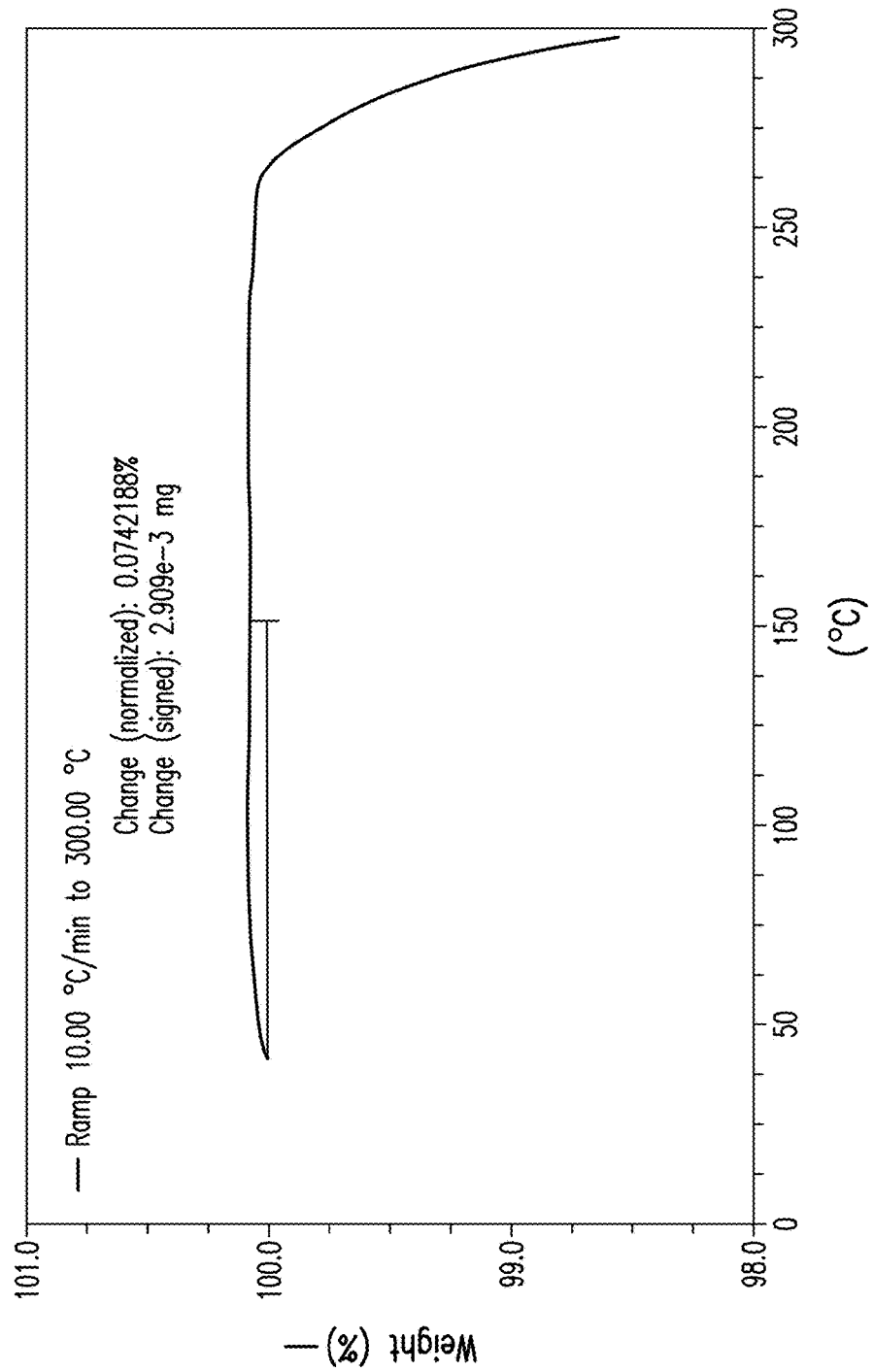

FIG. 18 depicts a TGA thermogram plot of Form C of Compound 1.

Figure 19:
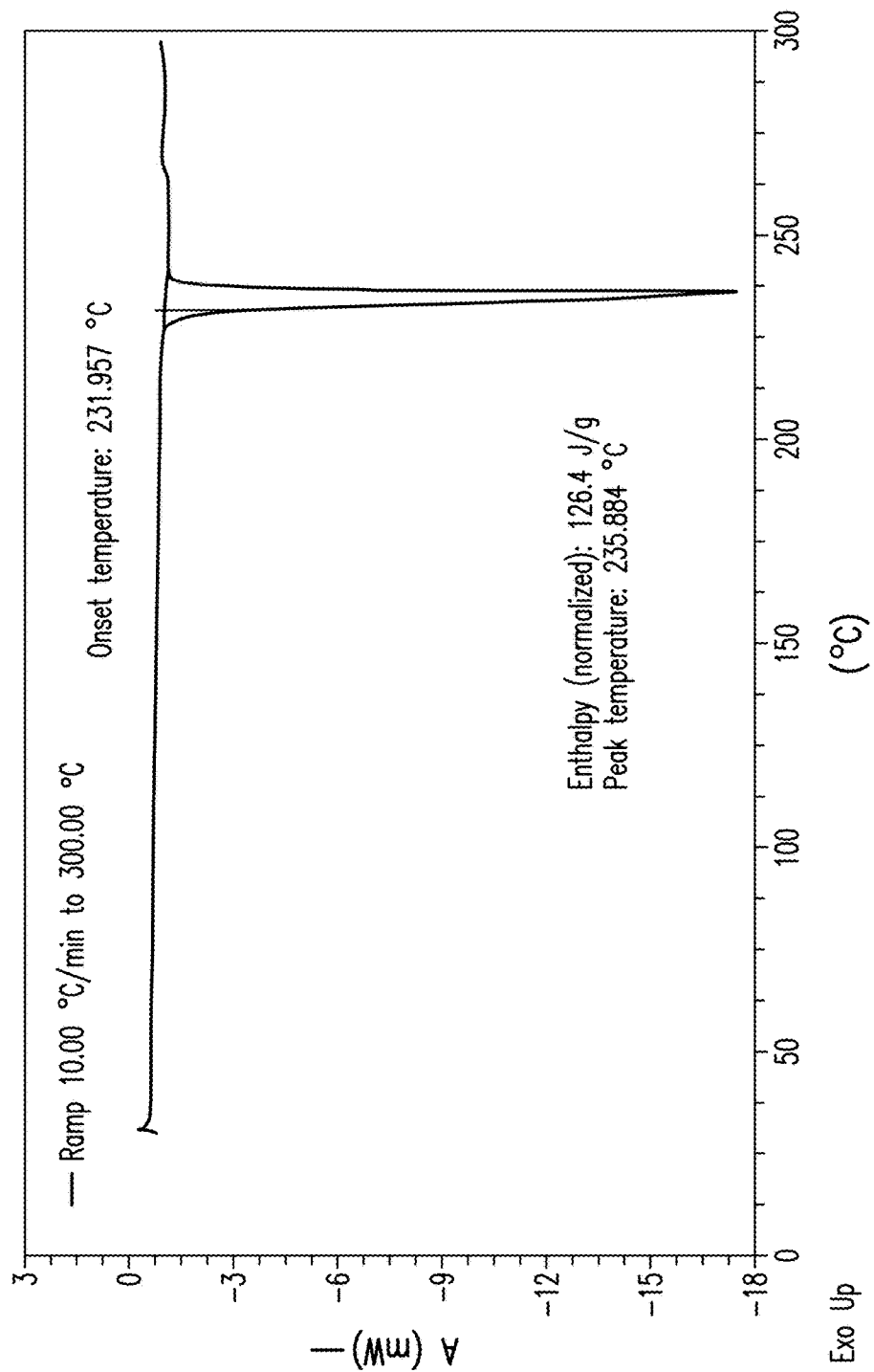

FIG. 19 depicts a DSC thermogram of Form C of Compound 1.

Figure 20:
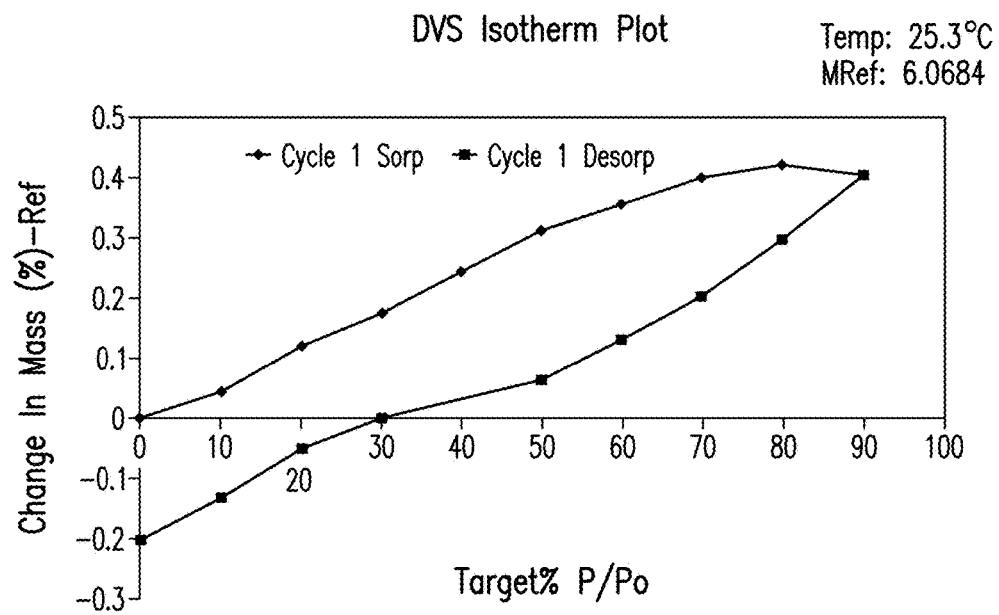

FIG. 20 provides a DVS isotherm plot of Form C of Compound 1.

Figure 21:
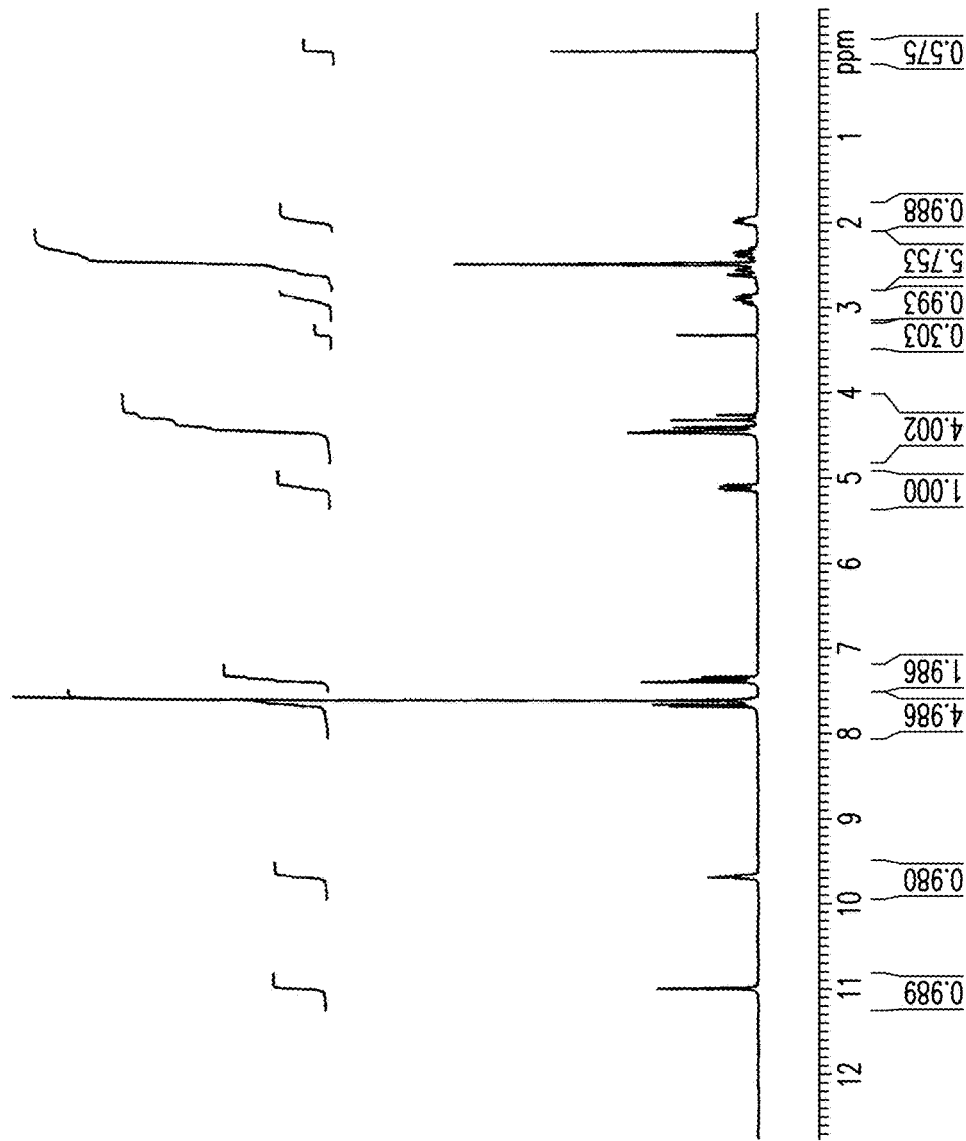

FIG. 21 provides a $^1$H NMR spectrum of Form C of Compound 1.

Figure 22:
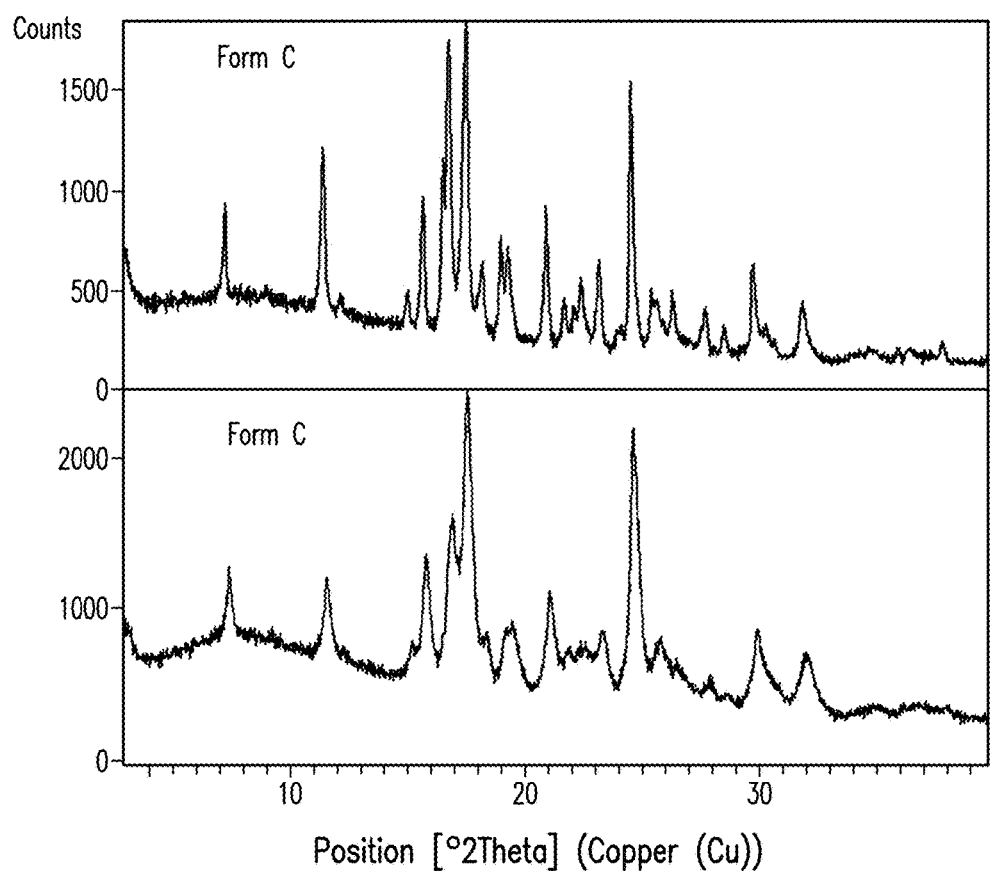

FIG. 22 depicts the comparison of the X-ray powder diffractogram plots of Form C of Compound 1 before (a) and after (b) compression.

Figure 23:
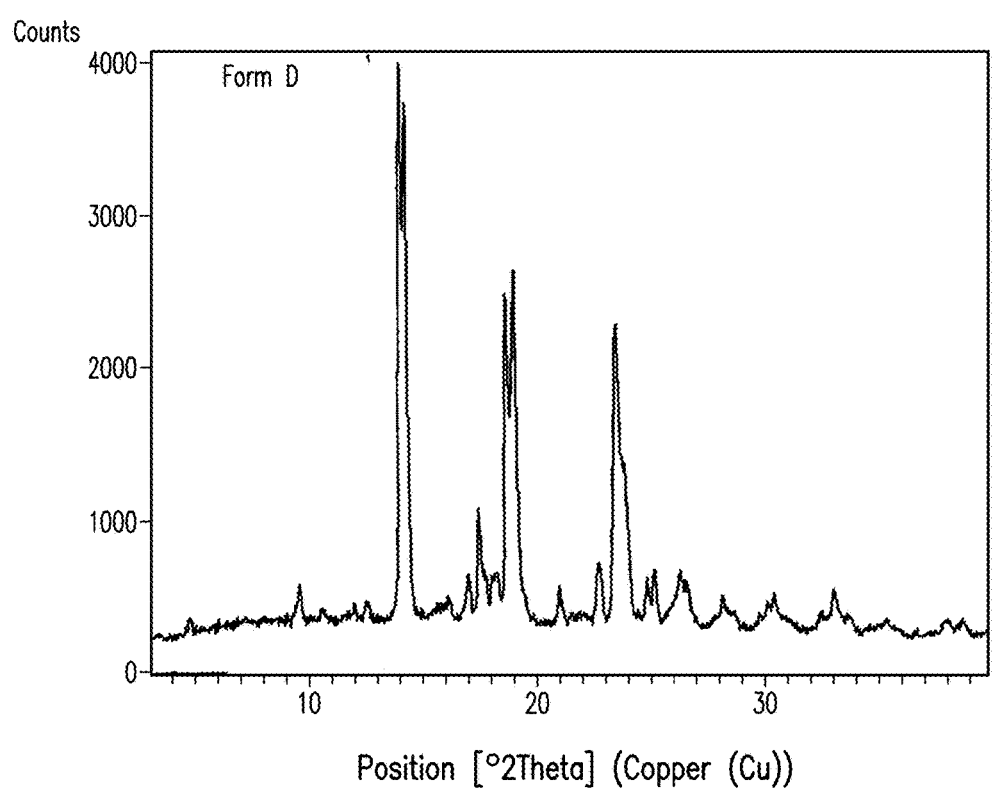

FIG. 23 depicts an XRPD plot of Form D of Compound 1.

Figure 24:
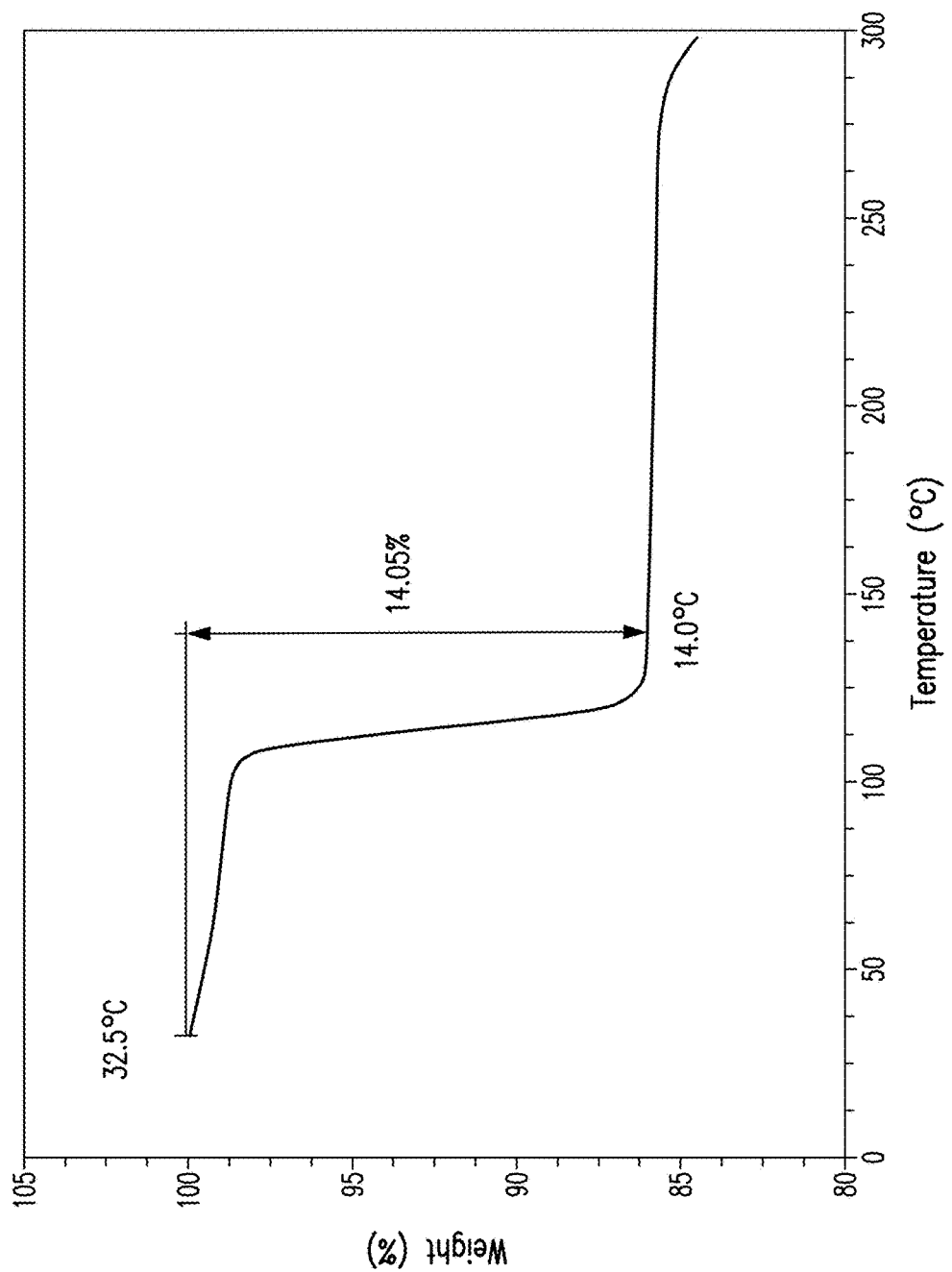

FIG. 24 depicts a TGA thermogram plot of Form D of Compound 1.

Figure 25:
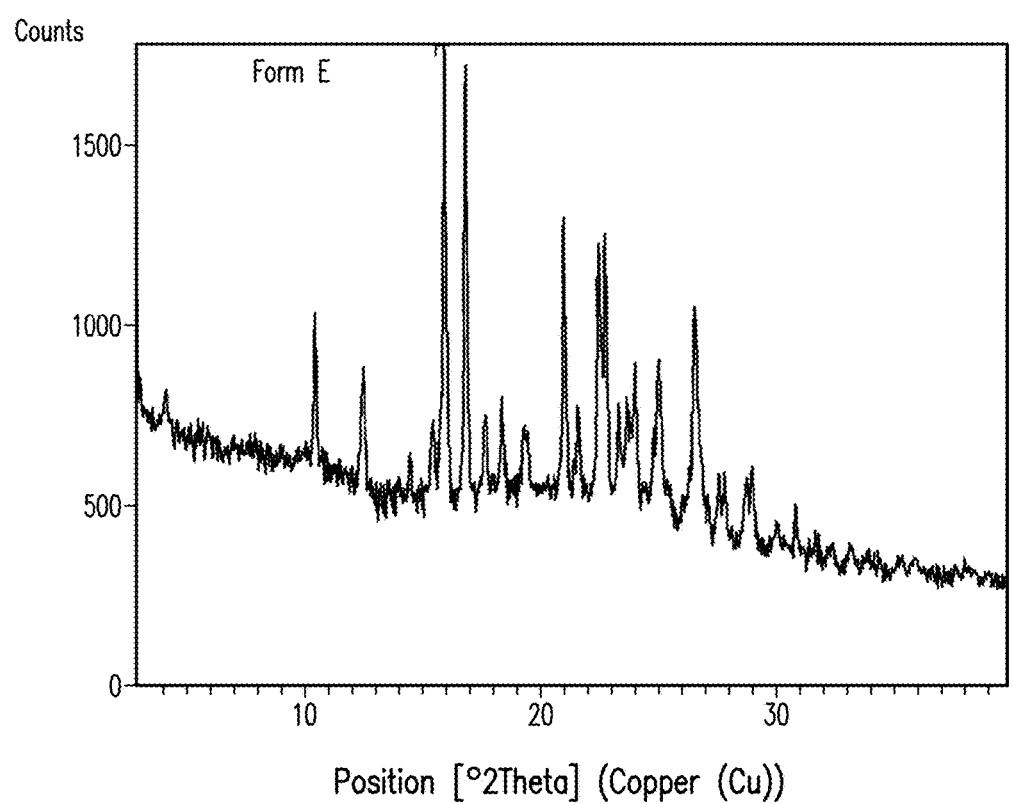

FIG. 25 depicts an XRPD plot of Form E of Compound 1.

Figure 26:
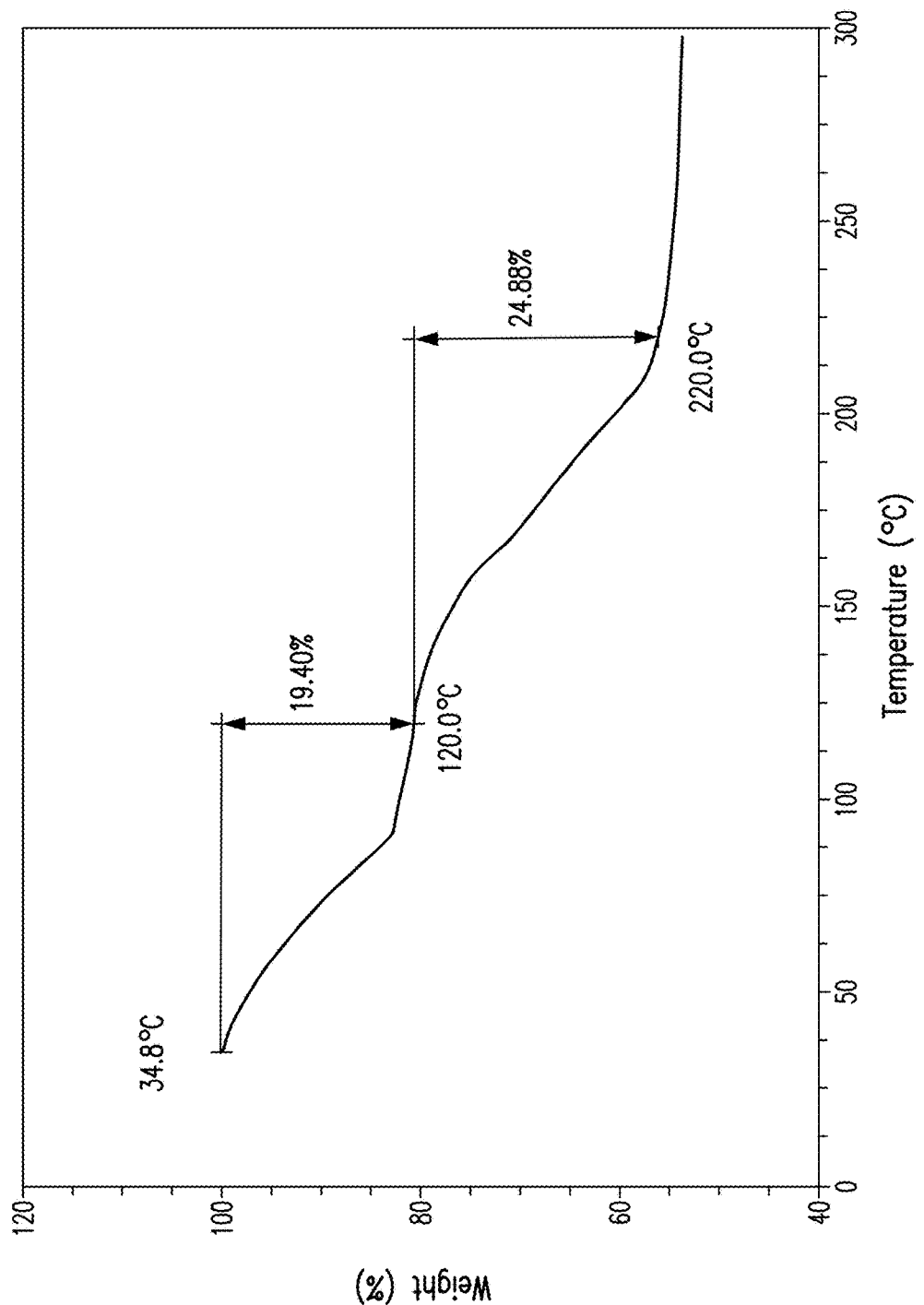

FIG. 26 depicts a TGA thermogram plot of Form E of Compound 1.

Figure 27:
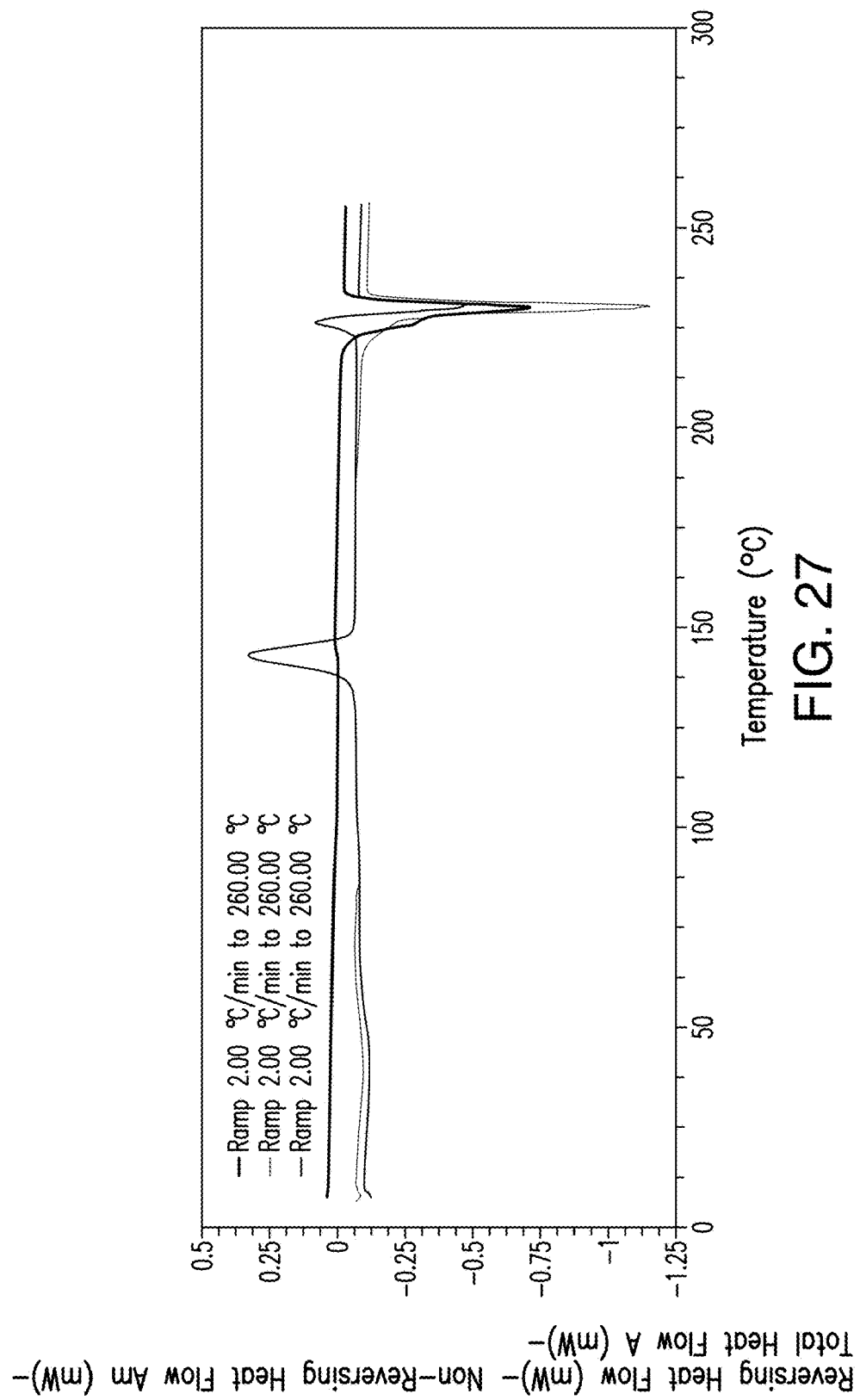

FIG. 27 depicts the modulated DSC thermogramplot of amorphous Compound 1.

Figure 28:
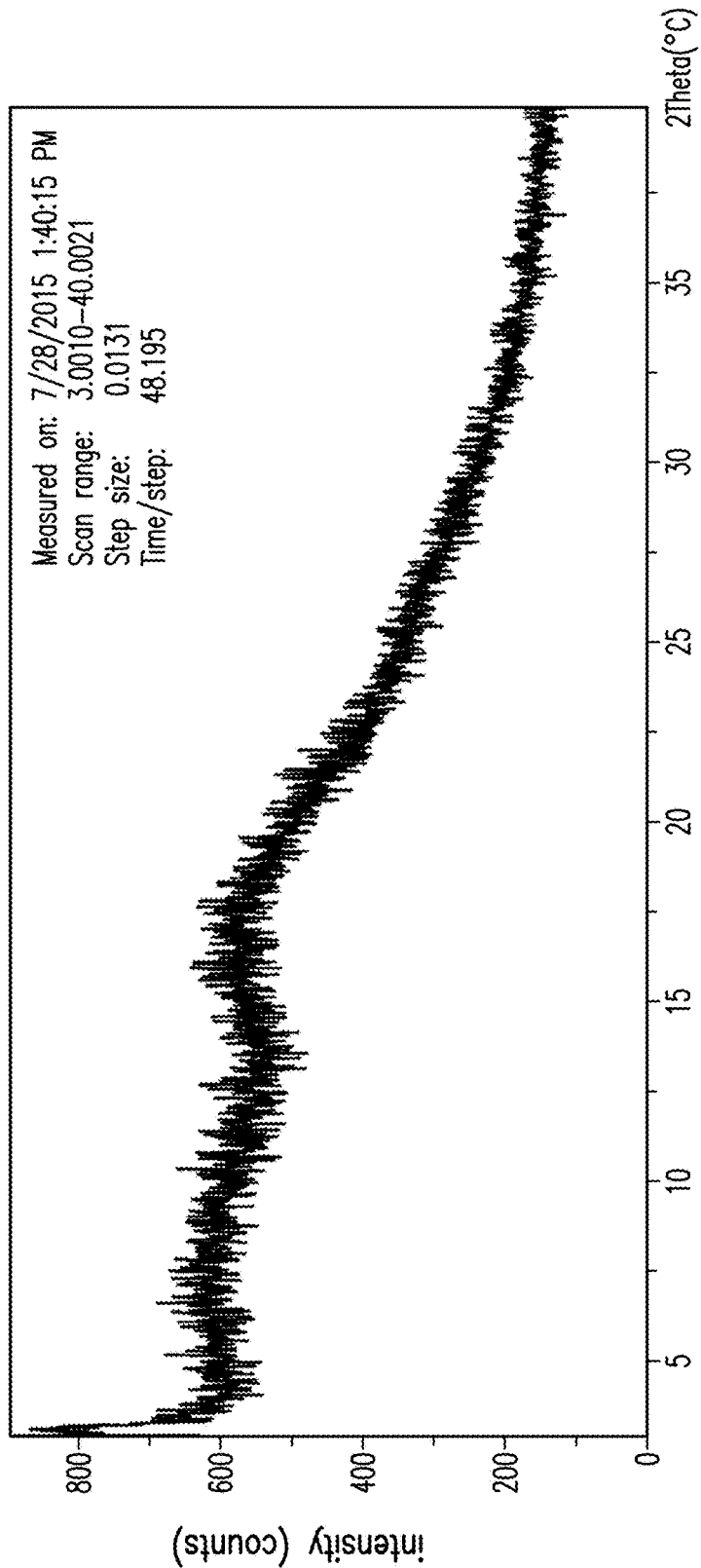

FIG. 28 depicts an XRPD plot of amorphous Compound 1.

Figure 29:
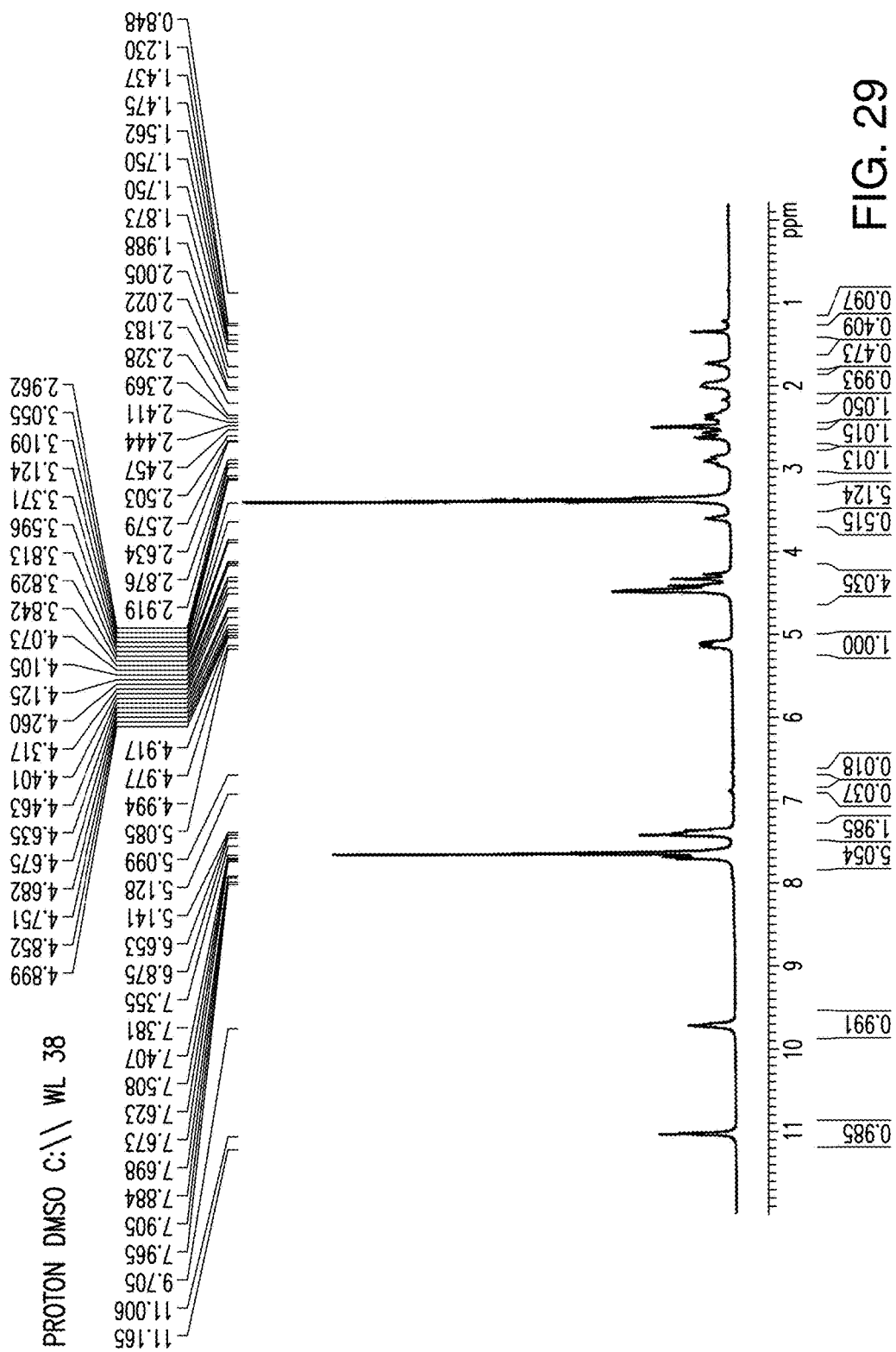

FIG. 29 depicts a $^1$H NMR spectrum of amorphous Compound 1.

Figure 30A:
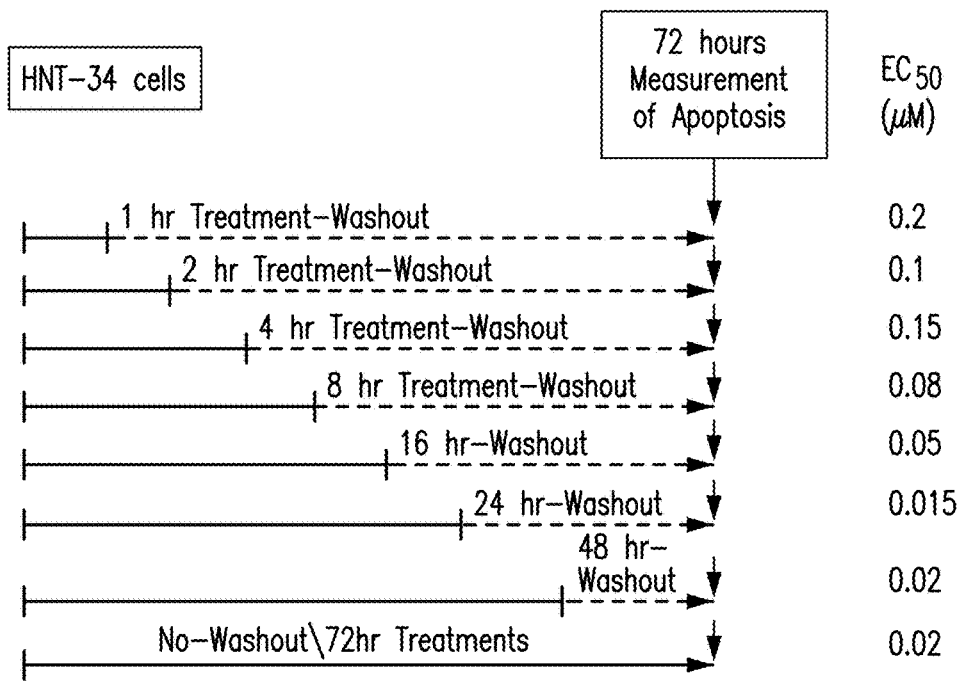
Figure 30B:
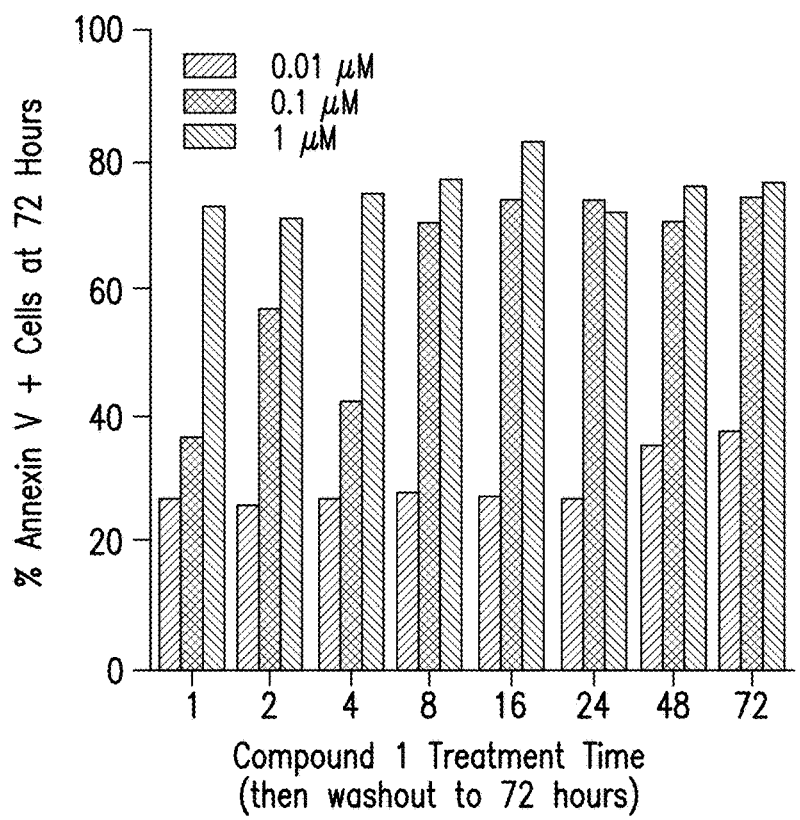

FIGS. 30 A and 30 B demonstrate that HNT-34 cells are committed to apoptosis within 8 to 16 hours of incubation with Compound 1.

Figure 31:
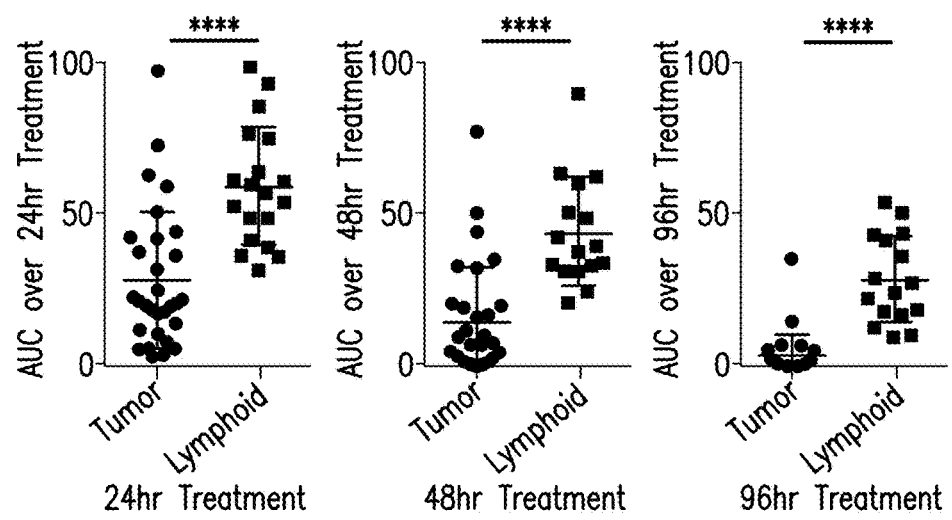

FIG. 31 provides comparative analysis of activity areas from tumor versus normal lymphoid cells in AML bone marrow samples. In the figure, **** p<0.0001. The symbols in the figure represent the individual activity area value of tumor (circles) and lymphoid (squares) populations of the bone marrow AML samples, calculated from the estimated fitting functions.

Figure 32:
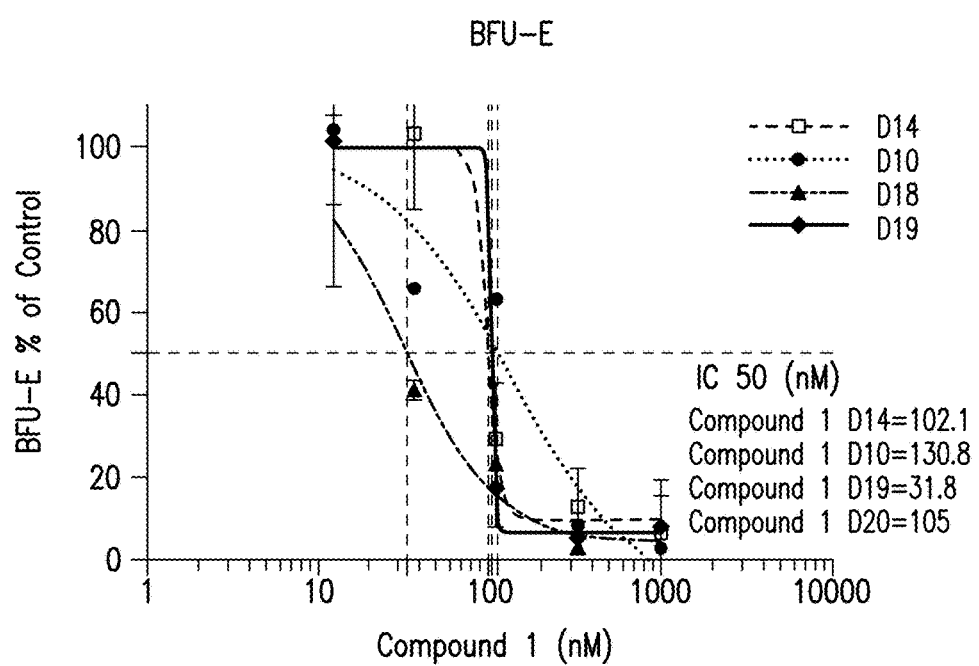

FIG. 32 illustrates inhibition of granulo-monocytic and erythroid progenitors from four different donors treated with Compound 1.

Figure 33A:
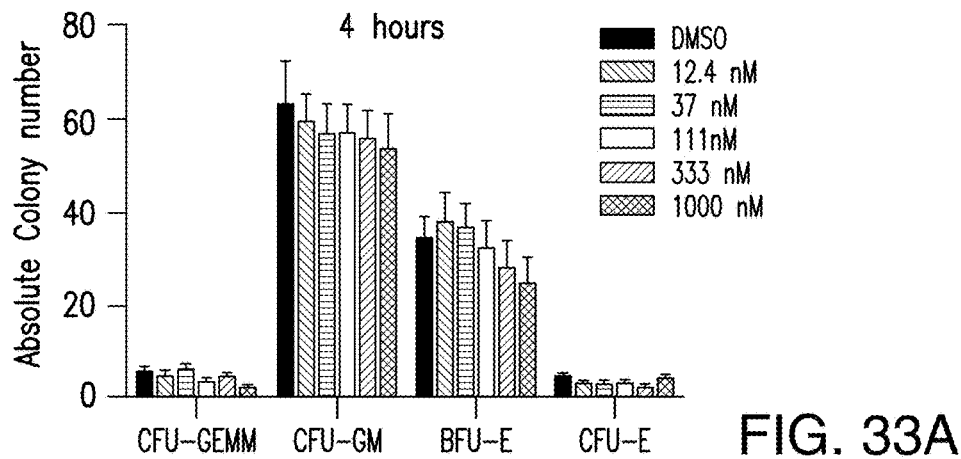
Figure 33B:
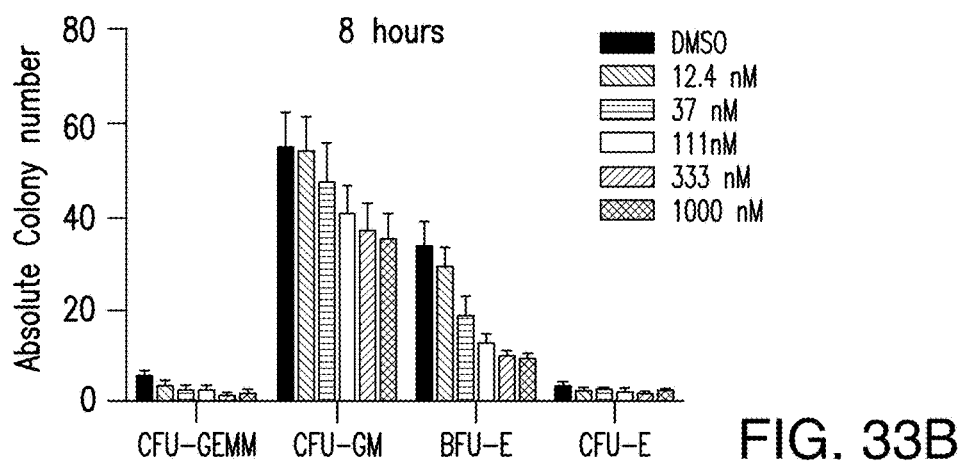
Figure 33C:
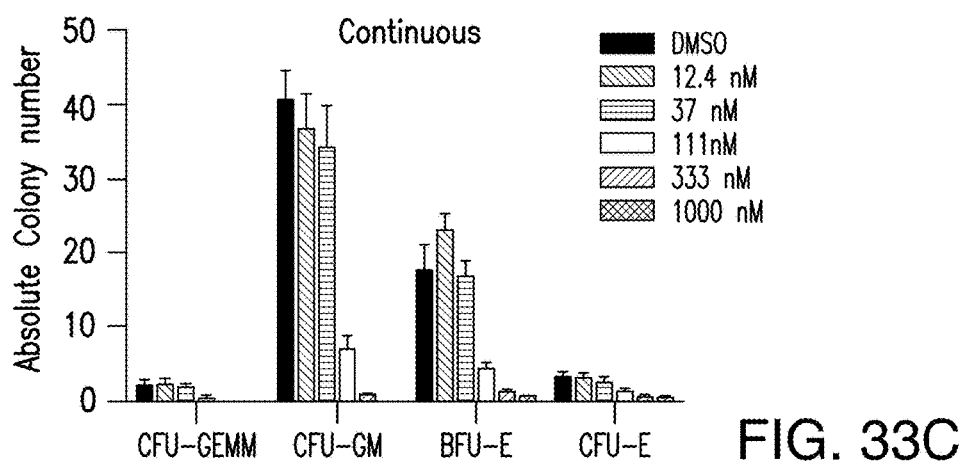

FIGS. 33A, 33B and 33C provide colony numbers of myeloid and erythroid progenitors from donors HD46, HD47, HD48, and HD50 after different lengths of exposure to Compound 1. In FIGS. 33A-33C, *p<0.05; p<0.01; *p<0.001; ****p<0.0001 compared with DMSO control using 2-way ANOVA followed by Tukey's multiple comparisons test.

Figure 34:
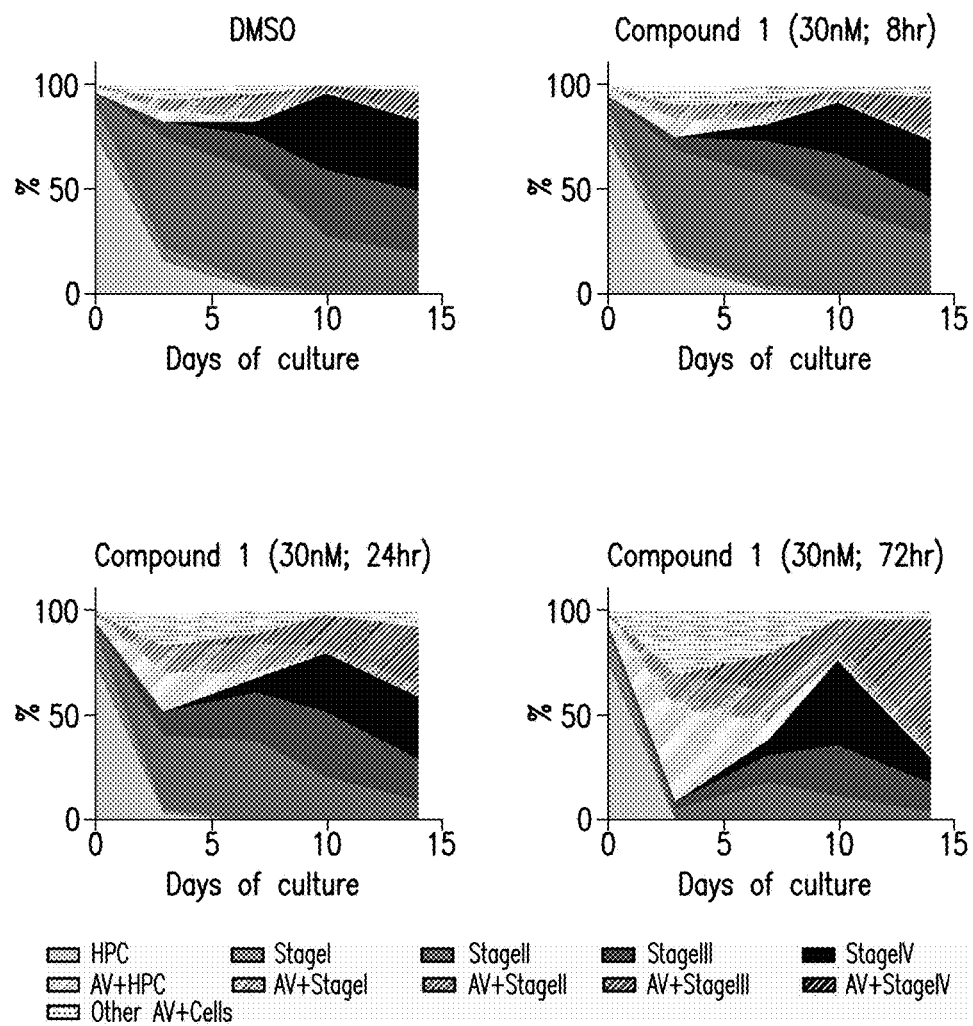

FIG. 34 provides results of cell viability study upon exposure to Compound 1 at 30 nM concentration.

Figure 35A:
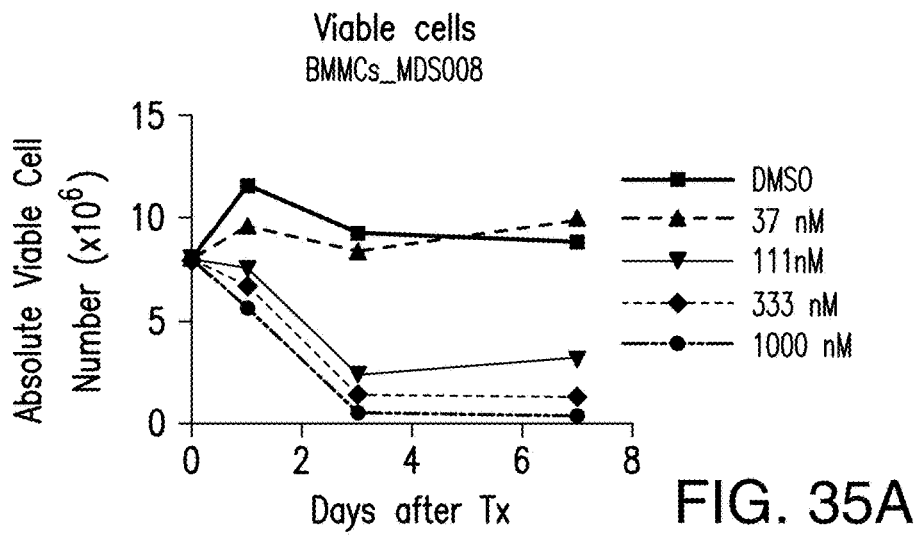

FIG. 35A demonstrates the effect of 24 hours exposure to Compound 1 on bone marrow cells from patients with myelodysplastic syndrome. Viable cell numbers were reduced in dose-dependent manner (A).

Figure 35B:
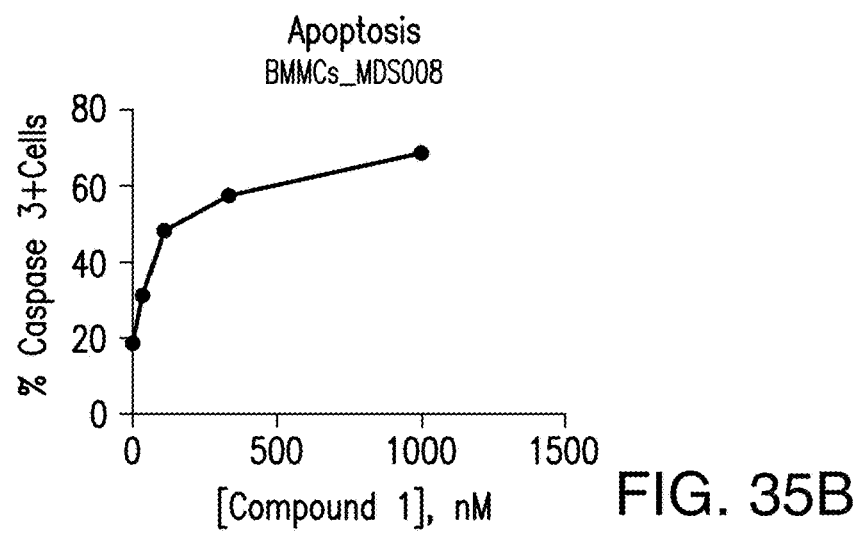

FIG. 35B demonstrates that the effect of 24 hours exposure to Compound 1 on bone marrow cells from patients with myelodysplastic syndrome was mediated by induction of apoptosis measured by caspase 3 activation (B).

Figure 35C:
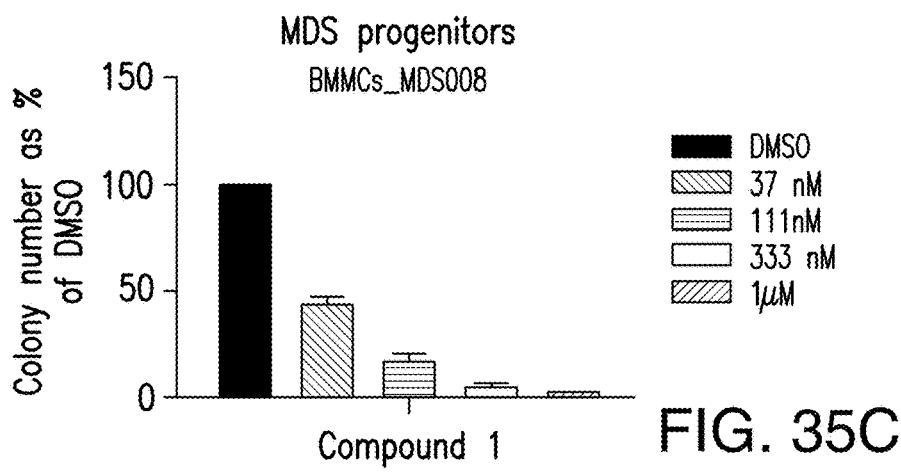

FIG. 35C demonstrates stronger effect of Compound 1 in MDS progenitors (C) in colony forming assays.

Figure 36A:
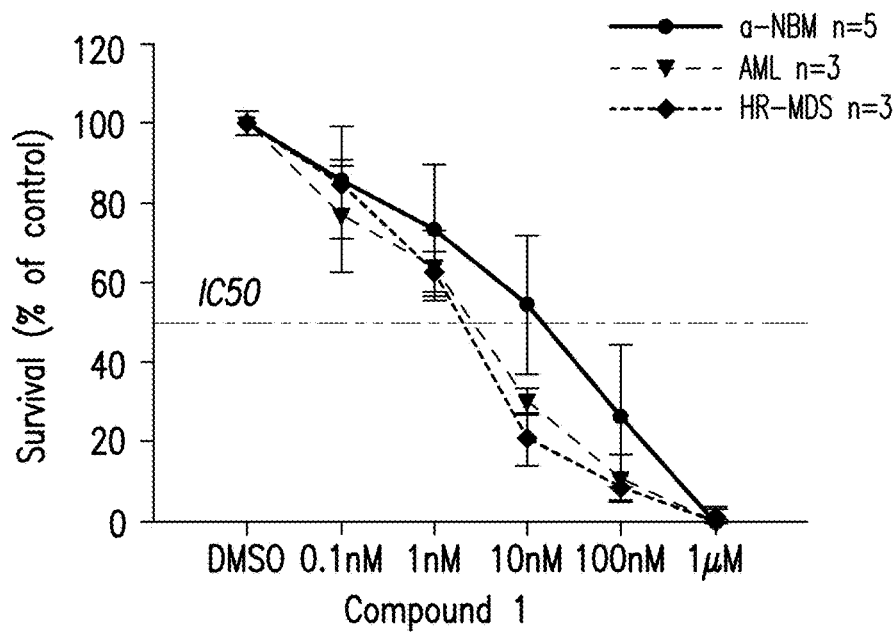

FIG. 36A demonstrates the effect of Compound 1 on the maintenance of HR-MDS and AML progenitors in stromal co-cultures in colony-formation assays: CD34+ bone marrow cells from MDS (n=3), sAML (n=4), and normal donor (NBM; n=5) were co-cultured with SL/M2 stroma for 1 weeks, and then plated in methylcellulose for two weeks.

Figure 36B:
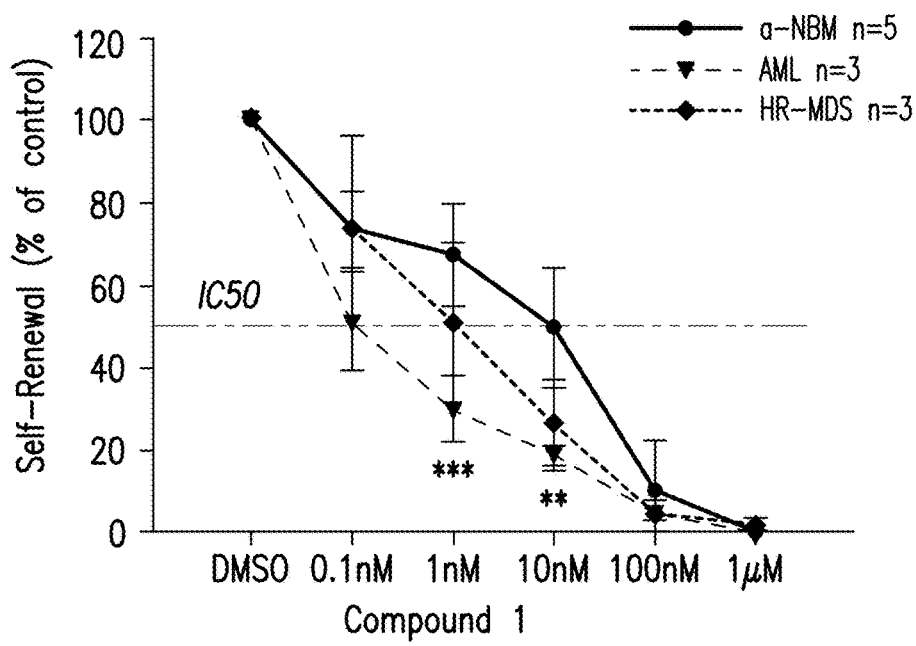

FIG. 36B demonstrates the effect of Compound 1 on the maintenance of HR-MDS and AML progenitors in stromal co-cultures in colony-replating assays: same number of colonies from FIG. 36A were replated in methylcellulose for two additional weeks. Compound 1 at the indicated concentrations was added at the initiation of co-culture, with DMSO as a vehicle control. Colonies were scored to determine the effect of Compound 1 on cell survival (FIG. 36A) and self-renewal (FIG. 36B). *, p<0.001, AML vs normal bone marrow controls treated with 1 nM of compound 1 (one-way ANOVA). , p=0.01, AML vs normal bone marrow controls treated with 10 nM of Compound 1 (one-way ANOVA). Error bars represent mean values±SD.

6. DETAILED DESCRIPTION

6.1 Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

The term Compound 1 refers to "2-(4-chlorophenyl)-N-((2-(2,6-dioxopiperidin-3-yl)-1-oxoisoindolin-5-yl)methyl)-2,2-difluoroacetamide" having the structure:

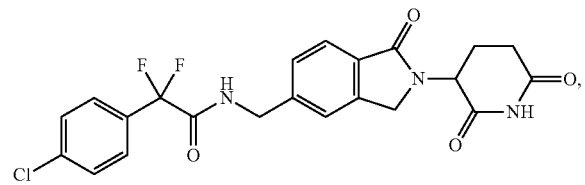 [SMILES: O=C1CCC(N2Cc3cc(CNC(=O)C(F)(F)c4ccc(Cl)cc4)ccc3C2=O)C(=O)N1]

and its stereoisomers or mixture of stereoisomers, isotopologues, pharmaceutically acceptable salts, tautomers, solvates, hydrates, co-crystals, clathrates, or polymorphs thereof. In certain embodiments, Compound 1 refers to 2-(4-chlorophenyl)-N-((2-(2,6-dioxopiperidin-3-yl)-1-oxoisoindolin-5-yl)methyl)-2,2-difluoroacetamide and its tautomers. In certain embodiments, Compound 1 refers to a polymorph of 2-(4-chlorophenyl)-N-((2-(2,6-dioxopiperidin-3-yl)-1-oxoisoindolin-5-yl)methyl)-2,2-difluoroacetamide. In certain embodiments, Compound 1 refers to polymorph Form C of 2-(4-chlorophenyl)-N-((2-(2,6-dioxopiperidin-3-yl)-1-oxoisoindolin-5-yl)methyl)-2,2-difluoroacetamide. In one embodiment, the stereoisomer is an enantiomer.

The term "subject" or "patient" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, "hematological cancer" includes myeloma, lymphoma and leukemia. The terms "hematological cancer" and "hematological malignancy" are used interchangeably herein. In one embodiment, the myeloma is multiple myeloma. In some embodiments, the leukemia is, for example, acute myelogenous or myeloid leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer or hematological malignancy is indolent lymphoma including, for example, DLBCL, follicular lymphoma, or marginal zone lymphoma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to at least one anticancer therapy.

In one embodiment, the subject has leukemia, including, for example, chronic lymphocytic leukemia, chronic myelocytic leukemia, acute lymphoblastic leukemia, acute myeloid leukemia, and acute myeloblastic leukemia. In one embodiment, the subject has chronic lymphocytic leukemia. In one embodiment, the subject chronic myelocytic leukemia. In one embodiment, the subject has acute lymphoblastic leukemia. In one embodiment, the subject has acute myeloid leukemia. In one embodiment, the subject acute myeloblastic leukemia. In one embodiment, the leukemia can be relapsed, refractory or resistant to at least one anticancer therapy. In one embodiment, the leukemia can be relapsed. In one embodiment, the leukemia can be refractory to at least one anticancer therapy. In one embodiment, the leukemia can be resistant to at least one anticancer therapy. In one embodiment, the subject is 18 years or older having relapsed or refractory AML. In one embodiment, the subject is 18 years or older having refractory AML.

In one embodiment, the subject has acute myelogenous or myeloid leukemia (AML), including, for example, the following subtypes of AML. The term "acute myelogenous or myeloid leukemia" refers to hematological conditions characterized by proliferation and accumulation of primarily undifferentiated or minimally differentiated myeloid cells in the bone marrow, and includes subtypes categorized by either the FAB (French, American, British) or WHO classification system. As described herein, the AML includes the following subtypes based on the FAB classification: M0 (AML minimally differentiated); M1 (AML with minimal maturation); M2 (AML with maturation); M3 (Acute promyelocytic leukemia); M4 (Acute myelomonocytic leukemia); M4 (eos Acute myelomonocytic leukemia with eosinophilia); M5 (Acute monocytic leukemia); M6 (Acute erythroid leukemia); and M7 (Acute megakaryoblastic leukemia). As described herein, the AML includes the following subtypes based on the WHO classification: AML with recurrent genetic abnormalities (AML with translocation between chromosomes 8 and 21; AML with translocation or inversion in chromosome 16; AML with translocation between chromosomes 9 and 11; APL (M3) with translocation between chromosomes 15 and 17; AML with translocation between chromosomes 6 and 9; AML with translocation or inversion in chromosome 3); AML (megakaryoblastic) with a translocation between chromosomes 1 and 22; AML with myelodysplasia-related changes; AML related to previous chemotherapy or radiation (Alkylating agent-related AML; Topoisomerase II inhibitor-related AML); AML not otherwise categorized (AML that does not fall into the above categories, i. e. AML minimally differentiated (M0); AML with minimal maturation (M1); AML with maturation (M2); Acute myelomonocytic leukemia (M4); Acute monocytic leukemia (M5); Acute erythroid leukemia (M6); Acute megakaryoblastic leukemia (M7); Acute basophilic leukemia; Acute panmyelosis with fibrosis); Myeloid Sarcoma (also known as granulocytic sarcoma, chloroma or extramedullary myeloblastoma); and Undifferentiated and biphenotypic acute leukemias (also known as mixed phenotype acute leukemias). (see https://www.cancer.org/cancer/acute-myeloid-leukemia/detection-diagnosis-staging/how-classified.html, last accessed May 25, 2017).

In one embodiment, the subject has myelodysplastic syndrome (MDS), including, for example, the following subtypes of MDS. The term "myelodysplastic syndrome" refers to hematological conditions characterized by abnormalities in the production of one or more of the cellular components of blood (red cells, white cells (other than lymphocytes) and platelets (or their progenitor cells, megakaryocytes)), and includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML). The MDS as used herein also includes very low risk, low risk, intermediate risk, high risk and very high risk MDS. In some embodiments, the MDS is primary or de novo MDS. In other embodiments, the MDS is secondary.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease. In one embodiment, the disease is leukemia, including, but not limited to, chronic lymphocytic leukemia, chronic myelocytic leukemia, acute lymphoblastic leukemia, acute myeloid leukemia, and acute myeloblastic leukemia. In one embodiment, the leukemia can be relapsed, refractory or resistant to at least one anticancer therapy. In one embodiment, the disease is AML, including, a subtype of AML discussed above. In one embodiment, the disease is MDS, including, a subtype of MDS discussed above.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment." In one embodiment, the disease is leukemia, including, but is not limited to, chronic lymphocytic leukemia, chronic myelocytic leukemia, acute lymphoblastic leukemia, acute myeloid leukemia, and acute myeloblastic leukemia. In one embodiment, the leukemia can be relapsed, refractory or resistant to at least one anticancer therapy. In one embodiment, the disease is AML, including, a subtype of AML discussed herein. In one embodiment, the disease is MDS, including, a subtype of MDS discussed herein.

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission. In one embodiment, the disease is leukemia, including, but not limited to, chronic lymphocytic leukemia, chronic myelocytic leukemia, acute lymphoblastic leukemia, acute myeloid leukemia, and acute myeloblastic leukemia. In one embodiment, the leukemia can be relapsed, refractory or resistant to at least one anticancer therapy. In one embodiment, the disease is AML, including, a subtype of AML discussed herein. In one embodiment, the disease is MDS, including a subtype of MDS discussed herein.

The term "adverse effect" is used according to its ordinary and common meaning in the art and as used herein can refer to a specific condition associated with treatment, prevention, management, or amelioration of a disease described herein resulting from treatment with a compound or composition described herein. One such adverse effect is the onset of neutropenia. Neutropenia can result from damage to bone marrow, and refers to any condition causing inhibition, elimination, or disruption (directly or indirectly) of neutrophil production and/or maturation.

The term "refractory or resistant" refers to a circumstance where a subject or a mammal, even after intensive treatment, has residual cancer cells in his body.

The term "drug resistance" refers to the condition when a disease does not respond to the treatment of a certain drug or drugs. Drug resistance can be either intrinsic, which means the disease has never been responsive to the particular drug or drugs, or it can be acquired, which means the disease ceases responding to particular a drug or drugs that the disease had previously responded to. In certain embodiments, drug resistance is intrinsic. In certain embodiments, the drug resistance is acquired.

The term "relapsed" refers to a situation where a subject or a mammal, which has had a remission of cancer after therapy has a return of cancer cells.

A "cycling therapy" refers to a regimen or therapy that includes an administration period as described herein and a rest period as described herein.

The term "administration period" as used herein refers to a period of time a subject is continuously or actively administered a compound or composition described herein.

The term "rest period" as used herein refers to a period of time, often following an administration period, where a subject is not administered a compound or composition described herein (e.g. discontinuation of treatment). In certain embodiments, a "rest period" refers to a period of time where a single agent is not administered to a subject or treatment using a particular compound is discontinued. In such embodiments, a second therapeutic agent (e.g., a different agent than the compound or composition administered in the previous administration period) can be administered to the subject.

The term "QD" refers to a once daily dose administration.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, eg, light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

As used herein, Overall survival (OS) means the time from randomization in a clinical trial until death from any cause. Progression-free survival (PFS) means the time from randomization in a clinical trial until progression or death. Event-free survival (EFS) means the time from study entry until any treatment failure, including disease progression, treatment discontinuation for any reason, or death. Overall response rate (ORR) means the sum of the percentage of patients who achieve complete and partial responses. Duration of response (DoR) is the time from achieving a response until relapse or disease progression.

As used herein, "patient population treated with Compound 1" refers to a patient population that has received any treatment with Compound 1.

As used herein, "patient population not treated with Compound 1" refers to a patient population that has not received any treatment with Compound 1. Such patient population includes patients who have not received any treatment for cancer, patients who have been treated with placebo, and patients who have been treated with any cancer therapy, other than treatment with Compound 1.

In leukemia patients, in particular AML patients, response to treatment can be assessed based on the International Working Group Response Criteria in AML (Cheson et al. Revised recommendations of the International Working Group for diagnosis, standardization of response criteria, treatment outcomes, and reporting standards for therapeutic trials in acute myeloid leukemia. *J Clin Oncol* 2003; 21(24): 4642-9).

| Response Criterion | Time of Assessment | Neutrophils (μL) | Platelets (μL) | Bone Marrow Blasts (%) | Other |
|---|---|---|---|---|---|
| Early Treatment assessment | 7-10 days after therapy | NA | NA | <5 | |
| Morphologic Leukemia-free State | Varies by protocol | NA | NA | <5 | Flow cytometry EMD |
| Morphologic CR | Varies by protocol | ≥1,000 | ≥100,000 | <5 | Transfusion EMD |
| Cytogenetic CR (CRc) | Varies by protocol | ≥1,000 | ≥100,000 | <5 | Cytogenetics-normal, EMD |
| Molecular CR (CRm) | Varies by protocol | ≥1,000 | ≥100,000 | <5 | Molecular-negative, EMD |
| Morphologic CR with incomplete blood recovery (CRi) | Varies by protocol | Fulfill all criteria for CR except for residual neutropenia (<1,000/μL) or thrombocytopenia (<100,000/μL). | | | |
| Partial Remission | Varies by protocol | ≥1,000 | ≥100,000 | Decrease ≥50 resulting in 5 to 25 | Blasts ≤5% if Auer rod positive |
| Relapse after CR | Varies by protocol | Reappearance of leukemic blasts in the peripheral blood or ≥5% blasts in the bone marrow not attributable to any other cause (eg, bone marrow regeneration after consolidation therapy). | | | |

Key: AML = acute myelogenous leukemia; CR = complete remission; EMD = extramedullary disease; IWG = International Working Group; NA = not applicable.

As used herein and unless otherwise indicated, the term "pharmaceutically acceptable salt" includes, but is not limited to, a salt of an acidic group. Under certain acidic conditions, the compound can form a wide variety of salts with various inorganic and organic acids. The acids that can be used to prepare pharmaceutically acceptable salts of such basic compounds are those that form salts such as pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate.

As used herein and unless otherwise indicated, the term "hydrate" means a compound provided herein or a salt thereof, further including a stoichiometric or non-stoichiometric amount of water bound by non-covalent intermolecular forces. The hydrates can be crystalline or non-crystalline.

As used herein and unless otherwise indicated, the term "solvate" means a solvate formed from the association of one or more solvent molecules to compound provided herein. The term "solvate" includes hydrates (e.g., monohydrate, dihydrate, trihydrate, tetrahydrate, and the like). The solvates can be crystalline or non-crystalline.

As used herein, and unless otherwise specified, the term "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound includes one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound provided herein is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds provided herein (e.g., R/S=30/70, 35/65, 40/60, 45/55, 55/45, 60/40, 65/35 and 70/30).

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

6.2 Compound

The compound suitable for use in the methods provided herein is Compound 1: 2-(4-chlorophenyl)-N-((2-(2,6-dioxopiperidin-3-yl)-1-oxoisoindolin-5-yl)methyl)-2,2-difluoroacetamide having the structure:

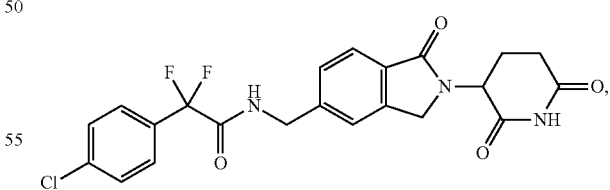

or its stereoisomers or mixture of stereoisomers, isotopologues, pharmaceutically acceptable salts, tautomers, solvates, hydrates, co-crystals, clathrates, or polymorphs thereof. In certain embodiments, Compound 1 refers to 2-(4-chlorophenyl)-N-((2-(2,6-dioxopiperidin-3-yl)-1-oxoisoindolin-5-yl)methyl)-2,2-difluoroacetamide.

Compound 1 can be prepared according to the methods described in the Examples provided herein or as described in U.S. Pat. No. 9,499,514, the disclosure of which is incorporated herein by reference in its entirety. The compound can be also synthesized according to other methods apparent to those of skill in the art based upon the teaching herein.

In certain embodiments, Compound 1 is a solid. In certain embodiments, Compound 1 is hydrated. In certain embodiments, Compound 1 is solvated. In certain embodiments, Compound 1 is anhydrous.

In certain embodiments, Compound 1 is amorphous. In certain embodiments, Compound 1 is crystalline. In certain embodiments, Compound 1 is in a crystalline form described in U.S. Provisional application Ser. No. 15/400,630 filed on Jan. 6, 2017, which is incorporated herein by reference in its entirety. Exemplary solid forms are described on page nos. 86-101.

The solid forms of Compound 1 can be prepared according to the methods described in the disclosure of U.S. application Ser. No. 15/400,630 filed on Jan. 6, 2017. See page nos. 86-101. The solid forms can be also prepared according to other methods apparent to those of skill in the art.

In one embodiment, Compound 1 is polymorph Form A, Form B, Form C, Form D, Form E or an amorphous form of 2-(4-chlorophenyl)-N-((2-(2,6-dioxopiperidin-3-yl)-1-oxoisoindolin-5-yl)methyl)-2,2-difluoroacetamide. Polymorphs of 2-(4-chlorophenyl)-N-((2-(2,6-dioxopiperidin-3-yl)-1-oxoisoindolin-5-yl)methyl)-2,2-difluoroacetamide are briefly described herein.

Form A of 2-(4-chlorophenyl)-N-((2-(2,6-dioxopiperidin-3-yl)-1-oxoisoindolin-5-yl)methyl)-2,2-difluoroacetamide In certain embodiments, the compound for use in the methods is Form A of 2-(4-chlorophenyl)-N-((2-(2,6-dioxopiperidin-3-yl)-1-oxoisoindolin-5-yl)methyl)-2,2-difluoroacetamide.

In one embodiment, Form A is an anhydrous form of 2-(4-chlorophenyl)-N-((2-(2,6-dioxopiperidin-3-yl)-1-oxoisoindolin-5-yl)methyl)-2,2-difluoroacetamide. In another embodiment, Form A of 2-(4-chlorophenyl)-N-((2-(2,6-dioxopiperidin-3-yl)-1-oxoisoindolin-5-yl)methyl)-2,2-difluoroacetamide is crystalline.

In certain embodiments, Form A is obtained by crystallization from certain solvent systems, for example, solvent systems comprising one or more of the following solvents: acetone and the solvent mixture of isopropanol and water at room temperature. In certain embodiments, Form A is obtained as an intermediate solid form from slurries at elevated temperature, for example about 50° C., in ethanol/water (1:1), acetone or acetonitrile.

In certain embodiments, Form A is substantially crystalline, as indicated by, e.g., X-ray powder diffraction measurements. In one embodiment, Form A has an X-ray powder diffraction pattern substantially as shown in FIG. 2.

Figure 2:
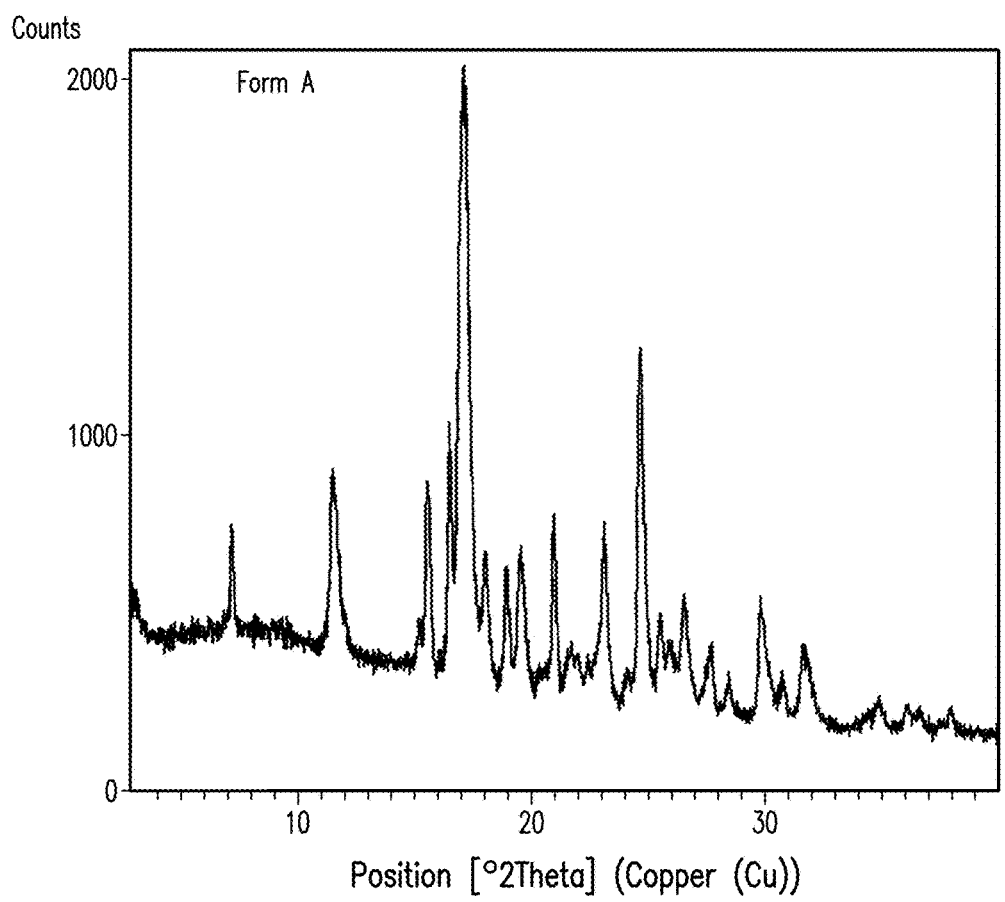
FIG. 2 depicts an X-ray powder diffractogram (XRPD) plot of Form A of Compound 1.

In one embodiment, Form A has one or more characteristic X-ray powder diffraction peaks at a two-theta angle of approximately 11.5, 15.6, 16.6, 17.2, 18.1, 19.0, 19.6, 21.1, 23.2 or 24.8 degrees 2θ as depicted in FIG. 2. In another embodiment, Form A has one, two, three or four characteristic X-ray powder diffraction peaks at a two-theta angle of approximately 15.6, 16.6, 17.2 or 24.8 degrees 2θ. In another embodiment, Form A has one, two, three, four, five, six or seven characteristic X-ray powder diffraction peaks as set forth in Table A. In another embodiment, Form A has one, two, or three characteristic X-ray powder diffraction peaks as set forth in Table A.

TABLE A

| No. | Pos. [°2Th.] | d-spacing [Å] | Rel. Int. [%] |
|---|---|---|---|
| 1 | 7.23 | 12.2187 | 17.6 |
| 2 | 11.52 | 7.6789 | 29.7 |
| 3 | 15.22 | 5.8209 | 7.5 |
| 4 | 15.62 | 5.6720 | 31.2 |
| 5 | 16.58 | 5.3466 | 40.3 |
| 6 | 17.19 | 5.1576 | 100.0 |
| 7 | 18.08 | 4.9056 | 22.3 |
| 8 | 19.00 | 4.6702 | 19.6 |
| 9 | 19.60 | 4.5302 | 22.1 |
| 10 | 21.05 | 4.2197 | 29.2 |
| 11 | 21.74 | 4.0884 | 8.3 |
| 12 | 22.01 | 4.0388 | 7.1 |
| 13 | 22.47 | 3.9576 | 6.0 |
| 14 | 23.22 | 3.8312 | 28.6 |
| 15 | 24.17 | 3.6825 | 5.6 |
| 16 | 24.77 | 3.5945 | 57.2 |
| 17 | 25.59 | 3.4813 | 14.6 |
| 18 | 25.94 | 3.4356 | 10.5 |
| 19 | 26.63 | 3.3470 | 17.4 |
| 20 | 27.73 | 3.2172 | 10.0 |
| 21 | 28.51 | 3.1307 | 7.1 |
| 22 | 29.88 | 2.9906 | 19.3 |
| 23 | 30.76 | 2.9065 | 7.1 |
| 24 | 31.59 | 2.8327 | 11.1 |
| 25 | 34.82 | 2.5766 | 4.8 |
| 26 | 36.05 | 2.4913 | 4.3 |

Figure 3:
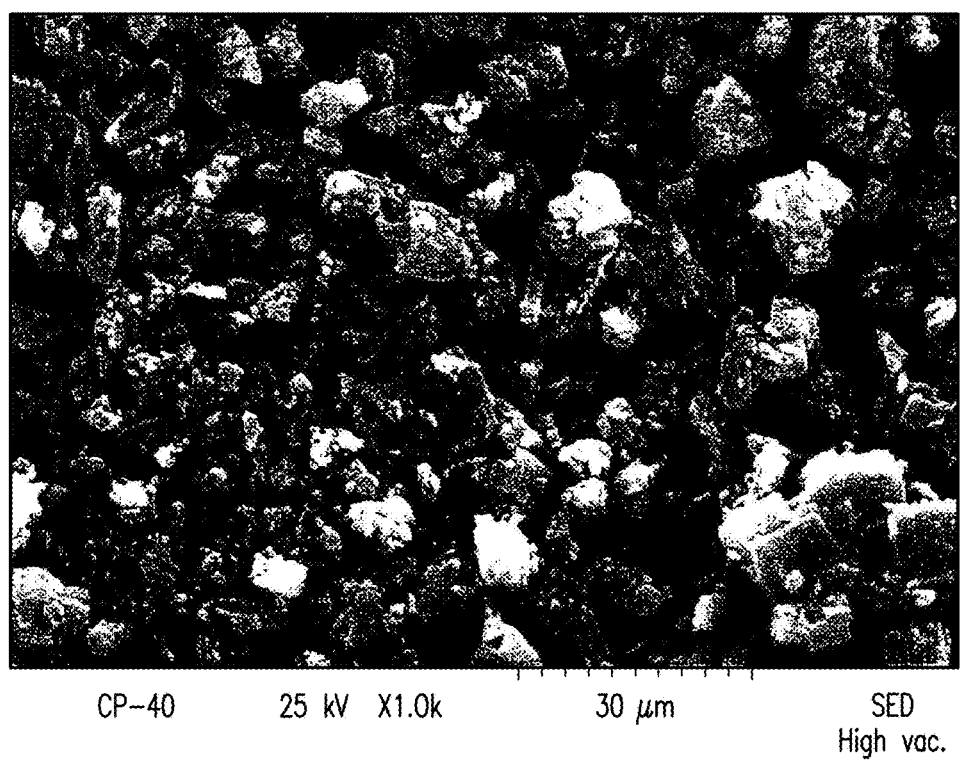
FIG. 3 depicts a SEM image of Form A of Compound 1.

In one embodiment, Form A has the SEM picture as shown in FIG. 3.

Figure 4:
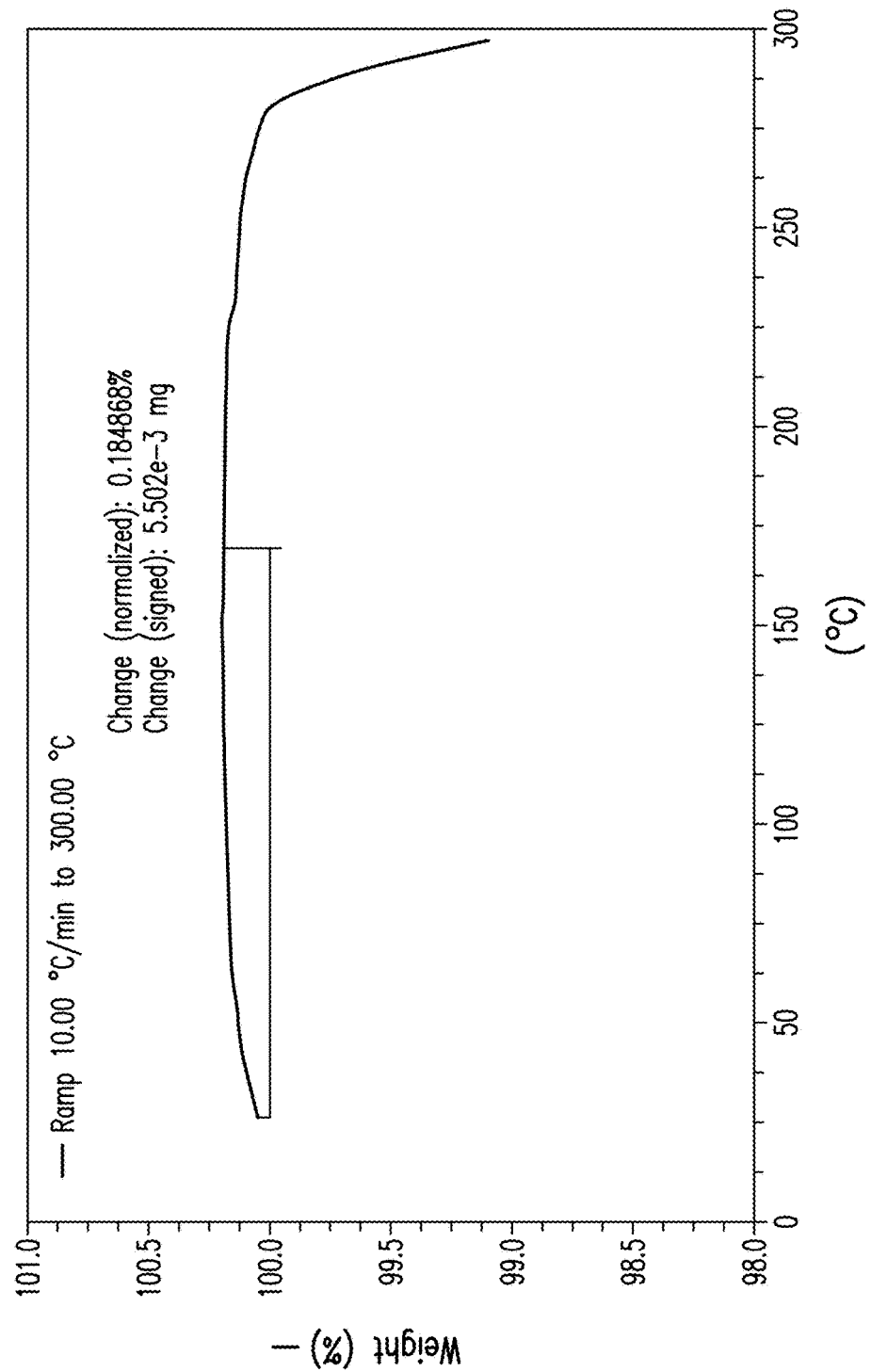
FIG. 4 depicts a thermogravimetrical analysis (TGA) plot of Form A of Compound 1.

In one embodiment, crystalline Form A has a thermogravimetric (TGA) thermograph corresponding substantially to the representative TGA thermogram as depicted in FIG. 4. In certain embodiments, no TGA weight loss is observed for Form A.

Figure 5:
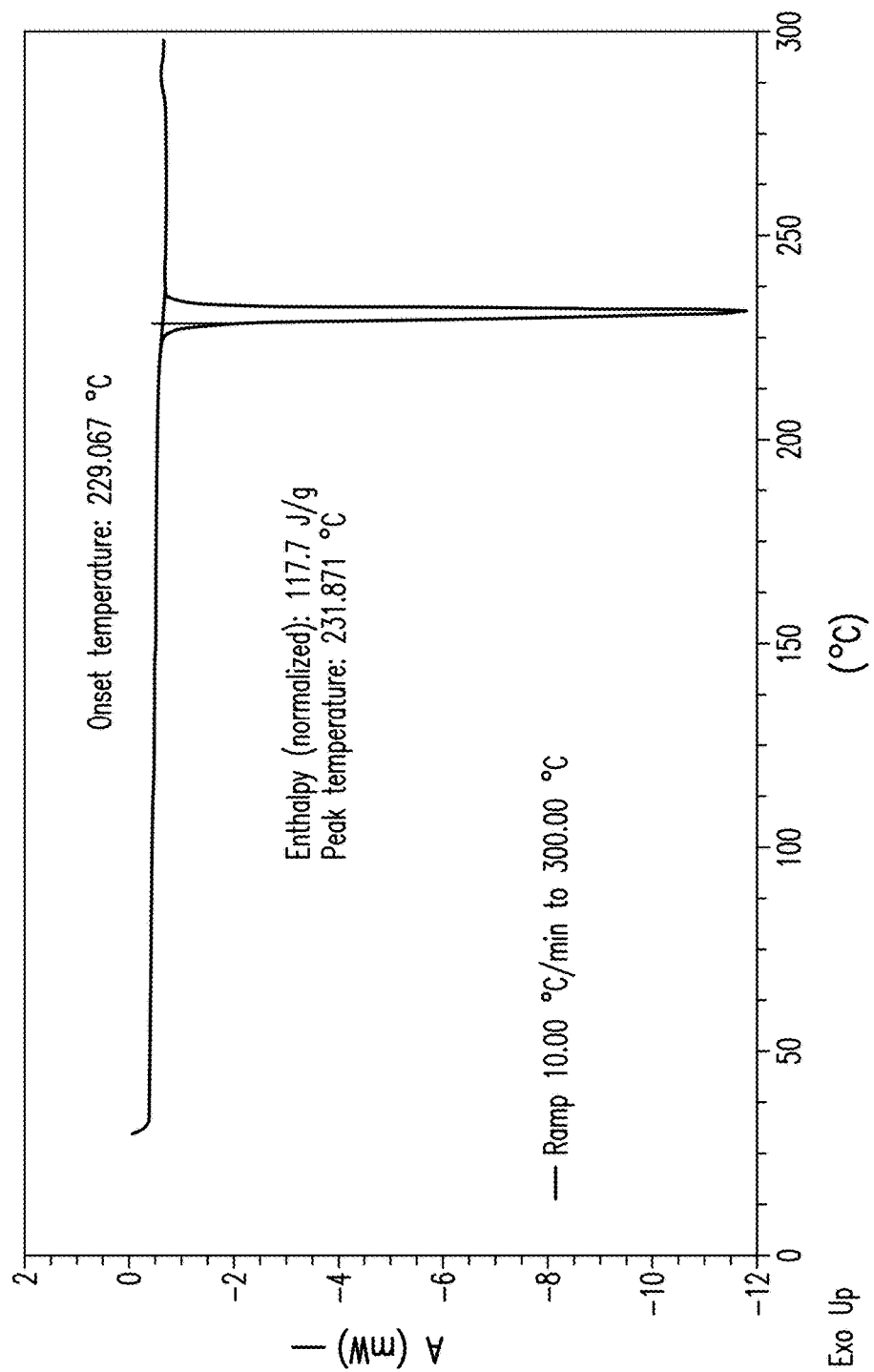
FIG. 5 depicts a differential scanning calorimetry (DSC) thermogram plot of Form A of Compound 1.

In one embodiment, crystalline Form A has a DSC thermogram corresponding substantially as depicted in FIG. 5. In certain embodiments, Form A is characterized by a DSC plot comprising a melting event with an onset temperature of 229° C. and heat of fusion of 118 J/g.

In certain embodiments, Form A is characterized by dynamic vapor sorption analysis. A representative dynamic vapor sorption (DVS) isotherm plot is shown in FIG. 6. In certain embodiments, when the relative humidity ("RH") is increased from about 0% to about 90% RH, Form A exhibits less than 1.5%, less than 1.2% or about 1.2% w/w water uptake. In certain embodiments, Form A comprises less than 0.1% water as determined in a coulometric Karl Fischer (KF) titrator equipped with an oven sample processor set at 225° C.

In certain embodiments, no significant degradation or residual solvent for Form A is observed by $^1$H NMR (FIG. 7).

In certain embodiments, Form A is characterized by its stability profile upon compression. In certain embodiments, Form A is stable, e.g., its XRPD pattern remains substantially unchanged with broader diffraction peaks, upon application of 2000-psi pressure for about 1 minute (FIG. 8).

In still another embodiment, Form A is substantially pure. In certain embodiments, the substantially pure Form A is substantially free of other solid forms, e.g., amorphous form. In certain embodiments, the purity of the substantially pure Form A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments Form A is substantially pure. In certain embodiments herein Form A is substantially free of other solid forms comprising 2-(4-chlorophenyl)-N-((2-(2,6-dioxopiperidin-3-yl)-1-oxoisoindolin-5-yl)methyl)-2,2-difluoroacetamide including, e.g., Forms B, C, D, E and/or an amorphous solid form comprising 2-(4-chlorophenyl)-N-((2-(2,6-dioxopiperidin-3-yl)-1-oxoisoindolin-5-yl)methyl)-2,2-difluoroacetamide. In certain embodiments, Form A is a mixture of solid forms comprising 2-(4-chlorophenyl)-N-((2-(2,6-dioxopiperidin-3-yl)-1-oxoisoindolin-5-yl)methyl)-2,2-difluoroacetamide, including, e.g., a mixture comprising one or more of the following: Forms B, C, D, E and an amorphous solid form comprising 2-(4-chlorophenyl)-N-((2-(2,6-dioxopiperidin-3-yl)-1-oxoisoindolin-5-yl)methyl)-2,2-difluoroacetamide.

Form B of 2-(4-chlorophenyl)-N-((2-(2,6-dioxopiperidin-3-yl)-1-oxoisoindolin-5-yl)methyl)-2,2-difluoroacetamide In certain embodiments, the compound for use in the methods is anhydrous Form B of 2-(4-chlorophenyl)-N-((2-(2,6-dioxopiperidin-3-yl)-1-oxoisoindolin-5-yl)methyl)-2,2-difluoroacetamide.

In certain embodiments, Form B is obtained by anti-solvent recrystallization from certain solvent systems, for example, solvent systems comprising one or more of the following solvents: methanol/water, DMSO/isopropanol, DMSO/toluene, and DMSO/water. In certain embodiments, Form B is obtained by cooling recrystallization from THF/water (1:1).

In certain embodiments, Form B is crystalline, as indicated by, e.g., X-ray powder diffraction measurements. In one embodiment, Form B has an X-ray powder diffraction pattern substantially as shown in FIG. 9.

In one embodiment, Form B has one or more characteristic X-ray powder diffraction peaks at a two-theta angle of approximately 15.4, 16.3, 16.7, 17.7, 20.4, 25.6 or 27.5, degrees 2θ as depicted in FIG. 9. In another embodiment, Form B has one, two, three or four characteristic X-ray powder diffraction peaks at a two-theta angle of approximately 16.7, 25.6, 15.4 or 16.3 degrees 2θ. In another embodiment, Form B has one, two, three, four, five, six or seven characteristic X-ray powder diffraction peaks as set forth in Table B. In another embodiment, Form B has one, two, or three characteristic X-ray powder diffraction peaks as set forth in Table B.

TABLE B

| X-Ray Diffraction Peaks for Form B of Compound 1 | | | |
|---|---|---|---|
| No. | Pos. [°2Th.] | d-spacing [Å] | Rel. Int. [%] |
| 1 | 7.01 | 12.6035 | 9.3 |
| 2 | 11.58 | 7.6444 | 8.3 |
| 3 | 11.80 | 7.5027 | 6.8 |
| 4 | 12.73 | 6.9551 | 18.4 |
| 5 | 15.38 | 5.7601 | 34.8 |
| 6 | 16.32 | 5.4330 | 31.4 |
| 7 | 16.72 | 5.3012 | 100.0 |
| 8 | 17.72 | 5.0046 | 26.6 |
| 9 | 18.13 | 4.8930 | 19.8 |
| 10 | 18.77 | 4.7271 | 7.5 |
| 11 | 20.41 | 4.3516 | 22.0 |
| 12 | 21.02 | 4.2258 | 15.9 |
| 13 | 21.21 | 4.1881 | 13.5 |
| 14 | 21.93 | 4.0529 | 3.4 |
| 15 | 23.68 | 3.7581 | 14.2 |
| 16 | 25.01 | 3.5601 | 10.4 |
| 17 | 25.63 | 3.4755 | 37.3 |
| 18 | 26.19 | 3.4030 | 9.8 |
| 19 | 26.73 | 3.3349 | 8.5 |
| 20 | 27.45 | 3.2499 | 20.9 |
| 21 | 27.71 | 3.2193 | 9.4 |
| 22 | 28.22 | 3.1623 | 11.8 |
| 23 | 29.48 | 3.0296 | 4.7 |
| 24 | 30.10 | 2.9692 | 15.0 |
| 25 | 31.08 | 2.8775 | 18.3 |
| 26 | 31.65 | 2.8272 | 6.2 |
| 27 | 34.29 | 2.6150 | 3.4 |

In one embodiment, Form B has the SEM picture as shown in FIG. 10. In one embodiment, Form B has a thermogravimetric (TGA) thermograph corresponding substantially to the representative TGA thermogram as depicted in FIG. 11. In certain embodiments, Form B shows no TGA weight loss below 170° C. In certain embodiments, Form B shows a TGA weight loss of 0.4% between 170~230° C.

In one embodiment, crystalline Form B has a DSC thermogram corresponding substantially as depicted in FIG. 12. In certain embodiments, Form B is characterized by a DSC plot comprising a melt/recrystallization event at 219~224° C. and a major melting event with a peak temperature of 231° C.

In certain embodiments, Form B is characterized by dynamic vapor sorption analysis. A representative dynamic vapor sorption (DVS) isotherm plot is shown in FIG. 13. In certain embodiments, when the relative humidity ("RH") is increased from about 0% to about 90% RH, Form B exhibits about 1.4% w/w water uptake. In certain embodiments, Form B comprises less than 0.1% water as determined in a coulometric Karl Fischer (KF) titrator equipped with an oven sample processor set at 225° C.

In certain embodiments, Form B shows no significant degradation or residual solvent by $^1$H NMR (FIG. 14).

In certain embodiments, Form B is characterized by its stability profile upon compression. In certain embodiments, Form B is stable, e.g., its XRPD pattern remains substantially unchanged with broader diffraction peaks, upon application of 2000-psi pressure for about 1 minute (FIG. 15).

In still another embodiment, Form B is substantially pure. In certain embodiments, the substantially pure Form B is substantially free of other solid forms, e.g., amorphous form. In certain embodiments, the purity of the substantially pure Form B of is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments, Form B is substantially pure. In certain embodiments, Form B is substantially free of other solid forms comprising 2-(4-chlorophenyl)-N-((2-(2,6-dioxopiperidin-3-yl)-1-oxoisoindolin-5-yl)methyl)-2,2-difluoroacetamide including, e.g., Forms A, C, D, E, and/or an amorphous solid form comprising 2-(4-chlorophenyl)-N-((2-(2,6-dioxopiperidin-3-yl)-1-oxoisoindolin-5-yl)methyl)-2,2-difluoroacetamide. In certain embodiments, Form B is a mixture of solid forms comprising 2-(4-chlorophenyl)-N-((2-(2,6-dioxopiperidin-3-yl)-1-oxoisoindolin-5-yl)methyl)-2,2-difluoroacetamide, including, e.g., a mixture comprising one or more of the following: Forms A, C, D, E, and an amorphous solid form comprising 2-(4-chlorophenyl)-N-((2-(2,6-dioxopiperidin-3-yl)-1-oxoisoindolin-5-yl)methyl)-2,2-difluoroacetamide.

Form C of 2-(4-chlorophenyl)-N-((2-(2,6-dioxopiperidin-3-yl)-1-oxoisoindolin-5-yl)methyl)-2,2-difluoroacetamide In certain embodiments, the compound for use in the methods is an anhydrous Form C of 2-(4-chlorophenyl)-N-((2-(2,6-dioxopiperidin-3-yl)-1-oxoisoindolin-5-yl)methyl)-2,2-difluoroacetamide. In certain embodiments, Form C is the most thermodynamically stable anhydrate among the crystal forms of 2-(4-chlorophenyl)-N-((2-(2,6-dioxopiperidin-3-yl)-1-oxoisoindolin-5-yl)methyl)-2,2-difluoroacetamide.

In certain embodiments, Form C is obtained by slurrying 2-(4-chlorophenyl)-N-((2-(2,6-dioxopiperidin-3-yl)-1-oxoisoindolin-5-yl)methyl)-2,2-difluoroacetamide in certain solvent systems, for example, solvent systems comprising one or more of the following solvents: acetonitril/water, acetone, or ethanol/water for extended period of time.

In certain embodiments, Form C is crystalline, as indicated by, e.g., X-ray powder diffraction measurements. In one embodiment, Form C has an X-ray powder diffraction pattern substantially as shown in FIG. 16.

In one embodiment, Form C has one or more characteristic X-ray powder diffraction peaks at a two-theta angle of approximately 7.4, 11.5, 15.8, 16.7, 16.9, 17.7, 18.4, 19.2, 19.5, 21.1, 23.4, 24.7, or 29.9, degrees 2θ as depicted in FIG. 16. In another embodiment, Form C has one, two, three or four characteristic X-ray powder diffraction peaks at a two-theta angle of approximately 16.7, 16.9, 17.7 or 24.7 degrees 2θ. In another embodiment, Form C has one, two, three, four, five, six or seven characteristic X-ray powder diffraction peaks as set forth in Table C. In another embodiment, Form C has one, two, or three characteristic X-ray powder diffraction peaks as set forth in Table C.

TABLE C

X-Ray Diffraction Peaks for Form C of Compound 1

| No. | Pos. [°2Th.] | d-spacing [Å] | Rel. Int. [%] |
|---|---|---|---|
| 1 | 7.36 | 12.0091 | 32.0 |
| 2 | 9.14 | 9.6750 | 8.3 |
| 3 | 11.51 | 7.6855 | 44.7 |
| 4 | 12.22 | 7.2420 | 4.9 |
| 5 | 15.17 | 5.8398 | 8.4 |
| 6 | 15.82 | 5.6011 | 31.8 |
| 7 | 16.68 | 5.3140 | 57.1 |
| 8 | 16.92 | 5.2392 | 86.8 |
| 9 | 17.72 | 5.0057 | 100.0 |
| 10 | 18.39 | 4.8242 | 21.9 |
| 11 | 19.18 | 4.6268 | 36.4 |
| 12 | 19.45 | 4.5649 | 27.1 |
| 13 | 21.11 | 4.2077 | 40.4 |
| 14 | 21.82 | 4.0724 | 12.4 |
| 15 | 22.28 | 3.9902 | 12.0 |
| 16 | 22.57 | 3.9398 | 17.6 |
| 17 | 23.36 | 3.8082 | 24.7 |
| 18 | 24.26 | 3.6695 | 7.1 |
| 19 | 24.71 | 3.6026 | 72.5 |
| 20 | 25.74 | 3.4615 | 16.9 |
| 21 | 26.03 | 3.4231 | 9.7 |
| 22 | 26.51 | 3.3627 | 17.7 |
| 23 | 27.88 | 3.1998 | 18.0 |
| 24 | 28.70 | 3.1104 | 6.9 |
| 25 | 29.91 | 2.9871 | 30.5 |
| 26 | 30.43 | 2.9375 | 10.7 |
| 27 | 30.83 | 2.9006 | 5.8 |
| 28 | 32.01 | 2.7960 | 16.6 |
| 29 | 37.94 | 2.3718 | 5.5 |

In one embodiment, Form C has the SEM picture as shown in FIG. 17. In one embodiment, Form C has a thermogravimetric (TGA) thermograph corresponding substantially to the representative TGA thermogram as depicted in FIG. 18. In certain embodiments, Form C shows no TGA weight loss.

In one embodiment, crystalline Form C has a DSC thermogram corresponding substantially as depicted in FIG. 19. In certain embodiments, Form C is characterized by a DSC plot comprising melting event with an onset temperature of 232° C. and heat of fusion of 126 J/g.

In certain embodiments, Form C is characterized by dynamic vapor sorption analysis. A representative dynamic vapor sorption (DVS) isotherm plot is shown in FIG. 20. In certain embodiments, when the relative humidity ("RH") is increased from about 0% to about 90% RH, Form C exhibits about 0.6% w/w water uptake. In certain embodiments, Form C comprises less than 0.1% water as determined in a coulometric Karl Fischer (KF) titrator equipped with an oven sample processor set at 225° C.

In certain embodiments, Form C shows no significant degradation or residual solvent by $^1$H NMR (FIG. 21).

In certain embodiments, Form C is characterized by its stability profile upon compression. In certain embodiments, Form C is stable, e.g., its XRPD pattern remains substantially unchanged with broader diffraction peaks, upon application of 2000-psi pressure for about 1 minute (FIG. 22).

In still another embodiment, Form C is substantially pure. In certain embodiments, the substantially pure Form C is substantially free of other solid forms, e.g., amorphous form. In certain embodiments, the purity of the substantially pure Form C is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, Form C is substantially pure. In certain embodiments, Form C is substantially free of other solid forms comprising 2-(4-chlorophenyl)-N-((2-(2,6-dioxopiperidin-3-yl)-1-oxoisoindolin-5-yl)methyl)-2,2-difluoroacetamide including, e.g., Forms A, B, D, E, and/or an amorphous solid form comprising 2-(4-chlorophenyl)-N-((2-(2,6-dioxopiperidin-3-yl)-1-oxoisoindolin-5-yl)methyl)-2,2-difluoroacetamide. In certain embodiments, Form C is a mixture of solid forms comprising 2-(4-chlorophenyl)-N-((2-(2,6-dioxopiperidin-3-yl)-1-oxoisoindolin-5-yl)methyl)-2,2-difluoroacetamide, including, e.g., a mixture comprising one or more of the following: Forms A, B, D, E, and an amorphous solid form comprising 2-(4-chlorophenyl)-N-((2-(2,6-dioxopiperidin-3-yl)-1-oxoisoindolin-5-yl)methyl)-2,2-difluoroacetamide.

Form D of 2-(4-chlorophenyl)-N-((2-(2,6-dioxopiperidin-3-yl)-1-oxoisoindolin-5-yl)methyl)-2,2-difluoroacetamide In certain embodiments, the compound for use in the methods is Form D of 2-(4-chlorophenyl)-N-((2-(2,6-dioxopiperidin-3-yl)-1-oxoisoindolin-5-yl)methyl)-2,2-difluoroacetamide. In certain embodiments, Form D of 2-(4-chlorophenyl)-N-((2-(2,6-dioxopiperidin-3-yl)-1-oxoisoindolin-5-yl)methyl)-2,2-difluoroacetamide is a DMSO solvate.

In certain embodiments, Form D is obtained by heating Form B in DMSO/methyl isobutyl ketone and cooling the solution.

In certain embodiments, Form D is crystalline, as indicated by, e.g., X-ray powder diffraction measurements. In one embodiment, Form D has an X-ray powder diffraction pattern substantially as shown in FIG. 23.

In one embodiment, Form D has one or more characteristic X-ray powder diffraction peaks at a two-theta angle of approximately 14.1, 14.3, 18.8, 19.1, 23.6 or 24.0 degrees 2θ as depicted in FIG. 23. In another embodiment, Form D has one, two, three or four characteristic X-ray powder diffraction peaks at a two-theta angle of approximately 14.1, 14.3, 18.8 or 19.1 degrees 2θ. In another embodiment, Form D has one, two, three, four, five, six or seven characteristic X-ray powder diffraction peaks as set forth in Table D. In another embodiment, Form D has one, two, or three characteristic X-ray powder diffraction peaks as set forth in Table D.

TABLE D

X-Ray Diffraction Peaks for Form D of Compound 1

| No. | Pos. [°2Th.] | d-spacing [Å] | Rel. Int. [%] |
|---|---|---|---|
| 1 | 4.77 | 18.5435 | 3.0 |
| 2 | 9.57 | 9.2399 | 7.0 |
| 3 | 10.55 | 8.3876 | 3.1 |
| 4 | 11.95 | 7.4070 | 3.7 |
| 5 | 12.50 | 7.0808 | 3.5 |
| 6 | 14.06 | 6.2990 | 100.0 |
| 7 | 14.30 | 6.1927 | 92.9 |
| 8 | 16.13 | 5.4943 | 3.8 |
| 9 | 17.02 | 5.2097 | 8.4 |
| 10 | 17.50 | 5.0676 | 19.8 |
| 11 | 17.78 | 4.9881 | 8.0 |
| 12 | 18.09 | 4.9049 | 7.7 |
| 13 | 18.27 | 4.8561 | 9.0 |
| 14 | 18.75 | 4.7326 | 58.5 |
| 15 | 19.09 | 4.6482 | 63.5 |
| 16 | 21.04 | 4.2228 | 7.3 |
| 17 | 22.77 | 3.9053 | 10.9 |
| 18 | 23.58 | 3.7738 | 53.6 |
| 19 | 24.02 | 3.7045 | 24.6 |
| 20 | 24.90 | 3.5756 | 8.4 |
| 21 | 25.22 | 3.5310 | 10.0 |
| 22 | 26.37 | 3.3796 | 9.4 |
| 23 | 26.63 | 3.3470 | 7.9 |
| 24 | 28.21 | 3.1640 | 5.8 |
| 25 | 29.82 | 2.9958 | 3.0 |
| 26 | 30.16 | 2.9629 | 5.0 |
| 27 | 30.45 | 2.9361 | 6.7 |
| 28 | 32.48 | 2.7566 | 3.3 |
| 29 | 33.03 | 2.7120 | 8.1 |
| 30 | 33.69 | 2.6604 | 3.4 |
| 31 | 35.32 | 2.5413 | 3.0 |
| 32 | 37.96 | 2.3702 | 3.2 |
| 33 | 38.70 | 2.3269 | 3.0 |

In one embodiment, provided herein is Form D having a thermogravimetric (TGA) thermograph corresponding substantially to the representative TGA thermogram as depicted in FIG. 24. In certain embodiments, Form D shows TGA weight loss of about 14.1% up to 140° C.

In certain embodiments, Form D comprises DMSO in about 14.3 wt % as measured by gas chromatography.

In still another embodiment, Form D is substantially pure. In certain embodiments, the substantially pure Form D is substantially free of other solid forms, e.g., amorphous form.

In certain embodiments, the purity of the substantially pure Form D is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments Form D is substantially pure. In certain embodiments, Form D is substantially free of other solid forms comprising 2-(4-chlorophenyl)-N-((2-(2,6-dioxopiperidin-3-yl)-1-oxoisoindolin-5-yl)methyl)-2,2-difluoroacetamide including, e.g., Forms A, B, C, E, and/or an amorphous solid form comprising 2-(4-chlorophenyl)-N-((2-(2,6-dioxopiperidin-3-yl)-1-oxoisoindolin-5-yl)methyl)-2,2-difluoroacetamide as provided herein. In certain embodiments, Form D is a mixture of solid forms comprising 2-(4-chlorophenyl)-N-((2-(2,6-dioxopiperidin-3-yl)-1-oxoisoindolin-5-yl)methyl)-2,2-difluoroacetamide, including, e.g., a mixture comprising one or more of the following: Forms A, B, C, E, and an amorphous solid form comprising 2-(4-chlorophenyl)-N-((2-(2,6-dioxopiperidin-3-yl)-1-oxoisoindolin-5-yl)methyl)-2,2-difluoroacetamide.

Form E of 2-(4-chlorophenyl)-N-((2-(2,6-dioxopiperidin-3-yl)-1-oxoisoindolin-5-yl)methyl)-2,2-difluoroacetamide In certain embodiments, the compound for use in the methods is Form E of 2-(4-chlorophenyl)-N-((2-(2,6-dioxopiperidin-3-yl)-1-oxoisoindolin-5-yl)methyl)-2,2-difluoroacetamide. In certain embodiments, Form E of 2-(4-chlorophenyl)-N-((2-(2,6-dioxopiperidin-3-yl)-1-oxoisoindolin-5-yl)methyl)-2,2-difluoroacetamide is a DMSO solvate.

In certain embodiments, Form E is obtained from Form C in DMSO/MIBK or DMSO/IPA or DMSO/anisole at room temperature.

In certain embodiments, Form E is crystalline, as indicated by, e.g., X-ray powder diffraction measurements. In one embodiment, Form E has an X-ray powder diffraction pattern substantially as shown in FIG. 25.

In one embodiment, Form E has one or more characteristic X-ray powder diffraction peaks at a two-theta angle of approximately 10.5, 12.5, 16.1, 17.0, 18.5, 21.2, 21.7, 22.6, 22.9, 23.4, 23.8, 24.1, 25.1 or 26.7, degrees 2θ as depicted in FIG. 25. In another embodiment, Form E has one, two, three or four characteristic X-ray powder diffraction peaks at a two-theta angle of approximately 16.1, 17.0, 21.2 or 22.9 degrees 2θ. In another embodiment, Form E has one, two, three, four, five, six or seven characteristic X-ray powder diffraction peaks as set forth in Table E. In another embodiment, Form E has one, two, or three characteristic X-ray powder diffraction peaks as set forth in Table E.

TABLE E

X-Ray Diffraction Peaks for Form E of Compound 1

| No. | Pos. [°2Th.] | d-spacing [Å] | Rel. Int. [%] |
|---|---|---|---|
| 1 | 4.20 | 21.0329 | 9.6 |
| 2 | 10.48 | 8.4394 | 32.0 |
| 3 | 12.54 | 7.0591 | 28.4 |
| 4 | 14.52 | 6.1023 | 9.9 |
| 5 | 15.51 | 5.7131 | 17.7 |
| 6 | 16.08 | 5.5121 | 100.0 |
| 7 | 16.97 | 5.2256 | 94.5 |
| 8 | 17.77 | 4.9908 | 17.1 |
| 9 | 18.48 | 4.8001 | 20.5 |
| 10 | 19.54 | 4.5422 | 14.7 |

TABLE E-continued

X-Ray Diffraction Peaks for Form E of Compound 1

| No. | Pos. [°2Th.] | d-spacing [Å] | Rel. Int. [%] |
|---|---|---|---|
| 11 | 21.15 | 4.2007 | 62.8 |
| 12 | 21.72 | 4.0924 | 20.8 |
| 13 | 22.64 | 3.9270 | 57.4 |
| 14 | 22.91 | 3.8826 | 59.9 |
| 15 | 23.43 | 3.7977 | 23.6 |
| 16 | 23.83 | 3.7348 | 23.2 |
| 17 | 24.13 | 3.6881 | 29.5 |
| 18 | 25.14 | 3.5421 | 35.2 |
| 19 | 26.72 | 3.3362 | 49.5 |
| 20 | 27.68 | 3.2232 | 14.6 |
| 21 | 27.93 | 3.1949 | 15.3 |
| 22 | 28.86 | 3.0942 | 15.6 |
| 23 | 29.08 | 3.0703 | 18.3 |
| 24 | 30.12 | 2.9671 | 7.1 |
| 25 | 30.92 | 2.8923 | 12.8 |
| 26 | 32.35 | 2.7672 | 5.0 |
| 27 | 33.21 | 2.6979 | 6.9 |

In one embodiment, provided herein is Form E having a thermogravimetric (TGA) thermograph corresponding substantially to the representative TGA thermogram as depicted in FIG. 26. In certain embodiments, Form E shows TGA weight loss of about 19.4% up to 120° C. In certain embodiments, Form E shows additional weight loss of 24.9% between 120 and 220° C.

In one embodiment, Form E is substantially pure. In certain embodiments, the substantially pure Form E is substantially free of other solid forms, e.g., amorphous form. In certain embodiments, the purity of the substantially pure Form E is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, Form E is substantially pure. In certain embodiments herein, Form E is substantially free of other solid forms comprising 2-(4-chlorophenyl)-N-((2-(2,6-dioxopiperidin-3-yl)-1-oxoisoindolin-5-yl)methyl)-2,2-difluoroacetamide including, e.g., Forms A, B, C, D and/or an amorphous solid form comprising 2-(4-chlorophenyl)-N-((2-(2,6-dioxopiperidin-3-yl)-1-oxoisoindolin-5-yl)methyl)-2,2-difluoroacetamide. In certain embodiments, Form E is a mixture of solid forms comprising 2-(4-chlorophenyl)-N-((2-(2,6-dioxopiperidin-3-yl)-1-oxoisoindolin-5-yl)methyl)-2,2-difluoroacetamide, including, e.g., a mixture comprising one or more of the following: Forms A, B, C, D and an amorphous solid form comprising 2-(4-chlorophenyl)-N-((2-(2,6-dioxopiperidin-3-yl)-1-oxoisoindolin-5-yl)methyl)-2,2-difluoroacetamide.

Amorphous Form of 2-(4-chlorophenyl)-N-((2-(2,6-dioxopiperidin-3-yl)-1-oxoisoindolin-5-yl)methyl)-2,2-difluoroacetamide In certain embodiments, the compound for use in the methods is amorphous 2-(4-chlorophenyl)-N-((2-(2,6-dioxopiperidin-3-yl)-1-oxoisoindolin-5-yl)methyl)-2,2-difluoroacetamide.

In certain embodiments, provided herein are methods for making the amorphous form by heating 2-(4-chlorophenyl)-N-((2-(2,6-dioxopiperidin-3-yl)-1-oxoisoindolin-5-yl)methyl)-2,2-difluoroacetamide in THF and water and cooling the solution.

In one embodiment, provided herein is an amorphous solid form having a modulated DSC thermogram as depicted in FIG. 27.

In one embodiment, amorphous 2-(4-chlorophenyl)-N-((2-(2,6-dioxopiperidin-3-yl)-1-oxoisoindolin-5-yl)methyl)-2,2-difluoroacetamide has an X-ray powder diffraction pattern substantially as shown in FIG. 28.

In one embodiment, amorphous 2-(4-chlorophenyl)-N-((2-(2,6-dioxopiperidin-3-yl)-1-oxoisoindolin-5-yl)methyl)-2,2-difluoroacetamide has a $^1$H NMR spectrum substantially as shown in FIG. 29.

In still another embodiment, amorphous 2-(4-chlorophenyl)-N-((2-(2,6-dioxopiperidin-3-yl)-1-oxoisoindolin-5-yl)methyl)-2,2-difluoroacetamide is substantially pure. In certain embodiments, the substantially pure amorphous 2-(4-chlorophenyl)-N-((2-(2,6-dioxopiperidin-3-yl)-1-oxoisoindolin-5-yl)methyl)-2,2-difluoroacetamide is substantially free of any crystalline solid forms, e.g., Form A, Form B, Form C, Form D or Form E. In certain embodiments, the purity of the substantially pure amorphous 2-(4-chlorophenyl)-N-((2-(2,6-dioxopiperidin-3-yl)-1-oxoisoindolin-5-yl)methyl)-2,2-difluoroacetamide is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Isotopologues of 2-(4-chlorophenyl)-N-((2-(2,6-dioxopiperidin-3-yl)-1-oxoisoindolin-5-yl)methyl)-2,2-difluoroacetamide Also provided herein are isotopically enriched analogs of 2-(4-chlorophenyl)-N-((2-(2,6-dioxopiperidin-3-yl)-1-oxoisoindolin-5-yl)methyl)-2,2-difluoroacetamide ("isotopologues") provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

6.3 Methods of Use

In one embodiment, provided herein are methods of treating, preventing, managing, and/or ameliorating hematological cancer or hematological malignancy by administering Compound 1 to a subject. In some embodiments, the hematological cancer or hematological malignancy is myeloma, lymphoma or leukemia. In certain embodiments, the hematological cancer or hematological malignancy is myeloma. In certain embodiments, the hematological cancer or hematological malignancy is lymphoma. In certain embodiments, the hematological cancer or hematological malignancy is leukemia.

In one embodiment, the hematological cancer is multiple myeloma (MM). In one embodiment, the hematological cancer is relapsed/refractory (R/R) multiple myeloma. In one embodiment, the patient having R/R multiple myeloma has impaired renal function.

In one embodiment, the hematological cancer is acute myelogenous leukemia (AML). In one embodiment, the hematological cancer is acute lymphocytic leukemia (ALL). In one embodiment, the hematological cancer is adult T-cell leukemia. In one embodiment, the hematological cancer is chronic lymphocytic leukemia (CLL). In one embodiment, the hematological cancer is hairy cell leukemia. In one embodiment, the hematological cancer is myelodysplasia. In one embodiment, the hematological cancer is myeloproliferative disorders. In one embodiment, the hematological cancer is chronic myelogenous leukemia (CML). In one embodiment, the hematological cancer is myelodysplastic syndrome (MDS). In one embodiment, the hematological cancer is, human lymphotropic virus-type 1 (HTLV-1) leukemia. In one embodiment, the hematological cancer is mastocytosis. In one embodiment, the hematological cancer is B-cell acute lymphoblastic leukemia. In one embodiment, the hematological cancer is CLL.

In one embodiment, the hematological cancer is diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is HL. In one embodiment, the hematological cancer is NHL. In one embodiment, the hematological cancer is indolent lymphoma including, for example, DLBCL, follicular lymphoma, or marginal zone lymphoma.

In certain embodiments, the hematological cancer is drug resistant to at least one anticancer therapy. In certain embodiments the hematological cancer is relapsed or refractory to at least one anticancer therapy. In certain embodiments, the hematological cancer is metastatic.

In one embodiment, provided herein are methods of treating, preventing, managing, and/or ameliorating leukemia by administering a therapeutically active amount of Compound 1 to a subject. In one embodiment, the leukemia is acute myeloid leukemia (AML). In one embodiment, the AML is relapsed or refractory AML. In one embodiment, the AML is newly diagnosed AML. In another embodiment, the AML has FAB classification M0/1. In another embodiment, the AML has FAB classification M2. In another embodiment, the AML has FAB classification M3. In another embodiment, the AML has FAB classification M4. In another embodiment, the AML has FAB classification M5. In one embodiment, the AML is AML with at least one recurrent genetic abnormality (for example, AML with translocation between chromosomes 8 and 21; AML with translocation or inversion in chromosome 16; AML with translocation between chromosomes 9 and 11; APL (M3) with translocation between chromosomes 15 and 17; AML with translocation between chromosomes 6 and 9; AML with translocation or inversion in chromosome 3); AML (megakaryoblastic) with a translocation between chromosomes 1 and 22; AML with myelodysplasia-related changes; AML related to previous chemotherapy or radiation (for example, alkylating agent-related AML; or Topoisomerase II inhibitor-related AML); AML not otherwise categorized (for example, AML that does not fall into the above categories, i. e. AML minimally differentiated (M0); AML with minimal maturation (M1); AML with maturation (M2); Acute myelomonocytic leukemia (M4); Acute monocytic leukemia (M5); Acute erythroid leukemia (M6); Acute megakaryoblastic leukemia (M7); Acute basophilic leukemia; or Acute panmyelosis with fibrosis); Myeloid Sarcoma (also known as granulocytic sarcoma, chloroma or extramedullary myeloblastoma); or Undifferentiated and biphenotypic acute leukemias (also known as mixed phenotype acute leukemias).

In one embodiment, provided herein are methods of treating, preventing, managing, and/or ameliorating a myelodysplastic syndrome (MDS) by administering a therapeutically active amount of Compound 1 to a subject. In one embodiment provided herein is a method of treating MDS. In one embodiment, the MDS is relapsed, resistant or refractory MDS. In one embodiment, MDS is refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms or chronic myelomonocytic leukemia (CMML). In some embodiments, the MDS is very low risk, low risk, intermediate risk, high risk or very high risk MDS. In one embodiment, the MDS is very low risk. In another embodiment, the MDS is low risk. In another embodiment, the MDS is intermediate risk. In another embodiment, the MDS is high risk. In another embodiment, the MDS is very high risk MDS. In some embodiments, the MDS is primary or de novo MDS. In other embodiments, the MDS is secondary MDS.

In one embodiment, provided herein are methods of treating, preventing, managing, and/or ameliorating AML by administering Compound 1 to a subject in a dose of about 0.1 mg to about 20 mg. In one embodiment, provided herein are methods of treating, preventing, managing, and/or ameliorating relapsed or refractory AML by administering Compound 1 to a subject in a dose of about 0.1 mg to about 20 mg. In one embodiment, provided herein are methods of treating AML by administering Compound 1 to a subject in a dose of about 0.1 mg to about 20 mg. In one embodiment, provided herein are methods of treating relapsed or refractory AML by administering Compound 1 to a subject in a dose of about 0.1 mg to about 20 mg. In one embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on days 1 to 5, 1 to 10, 1 to 21, or 1 to 28, of a 28 day cycle. In one embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on days 1 to 5, 1 to 10, 1 to 21, or 1 to 28, of a 28 day cycle. In one embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on days 1 to 5, of a 28 day cycle. In one embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on days 1 to 5, of a 28 day cycle. In one embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on days 1 to 10, of a 28 day cycle. In one embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on days 1 to 10, of a 28 day cycle. In one embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on days 1 to 21, of a 28 day cycle. In one embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on days 1 to 21, of a 28 day cycle. In one embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on 1 to 28, of a 28 day cycle. In one embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on 1 to 28, of a 28 day cycle. In one embodiment, provided herein are methods of treating AML by administering Compound 1 to a subject in a dose of about 0.1 mg to about 20 mg in a cycle, wherein the cycle comprises administering Compound 1 in a dose of about 0.1 mg to about 20 mg on days 1 to 5, 1 to 10, 1 to 21, or 1 to 28, of a 28 day cycle. In one embodiment, provided herein are methods of treating relapsed refractory or AML by administering Compound 1 to a subject in a dose of about 0.1 mg to about 20 mg in a cycle, wherein the cycle comprises administering Compound 1 in a dose of about 0.1 mg to about 20 mg on days 1 to 5, 1 to 10, 1 to 21, or 1 to 28, of a 28 day cycle. In another embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on days 1 to 3 of a 28 day cycle. In another embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on days 1 to 3 of a 28 day cycle. In still another embodiment, provided herein are methods of treating, preventing, managing, and/or ameliorating AML by administering Compound 1 to a subject in a cycle, wherein the cycle comprises administering Compound 1 in a dose of about 0.1 mg to about 20 mg on days 1 to 5 and 15 to 19 of a 28 day cycle. In still another embodiment, provided herein are methods of treating, preventing, managing, and/or ameliorating relapsed or refractory AML by administering Compound 1 to a subject in a cycle, wherein the cycle comprises administering Compound 1 in a dose of about 0.1 mg to about 20 mg on days 1 to 5 and 15 to 19 of a 28 day cycle. In some such embodiments, provided herein are methods of treating, preventing, managing, and/or ameliorating AML by administering Compound 1 to a subject in a cycle, wherein the cycle comprises administering Compound 1 in a dose of about 0.6 mg, 1.2 mg, 1.8 mg, 2.4 mg, or 3.6 mg on days 1 to 3 of a 28 day cycle. In some such embodiments, provided herein are methods of treating, preventing, managing, and/or ameliorating relapsed or refractory AML by administering Compound 1 to a subject in a cycle, wherein the cycle comprises administering Compound 1 in a dose of about 0.6 mg, 1.2 mg, 1.8 mg, 2.4 mg, or 3.6 mg on days 1 to 3 of a 28 day cycle. In still another embodiment, provided herein are methods of treating, preventing, managing, and/or ameliorating AML by administering Compound 1 to a subject in a cycle, wherein the cycle comprises administering Compound 1 in a dose of about 0.6 mg, 1.2 mg, 1.8 mg, 2.4 mg, or 3.6 mg on days 1 to 5 and 15 to 19 of a 28 day cycle. In still another embodiment, provided herein are methods of treating, preventing, managing, and/or ameliorating relapsed or refractory AML by administering Compound 1 to a subject in a cycle, wherein the cycle comprises administering Compound 1 in a dose of about 0.6 mg, 1.2 mg, 1.8 mg, 2.4 mg, or 3.6 mg on days 1 to 5 and 15 to 19 of a 28 day cycle.

In one embodiment, provided herein are methods of treating, preventing, managing, and/or ameliorating MDS by administering Compound 1 to a subject in a dose of about 0.1 mg to about 20 mg. In one embodiment, provided herein are methods of treating MDS by administering Compound 1 to a subject in a dose of about 0.1 mg to about 20 mg. In one embodiment, provided herein are methods of treating, preventing, managing, and/or ameliorating MDS by administering Compound 1 to a subject in a cycle, wherein the cycle comprises administering Compound 1 in a dose of about 0.1 mg to about 20 mg on days 1 to 5, 1 to 10, 1 to 21, or 1 to 28, of a 28 day cycle. In one embodiment, provided herein are methods of treating MDS by administering Compound 1 to a subject in a dose of about 0.1 mg to about 20 mg in a cycle, wherein the cycle comprises administering Compound 1 in a dose of about 0.1 mg to about 20 mg on days 1 to 5, 1 to 10, 1 to 21, or 1 to 28, of a 28 day cycle. In another embodiment, provided herein are methods of treating, preventing, managing, and/or ameliorating MDS by administering Compound 1 to a subject in a cycle, wherein the cycle comprises administering Compound 1 in a dose of about 0.1 mg to about 20 mg on days 1 to 3 of a 28 day cycle. In still another embodiment, provided herein are methods of treating, preventing, managing, and/or ameliorating MDS by administering Compound 1 to a subject in a cycle, wherein the cycle comprises administering Compound 1 in a dose of about 0.1 mg to about 20 mg on days 1 to 5 and 15 to 19 of a 28 day cycle. In some such embodiments, provided herein are methods of treating, preventing, managing, and/or ameliorating MDS by administering Compound 1 to a subject in a cycle, wherein the cycle comprises administering Compound 1 in a dose of about 0.6 mg, 1.2 mg, 1.8 mg, 2.4 mg, or 3.6 mg on days 1 to 3 of a 28 day cycle. In still another embodiment, provided herein are methods of treating, preventing, managing, and/or ameliorating MDS by administering Compound 1 to a subject in a cycle, wherein the cycle comprises administering Compound 1 in a dose of about 0.6 mg, 1.2 mg, 1.8 mg, 2.4 mg, or 3.6 mg on days 1 to 5 and 15 to 19 of a 28 day cycle.

Further provided herein are methods for achieving one or more clinical endpoints associated with AML and/or MDS comprising administering a therapeutically effective amount of Compound 1 to a patient in need thereof.

In certain embodiments, the methods provided herein increase the overall survival (OS), complete remission rate (CRR), objective response rate (ORR), time to progression, relapse free survival (RFS), progression-free survival (PFS) event-free survival, duration of remission, duration of response, and/or time to remission/response in a patient population having AML treated with an effective amount of Compound 1, when compared to a patient population not treated with Compound 1. In certain embodiments, the methods provided herein increase the overall survival (OS), complete remission rate (CRR), objective response rate (ORR), time to progression, relapse free survival (RFS), progression-free survival (PFS) event-free survival, duration of remission, duration of response, time to remission/response, and/or transfusion independence in a patient population having AML treated with an effective amount of Compound 1, when compared to a patient population not treated with Compound 1.

In one embodiment, the methods provided herein increase the overall survival (OS) in a patient population having AML treated with an effective amount of Compound 1, when compared to a patient population not treated with Compound 1.

In one embodiment, the methods provided herein increase the complete remission rate (CRR) in a patient population having AML treated with an effective amount of Compound 1, when compared to a patient population not treated with Compound 1.

In one embodiment, the methods provided herein increase the objective response rate (ORR) in a patient population having AML treated with an effective amount of Compound 1, when compared to a patient population not treated with Compound 1.

In one embodiment, the methods provided herein increase the time to progression in a patient population having AML treated with an effective amount of Compound 1, when compared to a patient population not treated with Compound 1.

In one embodiment, the methods provided herein increase the relapse free survival (RFS) in a patient population having AML treated with an effective amount of Compound 1, when compared to a patient population not treated with Compound 1.

In one embodiment, the methods provided herein increase the progression-free survival (PFS) in a patient population having AML treated with an effective amount of Compound 1, when compared to a patient population not treated with Compound 1.

In one embodiment, the methods provided herein increase the event-free survival in a patient population having AML treated with an effective amount of Compound 1, when compared to a patient population not treated with Compound 1.

In one embodiment, the methods provided herein increase the duration of remission in a patient population having AML treated with an effective amount of Compound 1, when compared to a patient population not treated with Compound 1.

In one embodiment, the methods provided herein increase the duration of response in a patient population having AML treated with an effective amount of Compound 1, when compared to a patient population not treated with Compound 1.

In one embodiment, the methods provided herein increase the time to remission/response in a patient population having AML treated with an effective amount of Compound 1, when compared to a patient population not treated with Compound 1.

In one embodiment, the methods provided herein increase the transfusion independence in a patient population having AML treated with an effective amount of Compound 1, when compared to a patient population not treated with Compound 1.

In certain embodiments, the methods provided herein increase the overall survival (OS), complete remission rate (CRR), objective response rate (ORR), time to progression, relapse free survival (RFS), progression-free survival (PFS) event-free survival, duration of remission, duration of response, and/or time to remission/response in a patient population having MDS treated with an effective amount of Compound 1, when compared to a patient population not treated with Compound 1.

In one embodiment, the methods provided herein increase the overall survival (OS) in a patient population having MDS treated with an effective amount of Compound 1, when compared to a patient population not treated with Compound 1.

In one embodiment, the methods provided herein increase the complete remission rate (CRR) in a patient population having MDS treated with an effective amount of Compound 1, when compared to a patient population not treated with Compound 1.

In one embodiment, the methods provided herein increase the objective response rate (ORR) in a patient population having MDS treated with an effective amount of Compound 1, when compared to a patient population not treated with Compound 1.

In one embodiment, the methods provided herein increase the time to progression in a patient population having MDS treated with an effective amount of Compound 1, when compared to a patient population not treated with Compound 1.

In one embodiment, the methods provided herein increase the relapse free survival (RFS) in a patient population having MDS treated with an effective amount of Compound 1, when compared to a patient population not treated with Compound 1.

In one embodiment, the methods provided herein increase the progression-free survival (PFS) in a patient population having MDS treated with an effective amount of Compound 1, when compared to a patient population not treated with Compound 1.

In one embodiment, the methods provided herein increase the event-free survival in a patient population having MDS treated with an effective amount of Compound 1, when compared to a patient population not treated with Compound 1.

In one embodiment, the methods provided herein increase the duration of remission in a patient population having MDS treated with an effective amount of Compound 1, when compared to a patient population not treated with Compound 1.

In one embodiment, the methods provided herein increase the duration of response in a patient population having MDS treated with an effective amount of Compound 1, when compared to a patient population not treated with Compound 1.

In one embodiment, the methods provided herein increase the time to remission/response in a patient population having MDS treated with an effective amount of Compound 1, when compared to a patient population not treated with Compound 1.

In certain embodiment, the ORR includes all responses of complete remission (CR) (i.e., morphologic leukemia-free state, morphologic CR, cytogenetic CR, molecular CR, and morphologic CR with incomplete blood recovery), and partial remission.

6.4 Cycling Therapy/Dosages

In the methods provided herein, a therapeutically effective amount of Compound 1 can be cyclically administered to a patient in need thereof independent of the cancer treated. Cycling therapy can reduce the development of resistance to one or more of the therapies, avoid or reduce the side effects of one of the therapies, and/or improve the efficacy of the treatment.

In one embodiment, a therapeutically effective amount of Compound 1 is administered in a treatment cycle which includes an administration period of up to 5 days followed by a rest period. In one embodiment, the treatment cycle includes an administration period of 5 days followed by a rest period. In one embodiment, the treatment cycle includes an administration period of up to 10 days followed by a rest period. In one embodiment, the rest period is from about 10 days up to about 40 days. In one embodiment, the treatment cycle includes an administration period of up to 10 days followed by a rest period from about 10 days up to about 40 days. In one embodiment, the treatment cycle includes an administration period of up to 10 days followed by a rest period from about 23 days up to about 37 days. In one embodiment, the rest period is from about 23 days up to about 37 days. In one embodiment, the rest period is 23 days. In one embodiment, the treatment cycle includes an administration period of up to 10 days followed by a rest period of 23 days. In one embodiment, the rest period is 37 days. In one embodiment, the treatment cycle includes an administration period of up to 10 days followed by a rest period of 37 days.

In one embodiment, the treatment cycle includes an administration of a therapeutically effective amount of Compound 1 on days 1 to 5 of a 28 day cycle. In another embodiment, the treatment cycle includes an administration of Compound 1 on days 1 to 10 of a 28 day cycle. In one embodiment, the treatment cycle includes an administration of Compound 1 on days 1 to 5 of a 42 day cycle. In another embodiment, the treatment cycle includes an administration of Compound 1 on days 1 to 10 of a 42 day cycle.

In one embodiment, the treatment cycle includes an administration of a therapeutically effective amount of Compound 1 on days 1 to 21 of a 28 day cycle. In another embodiment, the treatment cycle includes an administration of a therapeutically effective amount of Compound 1 on days 1 to 5 of a 7 day cycle. In another embodiment, the treatment cycle includes an administration of a therapeutically effective amount of Compound 1 on days 1 to 7 of a 7 day cycle. In one embodiment, the treatment cycle includes an administration of a therapeutically effective amount of Compound 1 on days 1 to 5 and days 15 to 19 of a 28 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In certain embodiments, cycle 1 is a 42 day cycle and cycles 2 to 4 are 28 day cycles. In some embodiments, a therapeutically effective amount of Compound 1 is administered for 1 to 13 cycles of 28 days (e.g. about 1 year). In certain instances, the cycling therapy is not limited to the number of cycles, and the therapy is continued until disease progression. Cycles, can in certain instances, include varying the duration of administration periods and/or rest periods described herein.

In one embodiment the treatment cycle includes administering Compound 1 at a dosage amount of about 0.05 mg/day to about 20 mg/day, from about 0.1 mg/day to about 15 mg/day, from about 0.1 mg/day to about 10 mg/day, from about 0.3 mg/day to about 10 mg/day, from about 0.3 mg/day to about 8.5 mg/day, or from about 0.3 mg/day to about 8.1 mg/day, administered once per day.

In one embodiment the treatment cycle includes administering Compound 1 at a dosage amount of about 0.3 mg/day, 0.6 mg/day, 1.2 mg/day, 1.8 mg/day, 2.4 mg/day, 3.6 mg/day, 5.4 mg/day, 7.2 mg/day, 8.1 mg/day, 9.0 mg/day, 10.0 mg/day, 10.8 mg/day, or 12.2 mg/day administered once per day. In one embodiment the treatment cycle includes administering Compound 1 at a dosage amount of about 0.3 mg/day, 0.6 mg/day, 1.2 mg/day, 1.8 mg/day, 2.4 mg/day, 3.6 mg/day, 5.4 mg/day, 7.2 mg/day, 8.1 mg/day, 9.0 mg/day, 10.0 mg/day, 10.8 mg/day, 12.2 mg/day, or 20 mg/day administered once per day. In one embodiment the treatment cycle includes administering Compound 1 at a dosage amount of about 0.6 mg/day, 1.2 mg/day, 1.8 mg/day, 2.4 mg/day, or 3.6 mg/day, administered once per day. In some such embodiments, the treatment cycle includes administering Compound 1 at a dosage amount of about 0.6 mg, 1.2 mg, 1.8 mg, 2.4 mg, or 3.6 mg on days 1 to 3 of a 28 day cycle. In other embodiments, the treatment cycle includes administering Compound 1 at a dosage amount of about 0.6 mg, 1.2 mg, 1.8 mg, 2.4 mg, or 3.6 mg on days 1 to 5 and 15 to 19 of a 28 day cycle.

Compound 1 can be administered at the same amount for all administration periods in a treatment cycle. Alternatively, in one embodiment, the compound is administered at different doses in the administration periods.

6.5 Exemplary Formulations

Exemplary formulations comprising Compound 1, including the solid forms (e.g., Form A, Form B, Form C, Form D, Form E and/or amorphous of Compound 1) are described in U.S. application Ser. No. 15/400,791 filed on Jan. 6, 2017, the disclosure of which is incorporated herein by reference in its entirety. Exemplary lyophilized formulations are described below.

In certain embodiments, the lyophilized formulations comprise Compound 1, a buffer and a bulking agent. In one embodiment, a lyophilized formulation comprises about 0.1-2% Compound 1, about 2-15% buffer and about 70-95% bulking agent based on the total weight of the lyophilized formulation.

In one aspect, the lyophilized formulation comprises Compound 1 in an amount of about 0.1 to about 2% based on the total weight of the lyophilized formulation. In certain embodiments, the amount of Compound 1 is from about 0.1% to about 1.5%, about 0.1% to about 1% or about 0.35% to about 0.9% based on the total weight of the lyophilized formulation. In certain embodiments, the amount of Compound 1 is about 0.1%, 0.2%, 0.3%, 0.35%, 0.36%, 0.4%, 0.5%, 0.6%, 0.7%, 0.8%, 0.9%, or 1.0% based on the total weight of the lyophilized formulation. In one embodiment, the amount of Compound 1 in the lyophilized formulation is about 0.3 to about 0.4% based on the total weight of the lyophilized formulation. In one embodiment, the amount of Compound 1 in the lyophilized formulation is about 0.36% based on the total weight of the lyophilized formulation. In one embodiment, the amount of Compound 1 in the lyophilized formulation is about 0.9 to about 1% based on the total weight of the lyophilized formulation. In one embodiment, the amount of Compound 1 in the lyophilized formulation is about 0.93% based on the total weight of the lyophilized formulation.

In another aspect, the lyophilized formulation comprises Compound 1 in an amount of about 0.1 mg to about 5 mg in a 20 cc vial. In still another aspect, the lyophilized formulation comprises Compound 1 in an amount of about 0.1 mg to about 5 mg, about 0.1 mg to about 4 mg, about 0.1 mg to about 3 mg, about 0.1 mg to about 2 mg, about 0.5 mg to about 5 mg, about 0.5 mg to about 3 mg, about 0.5 mg to about 2 mg or about 0.5 mg to about 1.5 mg in a 20 cc vial. In one aspect Compound 1 is present in an amount of about 0.5, 0.6, 0.7, 0.75, 0.76, 0.8, 0.9, 1.0 or 1.2 mg in a 20 cc vial. In one aspect Compound 1 is present in an amount of about 0.76 mg in a 20 cc vial. In one aspect Compound 1 is present in an amount of about 1 mg in a 20 cc vial.

In one aspect, the lyophilized formulations contain a citrate buffer. In one aspect, the amount of citrate buffer in the formulations is from about 5% to about 25% based on total weight of the lyophilized formulation. In one aspect, the amount of citrate buffer in the formulations is about 10, 11, 12, 12.5, 12.7, 12.78, 12.8, 13, 14, 15, 16, 17, 17.3, 17.42, 17.5, 17.7, 18, 19 or 20% based on total weight of the lyophilized formulation. In one aspect, the amount of citrate buffer in the formulations is about 12.78% based on total weight of the lyophilized formulation. In one aspect, the amount of citrate buffer in the formulations is about 17.42% based on total weight of the lyophilized formulation.

In one embodiment, the citrate buffer comprises anhydrous citric acid and anhydrous sodium citrate. In certain embodiments, the amount of anhydrous citric acid is from about 2% to about 10%, about 3% to about 9%, about 5% to about 8% or about 6% to about 8% based on total weight of the lyophilized formulation. In certain embodiments, the amount of anhydrous citric acid in the lyophilized formulation is about 2%, 4%, 6%, 6.2%, 6.4%, 6.6%, 6.8%, 7%, 7.3%, 7.4%, 7.5%, 8%, 8.5% or 9% based on total weight of the lyophilized formulation. In one embodiment, the amount of anhydrous citric acid in the lyophilized formulation is about 6%, 6.2%, 6.4%, 6.41%, 6.6%, 6.8% or 7% based on total weight of the lyophilized formulation. In one embodiment, the amount of anhydrous citric acid in the lyophilized formulation is about 7%, 7.3%, 7.4%, 7.43%, 7.5% or 8% based on total weight of the lyophilized formulation. In one embodiment, the amount of anhydrous citric acid in the lyophilized formulation is about 6.41% based on total weight of the lyophilized formulation. In one embodiment, the amount of anhydrous citric acid in the lyophilized formulation is about 7.43% based on total weight of the lyophilized formulation.

In still another aspect, the lyophilized formulation comprises anhydrous citric acid in an amount of about 5 mg to about 20 mg in a 20 cc vial. In one embodiment, the amount of anhydrous citric acid is about 5, 6, 7, 8, 9, 10, 11, 12, 13, 14, 15, 16, 17, 18, 19 or 20 mg in a 20 cc vial. In one embodiment, the amount of anhydrous citric acid is about 17.7 mg in a 20 cc vial. In one embodiment, the amount of anhydrous citric acid is about 6.1 mg in a 20 cc vial.

In certain embodiments, the amount of anhydrous sodium citrate is from about 2% to about 15%, about 4% to about 15% or about 5% to about 10% based on total weight of the lyophilized formulation. In certain embodiments, the amount of anhydrous sodium citrate in the lyophilized formulation is about 2%, 3%, 4%, 5%, 6%, 6.2%, 6.37%, 6.4%, 6.6%, 6.8%, 7%, 7.5%, 8%, 8.5%, 9%, 9.5%, 10%, 12% or about 15% based on total weight of the lyophilized formulation. In one embodiment, the amount of anhydrous sodium citrate in the lyophilized formulation is about 6%, 6.2%, 6.37% 6.4%, 6.6%, 6.8% or 7% based on total weight of the lyophilized formulation. In one embodiment, the amount of anhydrous sodium citrate in the lyophilized formulation is about 8%, 8.5%, 9%, 9.5%, 9.99%, 10% or 10.5% based on total weight of the lyophilized formulation. In one embodiment, the amount of anhydrous sodium citrate in the lyophilized formulation is about 6.37% based on total weight of the lyophilized formulation. In one embodiment, the amount of anhydrous sodium citrate in the lyophilized formulation is about 9.99% based on total weight of the lyophilized formulation.

In still another aspect, the lyophilized formulation comprises anhydrous sodium citrate in an amount of about 5 mg to about 20 mg in a 20 cc vial. In one embodiment, the amount of anhydrous sodium citrate is about 5, 6, 7, 8, 9, 10, 11, 12, 13, 14, 15, 16, 17, 18, 19 or 20 mg in a 20 cc vial. In one embodiment, the amount of anhydrous sodium citrate is about 17.6 mg in a 20 cc vial. In one embodiment, the amount of anhydrous sodium citrate is about 8.2 mg in a 20 cc vial.

In certain embodiments, the amount of anhydrous citric acid in the lyophilized formulation is about 2%, 4%, 6%, 6.2%, 6.4%, 6.6%, 6.8%, 7%, 7.3%, 7.4%, 7.5%, 8%, 8.5% or 9% and the amount of anhydrous sodium citrate in the lyophilized formulation is about 2%, 3%, 4%, 5%, 6%, 6.2%, 6.4%, 6.6%, 6.8%, 7%, 7.5%, 8%, 8.5%, 9%, 9.5%, 10%, 12% or about 15% based on total weight of the lyophilized formulation. In one embodiment, the amount of anhydrous citric acid in the lyophilized formulation is about 6%, 6.2%, 6.4%, 6.6%, 6.8% or 7% and the amount of anhydrous sodium citrate in the lyophilized formulation is about 6%, 6.2%, 6.4%, 6.6%, 6.8% or 7% based on total weight of the lyophilized formulation. In one embodiment, the amount of anhydrous citric acid in the lyophilized formulation is about 7%, 7.3%, 7.4%, 7.5% or 8% and the amount of anhydrous sodium citrate in the lyophilized formulation is about 8%, 8.5%, 9%, 9.5%, 10% or 10.5% based on total weight of the lyophilized formulation. In one embodiment, the amount of anhydrous citric acid is about 6.1 mg and the amount of anhydrous sodium citrate is about 8.2 mg in a 20 cc vial. In one embodiment, the amount of anhydrous citric acid is about 17.7 mg and the amount of anhydrous sodium citrate is about 17.6 mg in a 20 cc vial.

In one aspect, the bulking agent in the lyophilized formulations comprises Captisol®, mannitol or Kleptose®, for example, β-cyclodextrin, hydroxypropyl β-cyclodextrin and methylated β-cyclodextrin. In certain embodiments, the bulking agent in the lyophilized formulations comprises Kleptose® hydroxypropyl β-cyclodextrins (Kleptose®HPB). In certain embodiments, the amount of the bulking agent in the lyophilized compositions is from about 70% to about 95%, about 75% to about 90% or about 80% to about 90% based on total weight of the lyophilized formulation. In certain embodiments, the amount of hydroxypropyl β-cyclodextrin in the lyophilized compositions is from about 70% to about 95%, about 75% to about 90% or about 80% to about 90% based on total weight of the lyophilized formulation. In certain embodiments, the amount of hydroxypropyl β-cyclodextrin in the lyophilized compositions is about 75%, 80%, 81%, 81.61%, 82%, 83%, 84%, 85%, 86%, 86.86%, 87%, 88%, 89% or 90% based on total weight of the lyophilized formulation. In one embodiment, the amount of hydroxypropyl β-cyclodextrin in the lyophilized compositions is about 86.86% based on total weight of the lyophilized formulation. In one embodiment, the amount of hydroxypropyl β-cyclodextrin in the lyophilized compositions is about 81.61% based on total weight of the lyophilized formulation.

In another aspect, the lyophilized formulation comprises Kleptose®HPB in an amount of about 67 mg in a 20 cc vial. In still another aspect, the lyophilized formulation comprises Kleptose®HPB in an amount of about 240 mg in a 20 cc vial.

In certain embodiments, the lyophilized formulation upon reconstitution has a pH of about 4 to 5. In one embodiment, the lyophilized formulation upon reconstitution has a pH of about 4, 4.1, 4.2, 4.3, 4.4, 4.5, 4.6, 4.7, 4.8, 4.9 or 5.

In certain embodiments, a container comprising a lyophilized composition is provided herein. In one aspect, the container is a glass vial. In one aspect, the container is a 20 cc glass vial.

The lyophilized formulation provided herein can be constituted for parenteral administration to a patient using any pharmaceutically acceptable diluent. Such diluents include, but are not limited to Sterile Water for Injection (SWFI), Dextrose 5% in Water (D5W), or a cosolvent system. Any quantity of diluent may be used to constitute the lyophilized formulation such that a suitable solution for injection is prepared. Accordingly, the quantity of the diluent must be sufficient to dissolve the lyophilized formulation. In one embodiment, 1-5 mL or 1 to 3 mL of a diluent are used to constitute the lyophilized formulation to yield a final concentration of about 0.1-5 mg/mL, about 0.1-1 mg/mL, about 0.5-1 mg/mL of Compound 1. In certain embodiments, the final concentration of Compound 1 in the reconstituted solution is about 0.5 mg/mL. In certain embodiments, the volume of the reconstitution diluent varies between 2 ml and 20 ml to yield a final concentration of 0.05-0.5 mg/mL. In certain embodiments, depending on the required dose, multiple vials may be used for reconstitution.

The constituted solutions of lyophilized formulation can be stored and used within up to about 24 hours, about 12 hours or about 8 hours. In some embodiments, the solution is used within 8 hour of preparation. In some embodiments, the solution is used within 5 hour of preparation. In some embodiments, the solution is used within 1 hour of preparation.

In one aspect, the lyophilized formulation is provided in a 20 cc vial that includes: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide and a pharmaceutically acceptable carrier or excipient that includes a buffer and bulking agent as described herein. The buffer and bulking agent can be present at an amount as described herein.

In one aspect, the lyophilized formulation is provided in a 20 cc vial that includes: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 17.7 mg anhydrous citric acid, 17.6 mg anhydrous sodium citrate and 240 mg Kleptose® HPB as described herein. In one embodiment, the lyophilized formulation in a 20 cc vial is reconstituted with 2 mL sterile water for injection.

In one aspect provided herein is an aqueous composition comprising a lyophilized formulation provided herein. In one embodiment, the aqueous solution comprises 0.5 mg/mL Compound 1.

6.6 Combination Therapy

In certain embodiments, the methods provided herein comprise administration of a therapeutically effective amount of Compound 1 in combination with a therapeutically effective amount of other therapeutic agents.

In one embodiment, provided herein is a method of treating, preventing, or managing leukemia, comprising administering to a patient a therapeutically effective amount of Compound 1 in a cycling therapy as provided herein in combination with a therapeutically effective amount of one or more second active agents, and optionally in combination with radiation therapy, blood transfusions, biological or immunotherapy, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a lyophilized formulation of Compound 1 provided herein), can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

In certain embodiments, the methods provided herein comprise administration of one or more of calcium, calcitriol, and vitamin D supplementation with Compound 1. In certain embodiments, the methods provided herein comprise administration of calcium, calcitriol, and vitamin D supplementation with Compound 1. In certain embodiments, the methods provided herein comprise administration of calcium, calcitriol, and vitamin D supplementation prior to the treatment with Compound 1. In certain embodiments, the methods provided herein comprise administration of calcium, calcitriol, and vitamin D supplementation prior to the administration of first dose of compound 1 in each cycle. In certain embodiments, the methods provided herein comprise administration of calcium, calcitriol, and vitamin D supplementation at least up to 3 days prior to the treatment with Compound 1. In certain embodiments, the methods provided herein comprise administration of calcium, calcitriol, and vitamin D supplementation prior to the administration of first dose of compound 1 in each cycle. In certain embodiments, the methods provided herein comprise administration of calcium, calcitriol, and vitamin D supplementation at least up to 3 days prior to the administration of first dose of compound 1 in each cycle. In certain embodiments, the methods provided herein comprise administration of calcium, calcitriol, and vitamin D supplementation prior to administration of first dose of compound 1 in each cycle and continues after administration of the last dose of Compound 1 in each cycle. In certain embodiments, the methods provided herein comprise administration of calcium, calcitriol, and vitamin D supplementation at least up to 3 days prior to administration of first dose of compound 1 in each cycle and continues until at least up to 3 days after administration of the last dose of Compound 1 in each cycle (e.g., at least up to day 8 when Compound 1 is administered on Days 1-5).

In certain embodiments, calcium supplementation is administered to deliver at least 1200 mg of elemental calcium per day given in divided doses. In certain embodiments, calcium supplementation is administered as calcium carbonate in a dose of 500 mg administered three times a day per orally (PO).

In certain embodiments, calcitriol supplementation is administered to deliver 0.25 µg calcitriol (PO) once daily.

In certain embodiments, vitamin D supplementation is administered to deliver about 500 IU to about 50,000 IU vitamin D once daily. In certain embodiments, vitamin D supplementation is administered to deliver about 1000 IU vitamin D once daily. In certain embodiments, vitamin D supplementation is administered to deliver about 500 IU vitamin D once daily. In certain embodiments, vitamin D supplementation is administered to deliver about 50,000 IU vitamin D weekly. In certain embodiments, vitamin D supplementation is administered to deliver about 20,000 IU vitamin D weekly. In certain embodiments, vitamin D supplementation is administered to deliver about 1000 IU vitamin D2 or D3 once daily. In certain embodiments, vitamin D supplementation is administered to deliver about 50,000 IU vitamin D2 or D3 weekly. In certain embodiments, vitamin D supplementation is administered to deliver about 20,000 IU vitamin D2 or D3 weekly.

In certain embodiments, administration of a therapeutically effective amount of Compound 1 and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of Compound 1 is independent of the route of administration of a second therapy. Thus, in accordance with these embodiments, Compound 1 is administered intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1 and a second therapy are administered by the same mode of administration, by IV. In another embodiment, Compound 1 is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of Compound 1 and any optional additional active agents concurrently administered to the patient.

In some embodiment, the components of the combination therapies described herein are cyclically administered to a patient. In another embodiment, a second active agent is co-administered in a cyclic administration with the combination therapies provided herein. Cycling therapy involves the administration of an active agent for a period of time, followed by a rest for a period of time, and repeating this sequential administration. Cycling therapy can be performed independently for each active agent (e.g., Compound 1, and/or a second active agent described herein) over a prescribed duration of time. In certain embodiments, the cyclic administration of each active agent is dependent upon one or more of the active agents administered to the subject. In one embodiment, administration of Compound 1 or second active agent described herein fixes the day(s) or duration of administration of each agent. In another embodiment, administration of Compound 1 or second active agent described herein fixes the days(s) or duration of administration of a second active agent.

In some embodiments, Compound 1 and a second active agent described herein are administered continually (e.g., daily, weekly, monthly) without a rest period. Cycling therapy can reduce the development of resistance to one or more of the therapies, avoid, or reduce the side effects of one of the therapies, and/or improve the efficacy of the treatment or therapeutic agent.

In one embodiment, a therapeutically effective amount of Compound 1 is administered as a component of a combination therapy as described herein once daily for days 1 to 5, days 1 to 10, days 1 to 21, or 28 consecutive days in a 28 days cycle. Such combination therapies comprise administration of a second active agent as described herein prior to, concomitantly with, or subsequent to administration of Compound 1 on one or more days (e.g., on day 1 of cycle 1). In one embodiment, the combination therapy is administered for 1 to 13 cycles of 28 days (e.g., about 12 months). Compound 1 and a second active agent described herein of such a combination can be present at a concentration or amount as set forth herein. In certain embodiments, the second active agent can be administered once daily, once weekly, or once monthly during the cycling therapy. In another embodiment, the second active agent is administered once weekly in combination with a combination therapy described herein.

In one embodiment, a therapeutically effective amount of Compound 1 is administered as a component of a combination therapy as described herein once daily for 7 consecutive days in a 7 days cycle. Such combination therapies comprises administration of a therapeutically effective amount of a second active agent as described herein prior to, concomitantly with, or subsequent to administration of a therapeutically effective amount of Compound 1 on one or more days (e.g., on day 1 of cycle 1). In another embodiment, a therapeutically effective amount of Compound 1 is administered once daily for 5 consecutive days followed by 2 days of rest (e.g., no administration of the compound/discontinuation of treatment) in a 7 days cycle. Such a combination therapy comprises administration of a therapeutically effective amount of a second active agent as described herein prior to, concomitantly with, or subsequent to administration of Compound 1 on one or more days (e.g., on day 1 of cycle 1). In one embodiment, the combination therapy is administered for 1 to 13 cycles of 28 days (e.g., about 3 months). Compound 1 and second active agents as described herein of such a combination can be present at a concentration or amount as set forth herein. In one embodiment the combination therapy comprises administration of a therapeutically effective amount of Compound 1 consecutively for 5 days of a 7 days cycle and administration of a therapeutically effective amount of a second active agent on at least one day of each cycle (e.g., day 1 of cycle 1) in combination with a second active agent administered on at least one day of each cycle. In one embodiment, a therapeutically effective amount of Compound 1 is administered as a component of a combination therapy as described herein once daily on days 1 to 5, 1 to 10, 1 to 21, or 1 to 28, of a 28 day cycle. Such combination therapies comprises administration of a therapeutically effective amount of a second active agent as described herein prior to, concomitantly with, or subsequent to administration of a therapeutically effective amount of Compound 1 on one or more days. In another embodiment, a therapeutically effective amount of Compound 1 is administered once daily on days 1 to 3 of a 28 day cycle. Such a combination therapy comprises administration of a therapeutically effective amount of a second active agent as described herein prior to, concomitantly with, or subsequent to administration of Compound 1 on one or more days. In another embodiment, a therapeutically effective amount of Compound 1 is administered once daily on days 1 to 5 and 15 to 19 of a 28 day cycle. Such a combination therapy comprises administration of a therapeutically effective amount of a second active agent as described herein prior to, concomitantly with, or subsequent to administration of Compound 1 on one or more days.

In certain embodiments, the second active agent can be administered once daily, once weekly, or once monthly during the cycling therapy. In another embodiment, the second active agent is administered once weekly in combination with a combination therapy described herein.

A compound for use in combination therapies described herein can independently be administered once daily (QD), or divided into multiple daily doses such as twice daily (BID), three times daily (TID), and four times daily (QID) as part of a combination therapy described herein. In addition, the administration can be continuous (i.e., daily for consecutive days or every day), intermittent, e.g., in cycles (i.e., including days, weeks, or months of rest without drug). As used herein, the term "daily" is intended to mean that a therapeutic agent is administered once or more than once each day, for example, for a period of time. The term "continuous" is intended to mean that a therapeutic agent is administered daily for an uninterrupted period of at least 10 days to 52 weeks. The term "intermittent" or "intermittently" as used herein is intended to mean stopping and starting at either regular or irregular intervals. For example, intermittent administration of a compound for use in combination therapies described herein can be administered for one to six days per week, administration in cycles (e.g., daily administration for two to eight consecutive weeks, then a rest period with no administration for up to one week), or administration on alternate days. The term "cycling" as used herein is intended to mean that a therapeutic agent is administered daily or continuously but with a rest period.

In certain embodiments, a compound for use in combination therapies described herein is administered once per day from one day to six months, from one week to three months, from one week to four weeks, from one week to three weeks, or from one week to two weeks. In certain embodiments, a compound for use in combination therapies described herein is administered once per day for one week, two weeks, three weeks, or four weeks. In one embodiment, a compound for use in combination therapies described herein is administered once per day for one week. In another embodiment, a compound for use in combination therapies described herein is administered once per day for two weeks. In yet another embodiment, a compound for use in combination therapies described herein is administered once per day for three weeks. In still another embodiment, a compound for use in combination therapies described herein is administered once per day for four weeks.

One or more second active ingredients or agents can be used together with Compound 1 in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with Compound 1 are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with Compound 1 include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), elotuzumab (Empliciti™), daratumumab (Darzalex™), isatuximab (also known as SAR650984), and G250. The lyophilized formulation of Compound 1 can also be combined with, or used in combination with, anti-TNF-α antibodies, and/or anti-EGFR antibodies, such as, for example, Erbitux® (cetuximab) or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of Compound 1 provided herein. However, like some large molecules, many are believed to be capable of providing a synergistic effect when administered with (e.g., before, after or simultaneously) Compound 1 provided herein. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitior or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; bortezomib (Velcade®); brequinar sodium; bropirimine; busulfan; cactinomycin; calusterone; caracemide; carbetimer; carboplatin; carfilzomib (Kyprolis®); carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; ixazomib (Nanlaro®), lanreotide acetate; lenalidomide (Revlimid®); letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; panobinostat, pegaspargase; peliomycin; pentamustine; peplomycin sulfate; perfosfamide; pipobroman; piposulfan; piroxantrone hydrochloride; plicamycin; plomestane; pomalidomide (Pomalyst®); porfimer sodium; porfiromycin; prednimustine; procarbazine hydrochloride;

puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thalidomide (Thalomid®); thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lenalidomide, lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine;

trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vidaza, vinorelbine; vinxaltine; vitaxin; vorozole; zanoterone; zeniplatin; zilascorb; and zinostatin stimalamer.

In certain embodiments, Compound 1 is administered in combination with checkpoint inhibitors. In one embodiment, one checkpoint inhibitor is used in combination with Compound 1 in connection with the methods provided herein. In another embodiment, two checkpoint inhibitors are used in combination with Compound 1 in connection with the methods provided herein. In yet another embodiment, three or more checkpoint inhibitors are used in combination with Compound 1 in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer*, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitors is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhTL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with second active agents as described herein where appropriate for treating diseases described herein and understood in the art.

In certain embodiments, Compound 1 can be used in combination with one or more immune cells expressing one or more chimeric antigen receptors (CARs) on their surface (e.g., a modified immune cell). Generally, CARs comprise an extracellular domain from a first protein e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAP1 (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, C0-029, FGF-5, G250, Ga733 (EpCAM), HTgp-175, M344, MA-50, MG7-Ag, MOV18, NB\70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., Blood 1 05(11):4247-4254 (2005).

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide. In some embodiments of the methods or compositions described here, the second active agent is one or more of enasidenib, azacitidine, CC-486, decitabine, cytarabine (ara-C), daunorubicin (daunomycin), idarubicin, cladribine, midostaurin, fludarabine, topotecan, arsenic trioxide, or mitoxantrone.

In certain embodiments of the methods provided herein, the use of a second active agent in combination with Compound 1 may be modified or delayed during or shortly following administration of Compound 1 provided herein as deemed appropriate by the practitioner of skill in the art. In certain embodiments, subjects being administered Compound 1 alone or in combination with other therapies may receive supportive care including antiemetics, myeloid growth factors, and transfusions of platelets, when appropriate. In some embodiments, subjects being administered Compound 1 may be administered a growth factor as a second active agent according to the judgment of the practitioner of skill in the art. In some embodiments, provided is administration of Compound 1 in combination with erythropoietin or darbepoetin (Aranesp).

In certain embodiments, Compound 1 is administered in combination with arsenic trioxide, fludarabine, carboplatin, daunorubicin, cyclophosphamide, cytarabine, doxorubicin, idarubicin, mitoxantrone hydrochloride, thioguanine, vincritine, and/or topotecan to patients with acute myeloid leukemia, including refractory or relapsed acute myeloid leukemia. In certain embodiments, Compound 1 is administered in combination with arsenic trioxide, fludarabine, carboplatin, daunorubicin, cyclophosphamide, cytarabine, doxorubicin, idarubicin, mitoxantrone hydrochloride, thioguanine, vincristine, topotecan and/or enasidenib to patients with acute myeloid leukemia, including refractory or relapsed acute myeloid leukemia.

In certain embodiments, Compound 1 is administered in combination with azacitidine, cytarabine, daunorubicin, decitabine, idarubicin or lenalidomide to patients with MDS. In certain embodiments, Compound 1 is administered in combination with enasidenib, azacitidine, CC-486, cytarabine, daunorubicin, decitabine, idarubicin or lenalidomide to patients with MDS.

It will be appreciated that every suitable combination of the compounds provided herein with one or more of the aforementioned compounds and optionally one or more further pharmacologically active substances is contemplated herein.

6.7 Patient Population

In certain embodiments of the methods provided herein, the subject is an animal, for example, a mammal, or a non-human primate. In a particular embodiment, the subject is a human. The subject can be a male or female subject.

Particularly useful subjects for the methods provided herein include human leukemia patients, for example, those who have been diagnosed with acute myeloid leukemia, including relapsed or refractory acute myeloid leukemia.

In some embodiments, the subject is 18 years or older. In some embodiments, the subject is more than 18, 25, 35, 40, 45, 50, 55, 60, 65, or 70 years old. In other embodiments, the subject is less than 65 years old.

In some embodiments, the subject is treated based on the Eastern Cooperative Oncology Group (ECOG) performance status score of the subject for leukemia. In some embodiments, the subject has an ECOG performance status score of 0 to 2. In some embodiments, the subject has an ECOG performance status score of 0. In some embodiments, the subject has an ECOG performance status score of 1. In other embodiments, the subject has an ECOG performance status score of 2.

In some embodiments, the subject is treated based on the Eastern Cooperative Oncology Group (ECOG) performance status score of the subject for non-Hodgkin lymphoma (NHL). In some embodiments, the subject has an ECOG performance status score of 0 to 1. In some embodiments, the subject has an ECOG performance status score of 0. In some embodiments, the subject has an ECOG performance status score of 1.

In some embodiments, the subject is treated based on the Eastern Cooperative Oncology Group (ECOG) performance status score of the subject for myelodysplastic syndrome (MDS). In some embodiments, the subject has an ECOG performance status score of 0 to 2. In some embodiments, the subject has an ECOG performance status score of 0. In some embodiments, the subject has an ECOG performance status score of 1. In other embodiments, the subject has an ECOG performance status score of 2.

In some embodiments, the subject is treated based on the Eastern Cooperative Oncology Group (ECOG) performance status score of the subject for mantle cell lymphoma (MCL). In some embodiments, the subject has an ECOG performance status score of 0 to 2. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of a subject in which at least 4 weeks (from first dose of Compound 1) have elapsed from donor lymphocyte infusion (DLI) without conditioning.

In certain embodiments, the methods provided herein encompass the treatment of a subject who has the following screening laboratory values:

Corrected serum Ca or free (ionized) serum Ca within normal limits (WNL).

Corrected Ca (mg/dL)=Total Ca (mg/dL)−0.8 (albumin [g/dL]−4)

Total White Blood Cell count (WBC)<25×109/L prior to first infusion. Prior leukapheresis and/or prior or concurrent treatment with hydroxyurea to achieve this level are allowed.

Potassium and magnesium within normal limits or correctable with supplements.

Aspartate aminotransferase/serum glutamic oxaloacetic transaminase (AST/SGOT) or alanine aminotransferase/serum glutamate pyruvic transaminase (ALT/SGPT)≤2.5× Upper Limit of Normal (ULN).

Uric acid ≤7.5 mg/dL (446 μmol/L). Prior and/or concurrent treatment with hypouricemic agents (eg, allopurinol, rasburicase) are allowed.

Serum bilirubin ≤1.5×ULN.

Estimated serum creatinine clearance of ≥60 mL/min using the Cockcroft-Gault equation.

INR <1.5×ULN and PTT <1.5×ULN.

In other embodiments, the methods encompass treating subjects who have been previously treated or are currently being treated for leukemia. For example, the subject may have been previously treated or are currently being treated with a standard treatment regimen for leukemia. The subject may have been treated with any leukemia treatment regimen prescribed by the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen.

In certain embodiments, the subject has no clinical symptoms suggesting active central nervous system (CNS) leukemia or known CNS leukemia.

In certain embodiments, the subject does not have immediately life-threatening, severe complications of leukemia such as disseminated/uncontrolled infection, uncontrolled bleeding, and/or uncontrolled disseminated intravascular coagulation.

In certain embodiments, the subject does not have impaired cardiac function or clinically significant cardiac diseases.

In some embodiments, the subject has not undergone prior autologous hematopoietic stem cell transplant 3 months or less than 3 months prior to treatment of Compound 1 according to the methods provided herein.

In some embodiments, the subject has not undergone prior allogeneic hematopoietic stem cell transplant (HSCT) with either standard or reduced intensity conditioning less than 6 months prior to starting treatment with Compound 1 according to the methods provided herein.

In some embodiments, the subject is not on systemic immunosuppressive therapy post HSCT, or with clinically significant graft-versus-host disease (GVHD).

In some embodiments, the subject has not undergone prior systemic cancer-directed treatments or investigational modalities less than five half lives or 4 weeks prior to starting treatment of Compound 1, whichever is shorter. In some embodiments, the subject has received hydroxyurea treatment.

In some embodiments, the subject has not undergone a major surgery less than two weeks prior to starting treatment of Compound 1.

In some embodiments, the subject has no known HIV infection. In some embodiments, the subject has no known chronic, active hepatitis B or C (HBV/HCV) infection.

In some embodiments, the subject is not undergoing treatment with chronic, therapeutic dosing of anti-coagulants (eg, warfarin, low molecular weight heparin, Factor Xa inhibitors). In some embodiments, the subject has no history of concurrent second cancers requiring active, ongoing systemic treatment.

In certain embodiments, the subject has no disorders or conditions disrupting normal calcium homeostasis or preventing calcium supplementation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

6.8 Evaluation of Activity

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays.

Embodiments provided herein may be more fully understood by reference to the following examples. These examples are meant to be illustrative of pharmaceutical compositions and dosage forms provided herein, but are not in any way limiting.

7. EXAMPLES

The following Examples are presented by way of illustration, not limitation. The following abbreviations are used in descriptions and examples.

ABC=activated B cell,
ALL=acute lymphoblastic leukemia,
AML=acute myeloid leukemia,
ATCC=American Tissue Culture Collection,
AUC=area under the curve=Activity Area,
AV=Annexin V,
BCL=B-cell lymphoma;
BFU-E=burst forming unit of erythrocytes,
BME=β-mercaptoethanol,
CFU-E=colony forming unit of erythrocytes,
CFU-GEMM=colony forming unit of granulocyte/erythrocyte/monocyte/megakaryocyte,
CFU-GM=colony forming unit of granulocyte/monocyte,
CLL=chronic lymphoid leukemia,
c-Maf=v-maf avian musculoaponeurotic fibrosarcoma oncogene homolog,
DLBCL=diffuse large B-cell lymphoma,
DMEM=Dulbecco's modified Eagle's medium,
DMSO=dimethyl sulfoxide,
DSMZ=Deutsche Sammlung von Mikroorganismen und Zellkulturen,
FAB=French-American-British,
FBS=fetal bovine serum,
FGFR3=fibroblast growth factor receptor 3,
GCB=germinal center B
g/L=grams per liter, GM CSF=granulocyte-macrophage colony stimulating factor,
hr=hour(s),
HEPES=2-[4-(2hydroxyethyl)piperazin-1-yl]ethanesulfonic acid,
HP=haptoglobin,
HPC=hematopoietic progenitor cells,
IMDM=Iscove's modified Dulbecco's medium,
TBA=Tert-butyl alcohol,
MCL=mantle cell lymphoma,
N=number of experiments,
NA=not available,
NF=No 'Good Curve' Fit,
nM=nanomolar,
NR=No Ranking,
PBMCs=peripheral blood mononuclear cells,
MafB=V-maf musculoaponeurotic fibrosarcoma oncogene homolog B,
MEM=minimum essential medium,
MMSET=multiple myeloma SET domain,
RPMI=Roswell Park Memorial Institute tissue culture medium,
SD=standard deviation,
μM=micromolar, and
y=years.

Example 1

Lyophilized Formulations

The lyophilized formulations of Compound 1 having the composition as described in the Tables A and B were prepared using procedures described in U.S. application Ser. No. 15/400,791.

TABLE A

|  | Formulation IA | Formulation IC | Formulation II | Formulation III |
|---|---|---|---|---|
| Compound 1 (mg/mL) * | 0.125 | 0.125 | 0.40 | 0.50 |
| Excipients | Captisol ® (30 mg/mL) | Kleptose ® (30 mg/mL) | Captisol ® (20 mg/mL) | Mannitol (50 mg/mL) |
| Citrate buffer (% v/v) | 100 | 100 | 60 | 50 |
| TBA (% v/v) | 0 | 0 | 40 | 50 |

TABLE B

| Lot No. | Formulation IX | Formulation IC | Formulation ID |
|---|---|---|---|
| Form C (mg/vial) | 0.76 | 1.0 | 1.0 |
| Citric acid anhydrous, USP (mg/vial) | 6.1 | 17.7 | 17.7 |
| Sodium citrate anhydrous, USP (mg/vial) | 8.2 | 17.6 | 17.6 |
| Kleptose ® HPB, parenteral grade (mg/vial) | 67 | 240 | 240 |
| TBA (in process media) | Removed upon drying | 0 | 0 |
| N,N-Dimethylacetamide, PW (in process media)* | Removed upon drying | | |
| Total | 82.1 | 276.3 | 276.3 |

Example 2

Evaluation of the Antiproliferative and Proapoptotic Effects of Compound 1 in AML Cell Lines In Vitro and Comparison with Non-Tumorigenic Normal Cells 3-Day Via CellTiter Glo® (CTG) Luminescent Cell Viability Assay Cell Culture Materials: Human AML, mantle cell lymphoma (MCL), Burkitt lymphoma, and myeloma cell lines were purchased from the vendors indicated in Table 1, Table 2 and Table 3. Human normal donor PBMCs and chronic lymphoid leukemia (CLL) patient blasts were obtained from AllCells, LLC (Alameda, Calif.). The hematological and primary cell samples were cultured at 37° C. with 5% $CO_2$ in the media indicated in Table 1, Table 2 and Table 3. All cell lines were kept in log phase, and cell density and viability were monitored by trypan blue exclusion using the Vi-cell XR cell viability analyzer (Beckman Coulter, Brea, Calif.). Human PBMCs were cultured on Corning® Bio-Coat™ T-Cell Activation Anti-Human CD3 96-well plates (Corning Inc., Corning, N.Y.).

TABLE 1

Acute Myeloid Leukemia Cell Lines Tested

| Cell Line | AML FAB Classification | Source | Cell Culture Media |
|---|---|---|---|
| KG-1 | FAB M0/1 | ATCC | RPMI + |
| NB-4 | FAB M3 | DSMZ | 10% FBS |
| Kasumi-1 | FAB M2 | ATCC | 1X HEPES |
| U937 | FAB M5 | ATCC | 1X sodium |
| HNT-34 | FAB M4 | DSMZ | pyruvate |
| MOLM-13 | FAB M5a | ATCC | 1X non-essential amino acids |
| HL-60 | FAB M2 | ATCC | IMDM + |
| KG-1a | FAB M0/1 | ATCC | 15% FBS |
| MV-4-11 | FAB M5 | ATCC | |
| OCI-AML2 | FAB M4 | DSMZ | MEM + |
| OCI-AML3 | FAB M4 | DSMZ | 10% FBS |

TABLE 2

Lymphoma Cell Lines Tested

| Cell Line | Lymphoma Classification | Source | Cell Culture Media |
|---|---|---|---|
| WSUFSCCL | Follicular lymphoma | DSMZ | 10% FBS |
| Mino | MCL | ATCC | RPMI |
| JeKo-1 | MCL | ATCC | |
| DoHH2 | Follicular Lymphoma | DSMZ | |
| SR | ALL | DSMZ | |
| SU-DHL-1 | GCB DLBCL | DSMZ | |
| U2932 | ABC DLBCL | DSMZ | |
| RC-K8 | ABC DLBCL | DSMZ | |
| DG-75 | Burkitt lymphoma | DSMZ | |
| WSU-NHL | Follicular lymphoma | DSMZ | |
| Rec-1 | MCL | ATCC | 15% FBS |
| SU-DHL-5 | GCB DLBCL | DSMZ | RPMI |
| SU-DHL-6 | GCB DLBCL | DSMZ | |
| Karpas 231 | ALL | DSMZ | |
| MC-116 | ALL | DSMZ | |
| Karpas 299 | ALL | DSMZ | |
| SC-1 | DLBCL | DSMZ | 20% FBS |
| Namalwa | Burkitt lymphoma | DSMZ | RPMI |
| JVM-2 | MCL | DSMZ | |
| JVM-13 | MCL | ATCC | |
| SU-DHL-8 | GCB DLBCL | DSMZ | |
| EB-1 | Burkitt lymphoma | DSMZ | 10% FBS |
| BL-70 | Burkitt lymphoma | DSMZ | RPMI + |
| Blue-1 | Burkitt lymphoma | DSMZ | 50 µM BME |
| OCI-LY-10 | ABC DLBCL | DSMZ | |
| Daudi | Burkitt lymphoma | DSMZ | RPMI + |
| HS-Sultan | Burkitt lymphoma | ATCC | 10% FBS |
| Ramos | Burkitt lymphoma | ATCC | 1.5 g/L sodium bicarbinate |
| Raji | Burkitt lymphoma | ATCC | 4.5 g/L glucose 1 mM sodium pyruvate |
| Granta | MCL | ATCC | 20% FBS in DMEM |
| OCI-LY7 | GCB DLBCL | DSMZ | IMDM + 20% HP + 20 µM BME |
| BL-41 | Burkitt lymphoma | DSMZ | 10% FBS RPMI + 50 µM BME |

TABLE 3

Multiple Myeloma Cell Lines Tested

| Cell Line | Genetic Translocations | Source | Cell Culture Media |
|---|---|---|---|
| DF15 | t(14; 16) c-Maf/MafB | Gift from Dr. John D. Shaughnessy | RPMI + 10% FBS |
| DF15R (Pomalidomide-resistant) | t(14; 16) c-Maf/MafB | Generated at Celgene | 1X HEPES 1X sodium pyruvate 1X non-essential amino acids |
| OPM-2 | t(4; 14) - FGFR3 & MMSET | ATCC | |
| OPM2 P10 (Pomalidomide-resistant) | t(4; 14) - FGFR3 & MMSET | Generated at Celgene | |
| H929 | t(4; 14) - FGFR3 & MMSET | ATCC | |
| H929 R10-1 (Lenalidomide-resistant) | t(4; 14) - FGFR3 & MMSET | Generated at Celgene | |
| JJN3 | t(14; 16) - c-Maf | DSMZ | |
| U266 | t(11; 14) - Cyclin D1 | ATCC | |
| RPMI 8226 | t(16; 22) | ATCC | |
| SK-MM-2 | t(11; 14) - Cyclin D1(BCL1) | DSMZ | |
| EJM | t(14; 20) - Mafb | DSMZ | |

Preparation of Solutions of Test Article: Compounds were plated into black 384-well plates (Corning Inc.) to a final DMSO volume of 0.1% assuming a maximal volume of 50 µL. A 10-point dose response starting at 10 µM with a 1:3 dilution was printed in duplicate by acoustic dispense using the EDC ATS-100 platform.

Cell Proliferation Assays: The effect of Compound 1 on the proliferation/viability of the hematological cell lines (Table 1, Table 2 and Table 3), THLE-2, or PBMCs was assessed after 72 hours incubation using CTG (Promega), according to manufacturer's instructions. Hematological cell lines were dispensed into compound plates by a Multidrop™ Combi Reagent Dispenser (Thermo Scientific, Waltham, Mass.) at a concentration of 0.1 to $0.3 \times 10^6$ cells per mL in a 50 µL total volume. THLE-2 cells were seeded out at 1000 cells per well in 50 µL volume and incubated for 72 hours. At 72 hours, 25 µL per well of CTG was dispensed by a Multidrop™ Combi Reagent Dispenser and adenosine triphosphate (ATP) release by viable cells was measured as relative luminescence units after 30 minutes using the Envision platform.

For frozen PBMCs, cells were thawed at 37° C. for 2 minutes in RPMI with 10% FBS and cell counts and viability were measured on the ViCell as previously described. Peripheral blood mononuclear cells were washed and diluted to $1 \times 10^6$ cells per mL and dispensed by a Multidrop™ Combi Reagent Dispenser in a volume of 25 µL/well into the compound plates and incubated for 2 hours. After 2 hours, 25 µL of anti-CD3 antibody-bound beads (1 cell:2 anti-human CD3 antibody-coated M-450 beads) were dispensed per well and incubated for a further 72 hours. After 72 hours, 15 µL of supernatants were collected for the analysis of interleukin (IL)-2 release using the Human IL-2 384-well Tissue Culture Kit (Meso Scale Diagnostics), according to the manufacturer's instructions, and the remaining cell suspension was processed with CTG.

Cell Apoptosis Assays: The ability of Compound 1 to induce apoptosis was assessed in selected AML cell lines and healthy PBMCs at the time points and compound concentrations indicated. For Annexin V/7-AAD readout by flow cytometry, AML cell lines were plated into flat bottom 96-well plates (BD Falcon) at a seeding density of 0.1 to $0.3 \times 10^6$ cells per mL in 200 µL complete media. Compound 1 was dispensed onto the plates and the cells were incubated for the times indicated. For frozen PBMCs, cells were thawed as previously described and plated at a seeding density of $1 \times 10^6$ cells per mL in 200 µL on Corning® BioCoat™ T-Cell Activation Anti-Human CD3 96-well plates (Corning Inc., Corning, N.Y.). Compound 1 was dispensed onto the plates and the cells were incubated for the times indicated. At the end of the incubation period, 100 µL of cells were transferred into a 96-well U-bottom plate (BD Falcon) and centrifuged at 1200 rpm for 5 minutes and the media removed. Then 2.5 µL of Annexin V-AF647 (Biolegend) and 5 µL 7-AAD (Biolegend) were added to 100 µL of 1× Annexin binding buffer (BD Biosciences). One hundred microliters of Annexin V/7-AAD buffer was added per well and the cells incubated for 15 minutes before being analyzed using the Attune Flow Cytometer (Life Technologies, Carlsbad, Calif.). For caspase 3/7 activity, the remaining 100 µL was incubated with CellEvent™ Caspase-3/7 Green ReadyProbes® Reagent (1:1000 dilution; Molecular Probes) for 15 minutes before being analyzed using the Attune Flow Cytometer. For the measurement of mitochondrial potential as an orthogonal method to assess cell health, the JC-1 Mitochondrial Membrane Potential Assay Kit was utilized according to manufacturer's instructions (Cayman Chemical Company, Ann Arbor, Mich.) and read using the TECAN Safire II Multi-mode plate reader.

Compound 1 Washout Assay: For washout experiments, AML cell lines were plated in U-bottom 96-well plates at a density of 60,000 cells per well. All cells were treated at time zero (t=0) with Compound 1, then, at each time point, cells were resuspended in washout media containing glutarimide at 1000-fold excess over the compound working concentration (eg, 100 µM glutarimide for washout of 100 nM compound treatment). At the end of the incubation period, the plates were centrifuged for 3 minutes at 200 g, supernatant was removed, and cells were resuspended in 100 µL/well 1× Annexin V binding buffer containing Annexin V (2.5 µL/well) and 7-AAD (5 µL/well). Flow cytometry was performed using a BD FACSarray instrument and results were quantified using FlowJo software. At the same time, CTG was added to the 96-(black)well plates and processed as described above in the cell proliferation assay.

Results. Compound 1 Demonstrates Antiproliferative Activity Across a Panel of Acute Myeloid Leukemia Cell Lines. The in vitro antiproliferative activity of Compound 1 was tested in a panel of 11 AML cell lines. The cell lines selected for this study represent a wide range of phenotypes seen in AML patients (Table 1). Compound 1 inhibited cell proliferation in 10 out of 11 AML cell lines assessed, as determined by the quantitative assessment of ATP levels present in the media after 72 hours. The antiproliferative $IC_{50}$ values of Compound 1 ranged between 3 and 75 nM in 10 out of the 11 AML cell lines tested (Table 4). One AML cell line (OCI-AML3) was relatively less sensitive to the growth inhibitory effect of Compound 1 ($IC_{50}$=3 µM). The antiproliferative effects of Compound 1 were also tested in a panel of multiple myeloma and lymphoma cell lines and CLL patient samples (Table 2; Table 3; and Table 4).

TABLE 4

Inhibition of Cell Growth by Compound 1 in a Panel of Acute Myeloid Leukemia Cell Lines in Liquid Culture

| AML Cell Line | AML FAB Classification | Driver Mutation(s) | Proliferation $IC_{50}$ (mean ± SD) (µM) | N |
|---|---|---|---|---|
| KG-1 | M0/1 | FGFR1 Act; NRas | 0.015 ± 0.006 | 81 |
| NB-4 | M3 | PML-RARA | 0.017 ± 0.005 | 82 |
| Kasumi-1 | M2 | RUNX1-RUNX1T1; $KIT^{N822K}$ | 0.021 ± 0.013 | 77 |
| U-937 | M5 | CALM-AF10 | 0.074 ± 0.025 | 73 |
| HNT-34 | M4 | — | 0.003 ± 0.001 | 49 |
| MOLM-13 | M5a | Mll-Af9; $FLT3^{ITD}$ | 0.075 ± 0.033 | 83 |
| HL-60 | M2 | $Myc^{amplified}$; NRas | 0.020 ± 0.010 | 79 |
| KG-1a | M0/1 | FGFR1 Act; NRas | 0.021 ± 0.010 | 81 |
| MV-4-11 | M5 | Mll-Af4; $FLT3^{ITD}$ | 0.029 ± 0.010 | 73 |
| OCI-AML2 | M4 | $DNMT3A^{R635W}$ | 0.057 ± 0.021 | 82 |
| OCI-AML3 | M4 | NPM1c; $DNMT3A^{R882C}$ | 3.397 ± 3.326 | 79 |

Proliferation was assessed using the CellTitre-Glo® assay. Results for cultures incubated with Compound 1 were normalized to results for control cultures for each cell line. The $IC_{50}$ for inhibition of cell growth by Compound 1 was determined for each cell line using ActivityBase software.

Sources: Quentmeier, 2005; American Type Culture Collection website (atcc.org/Products/Cells_and_Microorganisms/By_Disease_Model/Cancer/Source_Tissue/Leuk emia.aspx); Leibniz-Institut DSMZ—Deutsche Sammlung von Mikroorganismen und Zellkulturen GmbH website (dsmz.de/catalogues/catalogue-human-and-animal-cell-lines.html).

TABLE 5

Antiproliferative Effects of Compound 1 in a Panel of Multiple Myeloma and Lymphoma Cell Lines (Continued)

| Hematological Disease | Cell Line | Proliferation $IC_{50}$ (µM) |
|---|---|---|
| Diffuse Large B-cell Lymphoma (activated B-cell like) | U2932 | 0.9045 |
| | RC-K8 | 0.9558 |
| | OCI-LY-10 | >10 |
| Acute Lymphoblastic Leukemia | SR | >10 |
| | Karpas 231 | 0.7896 |
| | MC-116 | >10 |
| | Karpas 299 | >10 |
| Burkitt Lymphoma | DG-75 | >10 |
| | Namalwa | 0.0746 |
| | EB-1 | 0.0663 |
| | BL-70 | 0.3474 |

TABLE 5-continued

Antiproliferative Effects of Compound 1 in a Panel of Multiple Myeloma and Lymphoma Cell Lines (Continued)

| Hematological Disease | Cell Line | Proliferation IC$_{50}$ (µM) |
|---|---|---|
| | Blue-1 | 0.9861 |
| | Daudi | 0.3933 |
| | HS-Sultan | >10 |
| | Ramos | >10 |
| | Raji | >10 |
| | BL-41 | >10 |
| Chronic Lymphocytic Leukemia | Patient samples (n = 3) | 0.01 |

In order to calculate the therapeutic window for Compound 1, the compound was counter-screened against the immortalized (but non-tumorigenic) human hepatocyte-derived cell line THLE-2 (Pfeifer, et al, *Proc Natl Acad Sci USA* 1993 90(11):5123-5127) and against primary human PBMCs. Compound 1 demonstrated reduced antiproliferative activity in THLE-2 (IC$_{50}$~10 µM) compared with AML cell lines, but had some activity against primary human PBMCs (IC$_{50}$=0.12 µM). The Compound 1 therapeutic window for the 10 sensitive AML cell lines as compared to THLE-2 cells ranged from 4.1 (KG-1a) to 57 (HNT-34) (method 1) or from 5.7 (KG-1a) to 79.5 (HNT-34) (method 2); the Compound 1 therapeutic window as compared to PBMCs ranged from 2.6 (KG-1a) to 36 (HNT-34)), or from 1.5 (KG-1a) to 21 (HNT-34) (Table 6).

TABLE 6

Therapeutic Window of Compound 1 in a Panel of Acute Myeloid Leukemia Cell Lines in Liquid Culture Compared with THLE-2 Cells and Peripheral Blood Mononuclear Cells

| AML Cell Line | AUC | N | Therapeutic Window Method 1 | | Therapeutic Window Method 2 | |
|---|---|---|---|---|---|---|
| | | | As Compared with THLE-2 Cells | As Compared with PBMCs | As Compared with THLE-2 Cells | As Compared with PBMCs |
| KG-1 | 65.8 | 4 | 6.0 | 3.8 | 8.3 | 2.2 |
| NB-4 | 14.4 | 7 | 27 | 17 | 38.1 | 10.1 |
| Kasumi-1 | 37.9 | 3 | 10 | 6.6 | 14.5 | 3.8 |
| U-937 | 40.0 | 6 | 9.8 | 6.3 | 13.7 | 3.6 |
| HNT-34 | 6.9 | 2 | 57 | 36 | 79.5 | 21.0 |
| MOLM-13 | 39.6 | 7 | 9.9 | 6.3 | 13.9 | 3.7 |
| HL-60 | 23.7 | 5 | 17 | 11 | 23.2 | 6.1 |
| KG-1a | 96.9 | 5 | 4.1 | 2.6 | 5.7 | 1.5 |
| MV-4-11 | 20.5 | 4 | 19 | 12 | 26.8 | 7.1 |
| OCI-AML2 | 17.9 | 5 | 22 | 14 | 30.7 | 8.1 |
| OCI-AML3 | 563.0 | 6 | 0.70 | 0.45 | 1.0 | 0.3 |

Normal Cells

| | N | AUC Method 1 | AUC Method 2 |
|---|---|---|---|
| THLE-2 | 3 | 393.0 | 549.1 |
| PBMCs | 5 | 251.1 | 145.1 |

Cultures of 11 different AML cell lines were incubated 72 hours with Compound 1 at concentrations of 0.5 nM to 10 µM. Proliferation was assessed using the CellTitre-Glo® assay. Results for cultures incubated with Compound 1 were normalized to results for control cultures for each cell line. Inhibition of cell growth was also determined in THLE-2 cells at Compound 1 concentrations of 0.1 nM to 100 µM and in PBMCs at Compound 1 concentrations of 0.5 nM to 10 µM. The Compound 1 therapeutic window was calculated using area under the curve (AUC; Activity Area [Barretina et al, *Nature* (2012) 483603-607] measurements (in arbitrary units) as determined using GraphPad Prism software for plots of cell proliferation vs concentration and dividing the AUC for the immortalized (but nontumorigenic) human THLE-2 hepatocyte cell line or PBMCs by the AUC for the AML cell line.

Compound 1 Induces Apoptosis in Acute Myeloid Leukemia Cell Lines. The effects of Compound 1 on apoptosis in AML cell lines was investigated. HNT-34 cells were incubated with Compound 1 at concentrations of 0.001 µM. 0.01 µM and 0.1 µM and apoptosis was assessed over time. Results showed that for HNT-34 cells, 100 nM Compound 1 induced maximal apoptosis within 8 to 16 hours of incubation. Next, the induction of apoptosis by Compound 1 in a panel of selected AML cell lines was examined. A marked induction of apoptosis was observed after 24 and 48 hours in 4 out of the 5 cell lines evaluated. As expected, Compound 1 did not induce apoptosis in the Compound 1-insensitive AML line, OCI-AML3.

In order to determine at what time point Compound 1 causes AML cell lines to commit to apoptosis, washout experiments were performed at different time points, and the cell viability was assessed after 72 hours (see schematic in FIG. 30 A). Compound 1 (100 nM) irreversibly committed the cells to apoptosis within 8 to 16 hours of treatment (FIG. 30 B). Washing out 100 nM Compound 1 between 1 and 4 hours reduced the potency (right-shift in the EC$_{50}$ curve) by ~10-fold. Washout at 8 to 16 hours reduced the potency by ~4-fold, and by 24 hours the compound had similar potency to the no washout samples (FIG. 30 B).

Compound 1 Demonstrates Differences in Antiproliferative Effects on Peripheral Blood Mononuclear Cells from Normal Donors Compared with Acute Myeloid Leukemia Cell Lines. The effects of Compound 1 in healthy PBMCs were also assessed. Compound 1 was added to PBMCs from one donor at time zero and assessed at 72 hours. This was compared to PBMCs that were pre-activated and proliferating on anti-CD3 antibody-coated plates for 72 hours before Compound 1 was added and the cells were incubated for an additional 72 hours. HNT-34 cells were used as a sensitive positive control cell line. Peripheral blood mononuclear cells that were pre-activated were resistant to the antiproliferative effects of Compound 1 ($IC_{50}$>10 µM) as determined by CTG and viable cell count. However, Compound 1 did reduce cell proliferation in PBMCs that were not pre-activated, as measured using two methods, CTG and flow cytometry cell counting (CTG $IC_{50}$=0.1 µM; cell count $IC_{50}$=0.5 µM). When antiproliferative activity in non-pre-activated PBMCs was compared to that in HNT-34 cells (CTG $IC_{50}$=0.002 µM; cell count $IC_{50}$=0.004 µM), a therapeutic window of 50 to 125 could be calculated. For the induction of apoptosis, a difference in elevation of caspase 3/7 activity of ~3-fold and a difference in increase of membrane depolarization of ~7-fold at 0.1 µM Compound 1 was seen in HNT-34 cells over the non-pre-activated PBMCs after 72 hours. Similar or greater differences in Compound 1-induced elevation of caspase 3/7 and membrane depolarization were seen between pre-activated PBMCs and HNT-34 cells.

Conclusion. Compound 1 demonstrates strong antiproliferative activity in 10 out of 11 acute myeloid leukemia (AML) cell lines tested. The antiproliferative effects appear to be due to rapid induction of apoptosis. In the most sensitive AML cell line, HNT-34, maximal apoptosis was induced within 8 to 16 hours of incubation with 100 nM Compound 1, as measured by a flow cytometry Annexin V/7-Aminoactinomycin D (7-AAD) assay. The $IC_{50}$ values for the antiproliferative effects ranged from 3 to 75 nM in the 10 sensitive AML cell lines and, for the insensitive line (OCI-AML3), the $IC_{50}$ was 3 µM. The antiproliferative effects of the R- and S-enantiomers of Compound 1 were also evaluated in the panel of 11 AML cell lines. Both enantiomers showed inhibition of cell proliferation similar to that of Compound 1 at 72 hours (data not shown).

Acute myeloid leukemia cell lines are more susceptible to killing by Compound 1 than non-tumorigenic cells from different origins. Compound 1 showed reduced antiproliferative activity in the non-tumorigenic human hepatocyte-derived cell line THLE-2 ($IC_{50}$=~10 µM). Additionally, the antiproliferative effects of Compound 1 were reduced in primary healthy peripheral blood mononuclear cells (PBMCs). Peripheral blood mononuclear cells that were pre-activated were resistant ($IC_{50}$>10 µM) to the effects of Compound 1 on cell proliferation as determined by CellTiter-Glo® (CTG) and viable cell count; however, Compound 1 did reduce cell proliferation in PBMCs that were not pre-activated, as measured using two methods, CTG and flow cytometry cell counting (CTG $IC_{50}$=0.1 µM; cell count $IC_{50}$=0.5 µM). Furthermore, Compound 1 had a differential effect on the induction of apoptosis in tumor cells over healthy donor PBMCs. Apoptosis was evaluated in the HNT-34 cell line and PBMCs using a flow cytometry caspase 3/7 assay and a mitochondrial membrane potential assay. At 100 nM, Compound 1 induced ~3-fold greater caspase 3/7 activation and ~7-fold greater membrane depolarization in HNT-34 cells than in PBMCs.

Example 3

Evaluation of Apoptosis and Viability in Acute Myeloid Leukemia Cell Lines Incubated with Compound 1 In Vitro Using the IncuCyte™ Kinetic Caspase-3/7 Apoptosis Assay Methods. Acute Myeloid Leukemia Cell Line Panel: Human AML cell lines, AML-193, F36-P, GDM-1, HL-60, HNT-34, Kasumi-1, Kasumi-3, KG-1, KG-1a, ML-2, MOLM-13, MUTZ-8, MV-4-11, NOMO-1, OCI-AML2, OCI-AML3, SIG-M5, TF-1, THP-1, and UT-7 were obtained from American Type Culture Collection (ATCC; Manassas, Va.) and Deutsche Sammlung von Mikroorganismen und Zellkulturen (DSMZ) (Germany) cell banks. The AML panel includes cell line(s) from each FAB classification (M0-M7) (Table 7).

TABLE 7

Characteristics of Acute Myeloid Leukemia Cell Lines

| Human AML Cell Line | Disease | Cell Type | Tissue | Gender | Age | FAB Classification | ATCC/ DSMZ Number |
|---|---|---|---|---|---|---|---|
| AML-193 | Acute monocytic leukemia | monocyte | peripheral blood | female | 13 y | M5 | CRL-9589 |
| F-36P | Acute myeloid leukemia | NA | pleural effusion | male | 68 y | M6 | ACC-543 |
| GDM-1 | Myelomonoblastic leukemia | monoblast | peripheral blood | female | 66 y | M4 | CRL-2627 |
| HL-60 | Acute Promyelocytic leukemia | Promyeloblast | peripheral blood | female | 36 y | M2/M3 | CCL-240 |
| HNT-34 | Acute myeloid leukemia | NA | peripheral blood | female | 47 y | M4 | ACC-600 |
| Kasumi-1 | Acute myeloblastic leukemia | myeloblast | peripheral blood | male | 7 y | M2 | CRL-2724 |
| Kasumi-3 | Acute myeloblastic leukemia | lymphoblast | peripheral blood | male | 57 y | M0 | CRL-2725 |
| KG-1 | Acute myelogenous leukemia | macrophage | bone marrow | male | 59 y | M0 | CCL-246 |

TABLE 7-continued

Characteristics of Acute Myeloid Leukemia Cell Lines

| Human AML Cell Line | Disease | Cell Type | Tissue | Gender | Age | FAB Classification | ATCC/ DSMZ Number |
|---|---|---|---|---|---|---|---|
| KG-1a | Acute myelogenous leukemia | Promyeloblast; macrophage | bone marrow | male | 59 y | M0/M1 | ACC-421 |
| ML-2 | Acute Myelomonocytic leukemia | NA | peripheral blood | male | 26 y | M4 | ACC-15 |
| MOLM-13 | Acute myeloid leukemia | NA | peripheral blood | male | 20 y | M5a | ACC-554 |
| MUTZ-8 | Acute myeloid leukemia | NA | peripheral blood | female | 63 y | M4 | ACC-689 |
| MV-4-11 | Biphenotypic B Myelomonocytic leukemia | macrophage | peripheral blood | male | 10 y | M5 | CRL-9591 |
| NOMO-1 | Acute myeloid leukemia | NA | bone marrow | female | 31 y | M5a | ACC-542 |
| OCI-AML2 | Acute myeloid leukemia | NA | peripheral blood | male | 65 y | M4 | ACC-99 |
| OCI-AML3 | Acute myelogenous leukemia | NA | peripheral blood | male | 57 y | M4 | ACC-582 |
| SIG-M5 | Acute monocytic leukemia | NA | bone marrow | male | 63 y | M5a | ACC-468 |
| TF-1 | Erythro-leukemia | erythroblast | bone marrow | male | 35 y | M6 | CRL-2003 |
| THP-1 | Acute monocytic leukemia | monocyte | peripheral blood | male | 1 y | M5 | TIB-202 |
| UT-7 | Acute myeloid leukemia | NA | bone marrow | male | 64 y | M7 | ACC-137 |

Cell Culture Conditions: Cell lines were maintained in growth media containing 20% fetal bovine serum (FBS) (Hyclone Cat no. SH30910.03, Lot no. AZF188864; Corning REFno. 35-010-CV, Lot no. 35010124) supplemented with or without 10 ng/mL human recombinant granulocyte-macrophage colony stimulating factor (Sigma-Aldrich Cat no. SRP3050) (Table 8). Medium was purchased from ATCC (Cat no. 30-2001, 30-2002, 30-2003, 30-2005) and Gibco (REF no. 12561-056). Human recombinant granulocyte macrophage colony stimulating factor (GM-CSF) was expressed in *Escherichia coli*. The cell doubling times for each cell line were provided by ATCC and DSMZ. Cells were maintained in humidified incubators at 5% carbon dioxide ($CO_2$). All cell lines were acclimated to Eagle's minimal essential medium (EMEM)+20% FBS with or without GM-CSF over 2 to 4 weeks prior to live cell imaging using IncuCyte Zoom (Essen Biosciences). The use of EMEM was necessary to eliminate background fluorescence caused by riboflavin in most media.

TABLE 8

Growth Conditions

| Human AML Cell Line | Culture Medium | Reported Doubling Time (hr) |
|---|---|---|
| AML-193 | IMDM + 20% FBS + 10 ng/mL GM-CSF | 50-60 |
| F-36P | RPMI 1640 + 20% FBS + 10 ng/mL GM-CSF | 24-36 |
| GDM-1 | RPMI 1640 + 20% FBS | 40-50 |
| HL-60 | RPMI 1640 + 20% FBS | 40 |
| HNT-34 | RPMI 1640 + 20% FBS | 40 |
| KASUMI-1 | RPMI 1640 + 20% FBS + 10 ng/mL GM-CSF | 40-72 |
| KASUMI-3 | RPMI 1640 + 20% FBS + 10 ng/mL GM-CSF | 55-60 |
| KG-1 | RPMI 1640 + 20% FBS | 38 |
| KG-1a | RPMI 1640 + 20% FBS | 50 |
| ML-2 | RPMI 1640 + 20% FBS | 60 |
| MOLM-13 | RPMI 1640 + 20% FBS | 50 |
| MUTZ-8 | MEM alpha + 20% FBS + 10 ng/mL GM-CSF | 72-120 |
| MV-4-11 | RPMI 1640 + 20% FBS | 50 |
| NOMO-1 | RPMI 1640 + 20% FBS | 35 |
| OCI-AML2 | MEM alpha + 20% FBS | 30-50 |
| OCI-AML3 | DMEM + 20% FBS | 35-40 |
| SIG-M5 | IMDM + 20% FBS | 72 |
| TF-1 | RPMI 1640 + 20% FBS + 10 ng/mL GM-CSF | 70 |
| THP-1 | RPMI 1640 + 20% FBS | 35-50 |
| UT-7 | MEM alpha + 20% FBS + 10 ng/mL GM-CSF | 70 |

Derivation of Red-Labeled Acute Myeloid Leukemia Cell Lines: Twelve cell lines, including AML-193, HL-60, KG-1, ML-2, MOLM-13, MV-4-11, NOMO-1, OCI-AML2, OCI-AML3, SIG-M5, TF-1, and THP-1, were stably transduced with Red lentivirus. Cells were plated in 6-well plates in growth media, incubated with 8 μg/mL polybrene (EMD Millipore Cat no. TR-1003-G) followed by infection with CellPlayer™ NucLight™ Red-lentiviral particles (Essen Biosciences Cat no. 4478) at a multiplicity of infectivity (MOI) of 0.5 to 2.5 for 24 hours. MOI refers to the ratio of virus particles to cells. Virus-containing media was replaced with fresh growth media and incubated for an additional 24 to 48 hours, followed by selection with Zeocin (500 to 2000 µg/mL), a derivative of bleomycin (Life Technologies-Invitrogen Cat no. R250-01). Cells were selected with fresh Zeocin every 3 to 4 days for 3 to 8 weeks. Cells were periodically viewed using fluorescent microscopy for nuclear-restricted red fluorescence. Zeocin selection was terminated once the population was confirmed to stably fluoresce red. All Red-labeled cell lines were acclimated to EMEM containing 20% FBS, with or without GM-CSF supplementation, allowing for optimal live cell imaging.

Incubation of Cell Cultures with Compound 1: Compound 1 was provided for studies by Celgene chemistry group at a stock concentration of 30 mM in 20 µL dimethyl sulfoxide (DMSO) frozen. Costar 96-well cell culture plates (Corning Cat no. 3595) were coated with 100 µL of 10 µg/mL fibronectin (Sigma-Aldrich Cat no. F1141) for 4 hours at 37° C. and immediately used or refrigerated overnight for later use. Cells (3000 to 6000 cells) were plated in growth medi in fibronectin-coated 96-well plates and incubated for a minimum of a few hours to overnight. Cells were incubated with a 12-point concentration response in triplicate with Compound 1 (0 to 10 µM) including DMSO and Media controls. A 3-fold serial dilution of Compound 1 starting from a concentration of 200 µM in 0.6% DMSO (diluted in Media) was performed. For most sensitive cell lines, a 3-fold serial dilution of Compound 1 starting from a concentration of 20 µM in 0.6% DMSO (diluted in media) was performed. A volume of 5 µL or 10 µL for each dilution was added to 100 µL or 200 µL cells, respectively (0.3% DMSO final) and incubated for live cell imaging.

Live Cell Imaging on IncuCyte Zoom: Following incubation of cells with Compound 1, diluted Caspase 3/7 reagent (Essen Biosciences Cat no. 4440) is added to each well. The Caspase-3/7 reagent couples the activated caspase-3/7 recognition motif (DEVD) to NucViewTM488, a DNA intercalating dye. The cleavage of substrate by activated caspase-3/7 results in the release of the DNA dye and green fluorescent staining of nuclear DNA. This allows imaging of cells undergoing caspase-3/7 mediated apoptosis over time. Caspase-3/7 activation was quantified using the IncuCyte™ ZOOM basic analyzer. Red-labeled cell lines were also imaged over time using the IncuCyte™ ZOOM basic analyzer, for determination of both cell doubling time and Compound 1 effect on cell viability. Experiments were performed at least two times in each cell line.

Dose-Response Data Analysis: For each cell line incubated with a concentration range of Compound 1 (0 to 10 µM), at time points 12, 24, 48, 72, and 96 hours, the area under the curve (AUC) of cell growth (Total Red Integrated Intensity (RCU×µm²/well) or Red Object Count (1/Well)) and cell death (Green Object Count (1/well)) was calculated by the "trapz" function in the R 'pracma' package (Borchers H W. Practical Numerical Math Functions. R Package version 1.8.6. https://cran.r project.org/web/packages/pracma/pracma.pdf. p 340-341. Nov. 27, 2015. Accessed 1 Feb. 2016) for each concentration and replicate. Next, a 4 parameter log-logistic model was used to determine relative EC50 at each time point by the 'drm' function from the R 'drc' package (Ritz C, Streibig J C. Bioassay Analysis using R. *J. Statist. Software* 2005; 12(5): 1-22). Goodness of fit was measured by R squared (coefficient of determination or the amount of variation explained by the model fit) of ≥80%, and $EC_{50}$ parameter was assessed by having a ratio of standard error to the parameter of ≤40%, and the presence of at least one concentration point above and below the reported $EC_{50}$.

Green Objects (1/well) versus time and Total Red Integrated Intensity (RCU×µm²/well) or Red Object Count (1/well) versus time for RFP-labeled cells were plotted using the graphing capabilities in the IncyCyte ZOOM device software from Essen Biosciences, Inc.

Results

Quantification of Apoptotic Responses in Panel of Acute Myeloid Leukemia Cell Lines Incubated with Compound 1. Real-time imaging of apoptosis, as measured by caspase 3/7 activation, was performed in AML cell lines incubated with a range of concentrations of Compound 1. Table 9 shows the average $EC_{50}$ values for Compound 1-mediated caspase 3/7 activation in AML cell lines at times 24, 48, 72, and 96 hours.

Different sensitivities to apoptosis induction by Compound 1 were observed across the twenty AML cell lines. As all cell lines, except THP-1, had at least one successful curve fit at 48 hours, this time was used to define the relative sensitivities of cell lines.

Eight cell lines (HNT-34, Kasumi-3, HL-60, ML-2, MV4-11, KG-1, MUTZ-8, GDM-1) had $EC50_{48hr}$ below 0.05 µM (range 0.004 to 0.049 µM); these lines were categorized as highly sensitive, having an average $EC50_{48hr}$ of 0.027 µM. HNT-34 was the most sensitive cell line with an $EC50_{48hr}$ of 0.004 µM.

Seven cell lines (OCI-AML-2, AML-193, SIG-M5, Kasumi-1, TF-1, Nomo-1, KG-1a) had $EC50_{48hr}$ between 0.05 µM and 0.2 µM (range 0.081 to 0.145 µM); these lines were categorized as moderately sensitive, having an average $EC50_{48hr}$ of 0.114 µM.

Four cell lines (UT-7, F36-P, MOLM-13, OCI-AML3) had $EC50_{48hr}$ between 0.2 µM and 1 µM (range 0.231 to 0.896 µM), having an average $EC50_{48hr}$ of 0.458 µM. One cell line (THP-1) had an $EC50_{48hr}$ greater than 10 µM. These cell lines were categorized as least sensitive.

Different time kinetics of caspase 3/7 activation (apoptosis induction) by Compound 1 was observed across the AML cell panel.

Apoptotic responses were observed as early as 12 hours in the 8 most sensitive cell lines ($EC50_{12hr}$ range 0.053 to 0.227 µM). Although an $EC50_{12hr}$ was not observed in HNT-34, HL-60, and MUTZ-8 cell lines due to lack of 'good curve fits', caspase 3/7 activation was observed.

By 24 hours, 14 of 20 cell lines had successful curve fits ($EC50_{24hr}$ range 0.007 to 0.916 µM). Two cell lines (HNT-34 and Kasumi-3) had $EC50_{24hr}$ below 0.05 µM, seven cell lines (HL-60, ML-2, MV-4-11, KG-1, MUTZ-8, SIG-M5, and NOMO-1) had $EC50_{24hr}$ between 0.05 µM and 0.2 µM and five cell lines (KG-1a, AML-193, GDM-1, OCI-AML2, and MOLM-13) had $EC50_{24hr}$ greater than 0.2 µM.

Increased potency of Compound 1 was generally observed across the AML cell panel at later time points. $EC50_{72hr}$ and $EC50_{96hr}$ ranged from 0.003 to 0.971 µM and 0.001 to 0.418 µM, respectively. By 72 hours, 11 of 20 cell lines (including HNT-34) had an $EC50_{72hr}$ of ≤0.05 µM; 4 of 20 cell lines had an $EC50_{72hr}$ between 0.05 to 0.20 µM; 4 of 20 cell lines had an $EC50_{72hr}$ between 0.2 to 1 µM. Similar results were observed at 96-hour time point.

TABLE 9

Average $EC_{50}$ Values of Compound 1-induced Apoptosis in Acute Myeloid Leukemia Cell Lines

| AML Cell Line | Compound 1-induced Apoptosis $EC_{50}$ (μM) | | | | | Rank at 24 hr | Rank at 48 hr |
|---|---|---|---|---|---|---|---|
| | 12 hr | 24 hr | 48 hr | 72 hr | 96 hr | | |
| HNT-34 | NF | 0.007 | 0.004 | NF | 0.002 | 1 | 1 |
| Kasumi-3 | 0.054 | 0.010 | 0.004 | 0.003 | 0.001 | 2 | 2 |
| HL-60 | NF | 0.073 | 0.015 | 0.008 | NF | 5 | 3 |
| ML-2 | 0.179 | 0.062 | 0.031 | 0.021 | 0.025 | 3 | 4 |
| MV-4-11 | 0.227 | 0.167 | 0.032 | 0.016 | 0.017 | 9 | 5 |
| KG-1 | 0.053 | 0.108 | 0.039 | 0.026 | 0.025 | 7 | 6 |
| MUTZ-8 | NF | 0.088 | 0.040 | 0.018 | 0.015 | 6 | 7 |
| GDM-1 | 0.110 | 0.313 | 0.049 | 0.033 | 0.025 | 12 | 8 |
| OCI-AML2 | NF | 0.436 | 0.081 | 0.041 | 0.038 | 13 | 9 |
| AML-193 | NF | 0.254 | 0.089 | 0.047 | 0.060 | 11 | 10 |
| SIG-M5 | NF | 0.148 | 0.097 | 0.050 | 0.033 | 8 | 11 |
| Kasumi-1 | NF | NF | 0.124 | 0.254 | 0.055 | 15 | 12 |
| TF-1 | NF | NF | 0.129 | 0.065 | 0.064 | 16 | 13 |
| Nomo-1 | NF | 0.063 | 0.133 | 0.084 | 0.066 | 4 | 14 |
| KG-1a | NF | 0.226 | 0.145 | 0.186 | NF | 10 | 15 |
| UT-7 | NF | NF | 0.231 | 0.218 | 0.168 | 17 | 16 |
| F36-P | NF | NF | 0.335 | 0.252 | 0.229 | 18 | 17 |
| MOLM-13 | NF | 0.916 | 0.368 | 0.156 | 0.079 | 14 | 18 |
| OCI-AML3 | NF | NF | 0.896 | 0.971 | 0.418 | 19 | 19 |
| THP-1 | NF | NF | NF | NF | NF | 20 | 20 |

Twenty human AML cell lines were incubated with Compound 1 dose range (0 to 10 μM) and Green Objects (cells undergoing apoptosis) were imaged over time, as described above. Average $EC_{50}$ values were determined from calculated AUCs (area under the curve) at time points 12, 24, 48, 72, and 96 hours, as described above. Ranking of cell lines based on EC50 value are shown at 24- and 48-hour time points.

Quantification of Cell Viability in Panel of Red-Labeled Acute Myeloid Leukemia Cell Lines Incubated with Compound 1: A sub-panel of twelve Red-labeled cell lines was evaluated for Compound 1 effects on cell viability over time using IncuCyte Zoom live cell imaging. Table 10 shows the average $EC_{50}$ values for Compound 1 mediated cell viability reduction in AML cell lines at time points 24, 48, 72, and 96 hours.

Different sensitivities to cell viability reduction by Compound 1 were observed across the AML cell lines. As all cell lines, except THP-1, had at least one successful curve fit at 96 hours, this time was used to define the relative sensitivities of cell lines.

Seven cell lines (AML-193, ML-2, HL-60, KG-1, NOMO-1, MV-4-11, OCI-AML2) had $EC50_{96hr}$ below 0.05 μM (range 0.002 to 0.040); these lines were categorized as highly sensitive, having an average $EC50_{96hr}$ of 0.015 μM. AML-193 was the most sensitive cell line with an $EC50_{96hr}$ of 0.002 μM.

Four cell lines (TF-1, THP-1, SIG-M5, OCI-AML3) had an $EC50_{96hr}$ between 0.05 and 0.20 μM (range 0.058 to 0.186 μM); these lines were categorized as moderately sensitive, having an average $EC50_{96hr}$ of 0.121 μM.

Only one cell line (MOLM-13) had an $EC50_{96hr}$ greater than 0.2 μM ($EC50_{96hr}$ of 0.248 μM). This cell line was categorized as least sensitive.

TABLE 10

Average $EC_{50}$ Values for Compound 1 Effect on Cell Viability in Red-labeled Acute Myeloid Leukemia Cell Lines

| Red-lableled AML Cell Line | Inhibition of Cell Viability $EC_{50}$ (μM) | | | | Rank at 48 hr | Rank at 72 hr | Rank at 96 hr |
|---|---|---|---|---|---|---|---|
| | 24 hr | 48 hr | 72 hr | 96 hr | | | |
| AML-193 | 0.010 | 0.004 | 0.003 | 0.002 | 1 | 1 | 1 |
| ML-2 | NF | NF | 0.004 | 0.004 | NR | 2 | 2 |
| HL-60 | NF | 0.009 | 0.007 | 0.006 | 3 | 3 | 3 |
| KG-1 | NF | 0.007 | 0.007 | 0.007 | 2 | 3 | 4 |
| NOMO-1 | NF | 0.019 | 0.017 | 0.017 | 4 | 5 | 5 |
| MV4-11 | NF | 0.040 | 0.027 | 0.026 | 6 | 6 | 6 |
| OCI-AML2 | 0.387 | 0.083 | 0.042 | 0.040 | 7 | 8 | 7 |
| TF-1 | NF | 0.030 | 0.036 | 0.058 | 5 | 7 | 8 |
| THP-1 | NF | NF | NF | 0.061 | NR | NR | 9 |
| SIG-M5 | NF | NF | 0.156 | 0.178 | NR | 9 | 10 |
| OCI-AML3 | NF | NF | 0.180 | 0.186 | NR | 10 | 11 |
| MOLM-13 | NF | 0.143 | 0.208 | 0.248 | 8 | 11 | 12 |

Twelve Red-labeled human AML cell lines, established as described above, were incubated with Compound 1 dose range (0 to 10 μM) and Red fluorescence or Object count was imaged over time, as described above. $EC_{50}$s for cell viability were determined, as described above, at time points 24, 48, 72, and 96 hours. Ranking of cell lines are shown at 48, 72, and 96 hour time points.

Conclusion. Studies were performed to evaluate the effects of Compound 1 on apoptosis in a panel of twenty acute myeloid leukemia (AML) cell lines, using the IncuCyte™ Kinetic Caspase-3/7 Apoptosis Assay. Additionally, thirteen Red-labeled AML cell lines were established to evaluate the effects of Compound 1 on cell viability, using the IncuCyte™ System to quantify total viable cells. Conclusions from studies include:

Different sensitivities to apoptosis induction by Compound 1 were observed across the twenty AML cell lines Eight cell lines (HNT-34, Kasumi-3, HL-60, ML-2, MV4-11, KG-1, MUTZ-8, GDM-1) were defined as highly sensitive, with an average $EC_{50}$ of 0.027 μM at 48 hours (range 0.004 to 0.049 μM).

Seven cell lines (OCI-AML-2, AML-193, SIG-M5, Kasumi-1, TF-1, Nomo-1, KG-1a) were defined as moderately sensitive, with an average $EC_{50}$ of 0.114 μM at 48 hours (range 0.081 to 0.145 μM).

Five cell lines (UT-7, F36-P, MOLM-13, OCI-AML3, THP-1) were defined as least sensitive, with $EC_{50}$ values ranging from 0.231 to 0.896 μM for UT-7, F36-P, MOLM-13, and OCI-AML3 ($EC_{50}$ greater than 10 μM for THP-1).

Different kinetics of apoptosis induction by Compound 1 were observed across the AML cell panel Apoptotic responses were observed as early as 12 hours in the 8 most sensitive cell lines ($EC50_{12hr}$ range 0.053 to 0.227 μM, for the 5 lines with curve fits).

By 72 hours, 19 of 20 cell lines responded to Compound 1, with $EC50_{72hr}$ and $EC50_{96hr}$ ranging from 0.003 to 0.971 μM and 0.001 to 0.418 μM, respectively.

Only THP-1 cell line had an EC50 greater than 10 μM at all time points.

Different sensitivities to Compound 1, as measured by cell viability, were also observed across a subpanel of twelve Red-labeled AML cell lines Seven cell lines (AML-193, ML-2, HL-60, KG-1, NOMO-1, MV-4-11, OCI-AML2) had $EC50_{96hr}$ below 0.05 μM (range 0.002 to 0.040); these lines were categorized as highly sensitive, having an average $EC50_{96hr}$ of 0.015 μM.

Four cell lines (TF-1, THP-1, SIG-M5, OCI-AML3) had an $EC50_{96hr}$ between 0.05 and 0.20 μM (range 0.058 to 0.186 μM); these lines were categorized as moderately sensitive, having an average $EC50_{96hr}$ of 0.121 μM.

Only one cell line (MOLM-13) had an $EC50_{96hr}$ greater than 0.2 μM ($EC50_{96hr}$ 0.248 μM). This cell line was categorized as least sensitive.

Example 4

Antitumor Activity in Bone Marrow Samples from Donors with Acute Myeloid Leukemia Patient Samples: The study included bone marrow (BM) samples from adult patients over 18 years of age who were diagnosed with AML. Samples were analyzed in two different batches with the first batch containing 10 patients (donors assigned identification codes containing CG1) and the second comprising the remaining 20 donors (assigned identification codes containing CG3). Clinical data for the first batch of donors is presented in Table 11. Corresponding clinical data was not available for the second batch of 20 patient samples at the time of writing.

TABLE 11

Donor Clinical Data (CG1 donors)

| | Indication | Age | Sex | Line of Treatment | Treatment | Clinical Response |
|---|---|---|---|---|---|---|
| PM_CG1-001 | AML | 48 | Male | 1 | Cytarabine and Idarubicin | Unknown |
| PM_CG1-002 | AML | 63 | Male | 1 | Cytarabine and Idarubicin | Partial response |
| PM_CG1-003 | AML | 75 | Female | 1 | Cytarabine and Fludarabine | Resistant |
| PM_CG1-004 | AML | 74 | Female | 1 | Hydrea | Death during induction therapy |
| PM_CG1-005 | AML | 55 | Female | 1 | Cytarabine and Idarubicin | Unknown |
| PM_CG1-006 | AML | 69 | Male | 1 | Cytarabine and Fludarabine | Unknown |
| PM_CG1-007 | AML | 83 | Male | 1 | Cytarabine and Fludarabine | Death during induction therapy |
| PM_CG1-009 | AML | 33 | Male | 1 | Cytarabine and Idarubicin | Unknown |
| PM_CG1-010 | AML | 70 | Female | 1 | Ara-C + (Volasertib vs Placebo) | Unknown |
| PM_CG1-013 | AML | 55 | Male | 1 | Cytarabine and Idarubicin | Unknown |

Experimental Study Design: To evaluate and characterize the ex vivo pharmacology of Compound 1 in malignant cells and normal lymphocytes of bone marrow samples from thirty donors with acute myeloid leukemia using a flow cytometry-based platform (ExviTech) (Bennett, et al *Clin Lymphoma Myeloma Leuk* 2014 August; 14(4):305-318).

On Day 1, the donor sample was received. A small part was separated for validation, and the majority was diluted with culture medium (Roswell Park Memorial Institute (RPMI) 1640) and plated into 96-well plates previously prepared with a range of Compound 1 concentrations. The number of live leukemic cells seeded in each well was fixed between 8000 and 32,000, depending on the percentage of leukemic cells for each sample. The plates were incubated for 24, 48, or 96 hours. Antibodies anti-D34, anti-CD117, anti-HLA-DR, anti-CD45, anti-CD14, anti-CD64, anti-CD13, anti-CD11b) or Annexin V were added to identify leukemic cells using a gating strategy based on forward scatter (FSC) or side scatter (SSC) and expression or lack of expression of different surface markers. The monoclonal antibody selection was performed to optimize the identification of leukemic cells in each sample. The aim of this analysis was not the phenotypic characterization but only the identification of these cells. Accordingly, the markers that Euroflow (van Dongen et al, *Leukemia* 2012 September; 26(9):1908-1975) has designated as the "backbone markers" for AML (CD34, CD45, CD117) and human leukocyte antigen-DR (HLA-DR) were included in the combination. They allowed the identification of the leukemic cells in almost 90% of AML patients. Additional panels, CD34/CD14/CD64/CD45 and CD34/CD11b/CD13/CD45, were also used to complete the identification of the myeloid leukemic population. This allowed for the selection of the two best antibodies for unequivocal identification of the pathological cell population in each particular sample.

Live leukemic cells were identified by their light scattering properties classified as high, intermediate, or low (eg, $FSC^{int/hi}/SSC^{int}$) in the absence of Annexin V fluorescein isothiocyanate (FITC) staining. Forward scatter/side scatter selection was performed to exclude debris. The average percentage of cell viability on receipt of the sample was greater than 50% (samples were only processed if the viability was greater than 50%). In some AML donor samples, sufficient normal, non-tumoral lymphocyte cells could be counted, and the effect of Compound 1 was measured in this cell population. Non-tumoral lymphocytes were identified by bright expression of CD45, $FSC^{low}/SSC^{low}$ and absence of myeloid markers (CD117, CD11b, and CD13).

Detailed descriptions of methods used have been published previously (Bennett, et al *Clin Lymphoma Myeloma Leuk* 2014 August; 14(4):305-318). Briefly, BM samples were extracted under sterile conditions in hospitals of origin and were received within 24 hours of extraction. Initial analysis evaluated the number of pathological cells and their viability. Different volumes of sample (1 µL, 3 µL, 5 µL, and 7 µL) were transferred in duplicate into a 96-well plate. To lyse red blood cells, 180 µL of ammonium chloride lysis solution (2 g $KHCO_3$, 16.58 g $NH_4Cl$, 0.074 g disodium ethylenediaminetetraacetic acid ·$2H_2O$, and $H_2O$ adjusted to 1 L) was added to each well. Following a 10-minute incubation period at 4° C., each plate was centrifuged for 5 minutes at 1200 rpm, and the supernatant removed. The lysis step was performed twice. To analyze, 20 µL of a combination of Annexin V-FITC (Immunostep, Salamanca, Spain), binding buffer (BB; 2.4 g 4-[2-hydroxyethyl]-1-piperazineethanesulfonic acid [HEPES], 8.19 g NaCl, 0.37 g $CaCl_2$, and $H_2O$ adjusted to 1 L), and the following monoclonal antibodies (MoAbs) were added to each well: CD117 (clone 104D2)-PE (Becton Dickinson, San Jose, Calif.), CD34 (clone 581)-PerCP (BioLegend, San Diego, Calif.), HLA-DR (clone L243)-PB (BioLegend), and CD45 (HI30)-PO (Life Technologies, Carlsbad, Calif.) (van Dongen et al, *Leukemia* 2012b September; 26(9):1899-1907). After 15 minutes of incubation at room temperature in the dark, a wash step was performed using BB solution. The pellet was resuspended in 30 µL BB for analysis in ExviTech platform. Cell count and viability were then computed, and the optimal volume of sample to use per well was determined.

Assay Preparation: The whole sample was diluted with RPMI 1640 medium, supplemented with 20% (vol/vol) fetal bovine serum (Thermo Scientific, Waltham, Mass.), 2% HEPES, 1% antibiotic (Zell Shield, Labclinics, Barcelona, Spain), and 2 µM L-glutamine (Lonza, Hopkinton, Mass.) to a final volume of 60 µL per well. The mixture was dispensed into 96-well plates containing Compound 1 using a Multidrop Combi Smart (Thermo Scientific, Waltham, Mass.). Plates containing Compound 1 were prepared in advance using an Echo 550 Liquid Handler (LabCyte, Sunnyvale, Calif.). For Compound 1, 12 concentrations (0.0016 to 40 µM), adjusted to cover the range of activities across donors, were used. Compound 1 was analyzed in 30 donor samples. The plates were incubated for 24, 48, and 96 hours at 37° C. in humidified air containing 5% $CO_2$.

Isolating the Leukocyte Population: To prepare the sample for analysis at the end of the incubation, the red cell population was lysed following the same procedure as described above. Next, 20 µL of a combination of the 2 best MoAbs for identifying the leukemic cell population for the sample (as determined previously) and Annexin V-FITC were added to each well, and the plates were incubated for 15 minutes at room temperature in the dark. A wash step was performed using BB, and the pellet was resuspended in 20 µL of BB for analysis in ExviTech platform.

ExviTech Platform: This novel flow cytometry-based system incorporates a CyAn advanced digital processing cytometer (Beckman Coulter, Brea, Calif.) and a End Point Sampler (EPS) plate handler (Saryna Technologies, San Diego, Calif.). The EPS aspirated the contents of each well of the assay plate, and it delivered the contents to the flow cell of the cytometer. Each 96-well assay plate was collected as a single flow cytometry standard (.fcs) file from the CyAn cytometer. The EPS was run from the same computer as the cytometer, recording a second file for each plate. This timing file was integrated with the .fcs file for data analysis by a proprietary software program, FCS Analyzer (Saryna Technologies). This program was designed to separate the acquired data from the cytometer into specific groups and assign well numbers to each group. Each 96-well plate was then analyzed as a single file, and each well could be examined individually as needed.

Flow Cytometry Data Analysis: Summit software (Beckman Coulter) was used for the initial analysis. Identification of pathological cells was performed using a gating strategy based on FSC/SSC and expression or lack of expression of the different MoAb markers. Depletion was measured as the difference in the number of live cells in a well with compound versus the control wells with vehicle alone. Hence, once the pathological cell subset was identified, Annexin V and appropriate FSC/SSC were used to exclude dying cells and to measure only the number of live cells in the drug wells compared with the control wells (Koopman et al, *Blood* 1994 Sep. 1; 84(5):1415-1420). Additionally, changes in FSC and SSC helped identify and discard necrotic cells, deeming the use of propidium iodide unnecessary. Once the above parameters were obtained, the FCS Analyzer was used to quantify the effect of each individual concentration on the samples.

Data Analysis: Individual data points were obtained and used to calculate $EC_{50}$ and $E_{max}$. A four parameter logistic model (Sigmoidal Dose-Response Model, IDBS XLFit) was used to determine the fitted parameters:

$$y=(A+((B-A)/(1+((x/C)^\wedge D))))$$

A=YMin
B=YMax
C=$EC_{50}$
D=Slope factor
Y=Percentage of cell counts relative to positive control All inhibition curves were processed and evaluated using Activity Base XE (IDBS). In the cases where a plateau could not be experimentally determined, the extrapolated $EC_{50}$ value returned by Activity Base XE was changed to NC (not calculated). In the cases where the raw data were too noisy to conform to the expected sigmoidal geometry, the fitted parameters returned by Activity Base XE were changed to NC.

The Activity Area is calculated as the percentage of the area under the curve (AUC; calculated from XLFit formula: xf4_AreaXStartXEnd(<fit cell>, <min conc>, <max_conc>)) divided by total theoretical area (the rectangle bounded by the concentration range and the maximum theoretical inhibition: Max Inhibition*(max conc-min conc)). As a result, the Activity Area is high for inactive compounds (where all points are near 100) and lower for active compounds.

$E_{max}$ was calculated by subtracting the fitted parameter YMin from 100%, whereby maximum efficacy (complete depletion of leukemic cells) is 100% (eg, YMin=zero).

The hierarchical clustering and heat map of AUC data were generated utilizing the R statistical program (http://www.R-project.org). The column-side dendrogram was generated using the average linkage method, and the Euclidean distances between the samples calculated based on the standardized AUC data within each time point. The heat map is shown with the AUC data in the original scale and colored in a red/green scheme; ie, red means higher AUC and green means lower AUC.

A paired two-tailed Student's t-test was used to determine the statistical significance of the difference between the AUC of tumor compared to lymphoid cells.

Results

The effects of Compound 1 at 24, 48, and 96 hours were evaluated in 30 fresh (time of culture <24 hours from bone marrow extraction) AML bone marrow samples (Table 12). For these assays, bone marrow samples were cultured ex vivo without separation in order to maintain the bone marrow microenvironment (stromal, erythrocyte, immune cells, serum proteins, etc) rather than as isolated leukocytes. Leukocytes were only isolated after incubation when the Compound 1-induced antiproliferative effect had already occurred. At this point, leukemic and normal cell populations were identified by flow cytometry using the "backbone" antibody markers for AML (van Dongen, et al. *Leukemia* 2012 September; 26(9): 1908-1975), and the percentage viability of these populations was established using the light scatter properties and Annexin V staining of these cells. Interestingly, 26 out of 30 patient samples were sensitive to Compound 1, with the compound showing reduced efficacy in only 4 donors, where a large percentage of leukemic cells remained viable after both 24 and 48 hours. The mean $EC_{50}$ of Compound 1 in the group of sensitive patient samples was 21 nM (range 2 to 160 nM) across all three time points (Table 12). The ex vivo efficacy of Compound 1 was time- and concentration-dependent (Table 12). Three out of the four patient samples categorized as insensitive displayed higher $EC_{50}$ values than sensitive samples, and all four consistently showed weaker efficacy as measured by an inability to deplete leukemic blasts by more than 68% at 24 and 48 hours. In the sensitive patient samples, leukemic cell killing was rapid and very efficient; Compound 1 was able to deplete on average >82% of leukemic cells by 24 hours, >92% by 48 hours, and >98% by 96 hours. Notably, at all time points, the antiproliferative effect of Compound 1 on normal lymphocytes was significantly decreased (2- to 5-fold) compared to the effects observed in tumor cells, suggesting tumor-specific activity of Compound 1 (FIG. 31). In patient samples where sufficient normal lymphocytes could be counted, the $E_{max}$ averaged 46% to 76% from 24 to 96 hours.

TABLE 12

| Donor ID | Cell Line (LIVE) | Incubation Time (hours) | Activity Area | $EC_{50}$ | $E_{max}$ | Curve Slope | $r^2$ |
|---|---|---|---|---|---|---|---|
| PM_CG1_001 | Leukemic | 24 | 11.4 | 0.003 | 88.6 | -1.159 | 0.991 |
| | | 48 | 0.0 | <0.00168 | 100.0 | -3.235 | 0.995 |
| | | 96 | 0.1 | 0.006 | 100.0 | -1.231 | 0.977 |
| | Lymphoid | 24 | 41.5 | 0.020 | 58.6 | -1.324 | 0.953 |
| PM_CG1_002 | Leukemic | 24 | 19.3 | 0.076 | 81.0 | -1.662 | 0.956 |
| | | 48 | 3.1 | 0.021 | 97.0 | -3.239 | 0.988 |
| | | 96 | 0.1 | 0.006 | 100.0 | -1.231 | 0.977 |
| | Lymphoid | 24 | 39.0 | NC | 82.5 | -0.267 | 0.888 |
| | | 48 | 20.6 | 0.033 | 79.5 | -1.564 | 0.985 |
| | | 96 | 10.2 | 0.019 | 89.9 | -1.499 | 0.986 |
| PM_CG1_003 | Leukemic | 24 | 16.4 | 0.013 | 83.7 | -1.308 | 0.969 |
| | | 48 | 0.1 | <0.00168 | 99.9 | -2.990 | 0.885 |
| | | 96 | 0.0 | <0.00168 | 100.0 | -5.030 | 1.000 |
| PM_CG1_004 | Leukemic | 24 | 18.3 | 0.013 | 81.8 | -5.375 | 0.959 |
| | | 48 | 7.3 | 0.002 | 92.7 | -2.025 | 0.986 |
| | | 96 | 2.0 | 0.009 | 98.0 | -15.474 | 0.869 |
| | Lymphoid | 24 | 36.3 | 0.019 | 63.7 | -1.640 | 0.936 |
| | | 48 | 34.3 | 0.031 | 66.0 | -1.136 | 0.958 |
| | | 96 | 22.2 | 0.031 | 77.9 | -1.568 | 0.951 |
| PM_CG1_005 | Leukemic | 24 | 2.9 | 0.019 | 97.1 | -3.170 | 0.926 |
| | | 48 | 0.3 | 0.007 | 99.8 | -5.116 | 0.996 |
| | | 96 | 0.1 | 0.006 | 99.9 | -5.522 | 0.986 |
| | Lymphoid | 24 | 60.8 | 0.089 | 39.5 | -1.166 | 0.901 |
| | | 48 | 42.3 | 0.032 | 58.4 | -0.778 | 0.933 |
| | | 96 | 19.0 | 0.033 | 81.5 | -1.016 | 0.988 |
| PM_CG1_006 | Leukemic | 24 | 10.2 | 0.095 | 90.3 | -1.504 | 0.926 |
| | | 48 | 4.1 | 0.045 | 96.0 | -2.219 | 0.996 |
| | | 96 | 0.1 | 0.018 | 100.0 | -2.709 | 0.977 |
| | Lymphoid | 24 | 52.3 | 0.149 | 48.8 | -0.996 | 0.843 |
| | | 48 | 31.1 | 0.061 | 69.1 | -1.621 | 0.988 |
| | | 96 | 17.3 | 0.045 | 83.0 | -1.524 | 0.977 |
| PM_CG1_007 | Leukemic | 24 | 5.3 | 0.033 | 94.8 | -2.382 | 0.988 |
| | | 48 | 0.3 | 0.014 | 99.8 | -2.033 | 0.997 |
| | | 96 | 0.0 | 0.008 | 100.0 | -3.035 | 0.996 |
| PM_CG1_009 | Leukemic | 24 | 5.1 | 0.036 | 95.0 | -2.170 | 0.916 |
| | | 48 | 0.7 | 0.012 | 99.3 | -3.125 | 0.997 |
| | | 96 | 0.2 | 0.011 | 99.9 | -77.488 | 0.910 |
| | Lymphoid | 24 | 92.8 | >40.00000 | 7.2 | -18.660 | 0.055 |
| | | 48 | 59.7 | 0.125 | 40.5 | -1.834 | 0.863 |
| | | 96 | 54.1 | 0.037 | 46.0 | -1.549 | 0.849 |
| PM_CG1_010 | Leukemic | 24 | 7.3 | 0.016 | 92.7 | -2.446 | 0.960 |
| | | 48 | 2.2 | 0.010 | 97.8 | -2.554 | 0.995 |
| | | 96 | 0.0 | 0.006 | 100.0 | -2.090 | 0.924 |
| | Lymphoid | 24 | 35.7 | 0.060 | 64.7 | -1.255 | 0.933 |
| | | 48 | 24.2 | 0.043 | 76.0 | -1.509 | 0.988 |
| | | 96 | 18.2 | 0.046 | 82.0 | -1.619 | 0.900 |
| PM_CG1_013 | Leukemic | 24 | 72.7 | 0.236 | 28.1 | -1.018 | 0.654 |
| | | 48 | 43.7 | 0.010 | 56.3 | -2.127 | 0.903 |

TABLE 12-continued

| Donor ID | Cell Line (LIVE) | Incubation Time (hours) | Activity Area | $EC_{50}$ | $E_{max}$ | Curve Slope | $r^2$ |
|---|---|---|---|---|---|---|---|
| | Lymphoid | 24 | 53.8 | 0.142 | 47.9 | −0.809 | 0.821 |
| | | 48 | 31.0 | 0.046 | 69.4 | −1.108 | 0.972 |
| | | 96 | 29.3 | 0.024 | 70.9 | −1.266 | 0.981 |
| PM_CG3_001 | Leukemic | 24 | 49.8 | 0.162 | 64.3 | −2.142 | 0.835 |
| | | 48 | 9.9 | 0.028 | 96.1 | −1.456 | 0.920 |
| | | 96 | 2.1 | 0.010 | 98.8 | −24.306 | 0.855 |
| | Lymphoid | 24 | 74.7 | >1.00000 | 25.9 | −8.855 | 0.745 |
| | | 48 | 50.3 | 0.005 | 50.1 | −1.974 | 0.878 |
| | | 96 | 9.6 | 0.006 | 91.5 | −1.610 | 0.950 |
| PM_CG3_002 | Leukemic | 24 | 37.3 | 0.140 | 86.7 | −1.117 | 0.982 |
| | | 48 | 15.6 | 0.047 | 95.3 | −1.255 | 0.954 |
| | | 96 | 14.8 | 0.034 | 89.7 | −1.961 | 0.916 |
| | Lymphoid | 24 | 59.5 | 0.069 | 47.5 | −1.304 | 0.974 |
| | | 48 | 37.3 | 0.055 | 69.4 | −1.668 | 0.979 |
| | | 96 | 13.1 | 0.019 | 94.5 | −0.961 | 0.983 |
| PM_CG3_003 | Leukemic | 24 | 17.3 | 0.010 | 83.9 | −2.358 | 0.987 |
| | | 48 | 6.7 | 0.006 | 94.2 | −1.961 | 0.892 |
| | | 96 | 1.5 | 0.003 | 98.9 | −3.149 | 0.970 |
| | Lymphoid | 24 | 31.4 | 0.007 | 69.5 | −1.630 | 0.871 |
| | | 48 | 48.5 | 0.054 | 58.6 | −1.294 | 0.954 |
| | | 96 | 44.3 | 0.043 | 58.6 | −2.915 | 0.940 |
| PM_CG3_004 | Leukemic | 24 | 31.5 | 0.074 | 78.2 | −1.727 | 0.950 |
| | | 48 | 32.9 | 0.024 | 68.7 | −12.529 | 0.886 |
| | | 96 | 7.4 | 0.004 | 93.0 | −3.768 | 0.990 |
| | Lymphoid | 24 | 76.4 | 0.514 | 52.5 | −0.815 | 0.278 |
| | | 48 | 89.9 | >1.00000 | 10.1 | −10.634 | 0.096 |
| | | 96 | 50.6 | 0.085 | 56.5 | −2.000 | 0.889 |
| PM_CG3_005 | Leukemic | 24 | 97.5 | >1.00000 | 2.5 | −10.354 | 0.095 |
| | | 48 | 77.6 | >1.00000 | 24.4 | −3.125 | 0.837 |
| | | 96 | 35.5 | 0.158 | 98.3 | −0.804 | 0.923 |
| | Lymphoid | 24 | 98.4 | >1.00000 | 14.4 | −0.789 | 0.008 |
| | | 48 | 63.3 | 0.043 | 38.7 | −3.025 | 0.963 |
| | | 96 | 41.8 | 0.079 | 69.5 | −1.324 | 0.873 |
| PM_CG3_006 | Leukemic | 24 | 20.7 | 0.038 | 83.1 | −2.907 | 0.961 |
| | | 48 | 8.9 | 0.013 | 92.4 | −3.571 | 0.982 |
| | | 96 | 0.0 | 0.009 | 100.0 | −2.476 | 0.900 |
| | Lymphoid | 24 | 56.6 | 0.058 | 46.1 | −11.538 | 0.877 |
| | | 48 | 39.0 | 0.026 | 63.4 | −2.100 | 0.935 |
| PM_CG3_007 | Leukemic | 24 | 21.5 | 0.054 | 83.4 | −3.334 | 0.817 |
| | | 48 | 11.5 | 0.016 | 89.9 | −5.729 | 0.913 |
| | | 96 | 1.4 | 0.010 | 99.6 | −17.270 | 0.947 |
| PM_CG3_008 | Leukemic | 24 | 62.7 | 0.003 | 37.5 | −3.305 | 0.626 |
| | | 48 | 35.0 | 0.002 | 65.2 | −15.864 | 0.671 |
| | | 96 | 6.6 | 0.002 | 93.6 | −11.949 | 0.954 |
| PM_CG3_009 | Leukemic | 24 | 44.1 | 0.012 | 60.8 | −0.788 | 0.615 |
| | | 48 | 20.5 | 0.008 | 80.3 | −2.763 | 0.895 |
| | | 96 | 2.5 | 0.005 | 98.0 | −3.071 | 0.887 |
| | Lymphoid | 24 | 60.4 | NC | 39.9 | −0.675 | 0.404 |
| | | 48 | 33.2 | 0.028 | 69.4 | −2.430 | 0.848 |
| | | 96 | 27.9 | 0.011 | 98.1 | −0.071 | 0.735 |
| PM_CG3_010 | Leukemic | 24 | 19.6 | 0.019 | 83.1 | −1.760 | 0.723 |
| | | 48 | 2.0 | 0.010 | 99.2 | −3.798 | 0.958 |
| | | 96 | 0.8 | 0.005 | 99.7 | −4.131 | 0.943 |
| | Lymphoid | 96 | 36.7 | 0.041 | 67.9 | −1.725 | 0.784 |
| PM_CG3_011 | Leukemic | 24 | 22.4 | 0.020 | 79.4 | −2.601 | 0.763 |
| | | 48 | 16.5 | 0.006 | 84.0 | −6.595 | 0.914 |
| | | 96 | 0.4 | 0.003 | 100.0 | −2.354 | 0.978 |
| PM_CG3_012 | Leukemic | 24 | 20.0 | 0.006 | 80.6 | −2.043 | 0.942 |
| | | 48 | 3.8 | 0.004 | 96.5 | −14.201 | 0.953 |
| | | 96 | 0.6 | 0.003 | 99.8 | −5.893 | 0.972 |
| PM_CG3_013 | Leukemic | 24 | 24.3 | 0.029 | 88.2 | −0.496 | 0.844 |
| | | 48 | 31.8 | 0.013 | 69.3 | −3.620 | 0.902 |
| | | 96 | 5.7 | 0.005 | 95.2 | −1.717 | 0.894 |
| | Lymphoid | 24 | 85.6 | 0.001 | 14.5 | −3.108 | 0.798 |
| PM_CG3_014 | Leukemic | 24 | 59.1 | 0.083 | 46.9 | −1.518 | 0.487 |
| | | 48 | 50.4 | NC | 67.7 | −0.343 | 0.806 |
| PM_CG3_015 | Leukemic | 24 | 42.1 | 0.017 | 59.2 | −2.563 | 0.940 |
| | | 48 | 19.2 | 0.010 | 81.8 | −3.262 | 0.988 |
| | | 96 | 4.9 | 0.003 | 95.5 | −3.611 | 0.985 |
| | Lymphoid | 24 | 48.4 | 0.009 | 55.0 | −0.820 | 0.873 |
| | | 48 | 62.5 | 0.025 | 38.5 | −58.188 | 0.753 |
| | | 96 | 43.4 | 0.042 | 72.9 | −0.608 | 0.859 |
| PM_CG3_016 | Leukemic | 24 | 41.5 | 0.114 | 71.4 | −1.739 | 0.713 |
| | | 48 | 19.4 | 0.037 | 91.2 | −0.975 | 0.805 |
| | Lymphoid | 24 | 48.5 | 0.039 | 54.1 | −2.748 | 0.930 |

TABLE 12-continued

| Donor ID | Cell Line (LIVE) | Incubation Time (hours) | Activity Area | $EC_{50}$ | $E_{max}$ | Curve Slope | $r^2$ |
|---|---|---|---|---|---|---|---|
| PM_CG3_017 | Leukemic | 24 | 36.0 | 0.004 | 64.3 | −2.073 | 0.596 |
| | | 48 | 7.0 | 0.004 | 93.4 | −8.659 | 0.851 |
| | | 96 | 1.0 | 0.004 | 99.4 | −19.697 | 0.784 |
| | Lymphoid | 24 | 63.7 | 0.017 | 36.9 | −5.102 | 0.595 |
| | | 48 | 32.8 | 0.025 | 94.7 | −0.334 | 0.741 |
| | | 96 | 24.4 | 0.015 | 81.4 | −0.910 | 0.702 |
| PM_CG3_018 | Leukemic | 24 | 2.6 | 0.007 | 98.1 | −4.420 | 0.989 |
| | | 48 | 0.7 | 0.004 | 99.7 | −28.795 | 0.968 |
| | | 96 | 0.6 | 0.002 | 99.6 | −5.245 | 0.947 |
| PM_CG3_019 | Leukemic | 24 | 5.3 | 0.010 | 95.7 | −58.957 | 0.926 |
| | | 48 | 1.3 | 0.008 | 99.6 | −3.825 | 0.934 |
| | | 96 | 1.1 | 0.004 | 99.3 | −19.174 | 0.901 |
| PM_CG3_020 | Leukemic | 24 | 13.4 | 0.006 | 87.3 | −2.826 | 0.975 |
| | | 48 | 3.3 | 0.003 | 97.1 | −4.320 | 0.965 |
| | | 96 | 1.5 | 0.003 | 98.7 | −7.081 | 0.932 |

A comparative analysis of activity areas from tumor versus normal lymphoid cells in acute myeloid leukemia bone marrow samples is provided in FIG. 31. In the figure, the Activity Area value integrates potency ($EC_{50}$) and efficacy ($E_{max}$): the smaller the Activity Area, the more potent and effective the treatment is. A paired two-tailed Student's t-test was used to determine the statistical significance of the difference between the AUC of tumor compared to lymphoid cells. Error bars represent standard deviation.

Conclusion. Compound 1 was tested in a panel of samples obtained from 30 AML patients. Bone marrow (BM) aspirates obtained during patient diagnosis were plated without separation of constituent cells and tested for sensitivity at 24, 48, and 96 hours according to a published procedure (Bennett, et al *Clin Lymphoma Myeloma Leuk* 2014 August; 14(4):305-318). For standard of care agents, this test has been shown to correlate very well with clinical sensitivity. The ex vivo efficacy of Compound 1 was time- and concentration-dependent, showing potent activity in 26 out of 30 patient samples tested with an average concentration required to induce 50% of the maximal response ($EC_{50}$) of 21 nM (range was 2 to 160 nM) across all three time points. Three out of four patient samples categorized as insensitive displayed higher $EC_{50}$ values than sensitive samples, and all four consistently showed poorer efficacy as measured by an inability to deplete leukemic blasts by more than 68% at 24 and 48 hours. In the sensitive patient samples, leukemic cell killing was rapid and very efficient in that, by 24 hours, on average greater than 82% were depleted; by 48 hours, >92% were depleted and by 96 hours, >98% of the leukemic cells were depleted. In patient samples where sufficient normal lymphocytes could be counted, Compound 1 was significantly less active, with only modest efficacy against the normal cells ($E_{max}$ [maximum possible effect] averaged 46% to 76% from 24 to 96 hours) and displayed a differential potency between leukemic and normal cells of 2- to 5-fold.

Example 5

In Vitro Evaluation of Effect of Compound 1 on Hematopoietic Progenitors

Experimental Design: human bone marrow (BM) CD34+ cells were used to evaluate the potential for BM toxicity induced by Compound 1. In order to test the effects of Compound 1 on the functionality of hematopoietic progenitors, colony forming assays were done by seeding BM CD34+ cells on MethoCult medium. Cells were seeded directly in MethoCult with Compound 1 or cultured in liquid medium with Compound 1 for 2, 4, or 8 hours and then seeded in compound-free MethoCult to evaluate the effect of different exposure times. Early apoptosis induced by Compound 1 on HSC was analyzed by flow cytometry.

Results. Colony forming units (CFU) of common granulocyte/erythrocyte/monocyte/megakaryocyte (CFU-GEMM), CFU of granulocyte/monocyte (CFU-GM), burst forming unit of erythrocytes (BFU-E), and CFU of erythrocytes (CFU-E) in cultures exposed to Compound 1 or DMSO were scored on STEMvision. Absolute numbers from each condition for each of four normal BM donors are shown in Tables 13-16.

TABLE 13

Effect of Compound 1 on Granulocytic, Monocytic and/or Erythroid Progenitors in Colony Forming Assays from Donor HD10

| | Colony Number | | | | | | | | | | |
|---|---|---|---|---|---|---|---|---|---|---|---|
| | DMSO | 7.4 nM Compound 1 | | 22.2 nM Compound 1 | | 67 nM Compound 1 | | 200 nM Compound 1 | | 600 nM Compound 1 | |
| CFU-GEMM | 2 | 4 | 4 | 2 | 2 | 0 | 5 | 1 | 0 | 0 | 0 | 0 |
| CFU-GM | 81 | 77 | 82 | 74 | 71 | 80 | 48 | 61 | 0 | 2 | 0 | 0 |
| BFU-E | 33 | 35 | 40 | 36 | 24 | 24 | 26 | 20 | 5 | 1 | 2 | 0 |
| CFU-E | 0 | 0 | 2 | 2 | 0 | 0 | 0 | 0 | 3 | 1 | 0 | 0 |

TABLE 14

Effect of Compound 1 on Granulocytic, Monocytic and/or Erythroid Progenitors in Colony Forming Assays from Donor HD14

| | Colony Number | | | | | | | | | | |
|---|---|---|---|---|---|---|---|---|---|---|---|
| | DMSO | 7.4 nM Compound 1 | | 22.2 nM Compound 1 | | 67 nM Compound 1 | | 200 nM Compound 1 | | 600 nM Compound 1 | |
| CFU-GEMM | 0 | 0 | 0 | 0 | 0 | 0 | 0 | 0 | 0 | 0 | 0 | 0 |
| CFU-GM | 20 | 10 | 15 | 12 | 16 | 15 | 6 | 4 | 0 | 0 | 0 | 0 |
| BFU-E | 22 | 9 | 23 | 18 | 14 | 18 | 3 | 6 | 3 | 1 | 0 | 2 |
| CFU-E | 3 | 0 | 6 | 0 | 7 | 0 | 4 | 4 | 2 | 1 | 2 | 0 |

TABLE 15

Effect of Compound 1 on Granulocytic, Monocytic and/or Erythroid Progenitors in Colony Forming Assays from Donor HD18

| | Colony Number | | | | | | | | | | |
|---|---|---|---|---|---|---|---|---|---|---|---|
| | DMSO | | 7.4 nM Compound 1 | | 22.2 nM Compound 1 | | 67 nM Compound 1 | | 200 nM Compound 1 | | 600 nM Compound 1 |
| CFU-GEMM | 4 | 2 | 2 | 4 | 1 | 1 | 0 | 0 | 0 | 0 | 0 | 0 |
| CFU-GM | 57 | 57 | 59 | 73 | 55 | 62 | 2 | 6 | 0 | 0 | 0 | 0 |
| BFU-E | 34 | 27 | 22 | 31 | 12 | 13 | 8 | 6 | 1 | 1 | 0 | 2 |
| CFU-E | 6 | 5 | 0 | 2 | 7 | 1 | 3 | 0 | 2 | 3 | 1 | 1 |

TABLE 16

Effect of Compound 1 on Granulocytic, Monocytic and/or Erythroid Progenitors in Colony Forming Assays from Donor HD19

| | Colony Number | | | | | | | | | | |
|---|---|---|---|---|---|---|---|---|---|---|---|
| | DMSO | | 7.4 nM Compound 1 | | 22.2 nM Compound 1 | | 67 nM Compound 1 | | 200 nM Compound 1 | | 600 nM Compound 1 |
| CFU-GEMM | 4 | 2 | 4 | 4 | 0 | 1 | 0 | 1 | 0 | 0 | 0 | 0 |
| CFU-GM | 47 | 46 | 44 | 70 | 34 | 35 | 4 | 5 | 0 | 0 | 0 | 0 |
| BFU-E | 40 | 35 | 34 | 42 | 50 | 38 | 4 | 9 | 1 | 3 | 6 | 0 |
| CFU-E | 2 | 4 | 9 | 4 | 4 | 5 | 6 | 3 | 1 | 3 | 1 | 1 |

As expected, CFU-GEMM and CFU-E colony numbers were very low and only the percentage of CFU-GM and BFU-E was used for IC$_{50}$ calculations (FIG. 32). The IC$_{50}$ values for inhibition of CFU-GM were comparable in magnitude among donors. The IC$_{50}$ values for inhibition of BFU-E were comparable in magnitude among the donors, with the exception of the IC$_{50}$ for BFU-E from donor D19, which was a considerably lower value than for the other three donors.

Bone marrow CD34+ cells from normal donors were incubated with Compound 1 in MethoCult medium. Colony numbers for CFU-GM and BFU-E progenitors were counted using STEMVision automatic colony counting instrument and software and normalized to the colony number of the DMSO control. Results plotted as percentage of DMSO control vs concentration of Compound 1 were used to determine IC$_{50}$ values. Data are shown as mean±standard error of the mean of n=3 technical replicates. Donors were HD10, HD14, HD18, and HD19.

Early apoptosis after 2, 4, and 8 hours of Compound 1 exposure was measured by flow cytometry. Signs of Compound 1-induced apoptosis at these early time points, as measured by the percentage of Annexin V negative cells, were not evident at concentrations of Compound 1 up to 600 nM. Similar trends were observed in HSC (CD34+/CD38−) and HPC (CD34+/CD38+) (Tables 17-20). The potential effects of longer term exposure on HSC and HPC populations were not evaluated in this study.

TABLE 17

Percentage of Viable CD34 Positive/CD38 Negative Cells from Donor HD8

| Concentration of Compound 1 (nM) | Percentage of Viable CD34 Positive/CD38 Negative Cells (Donor 8) Exposure Time | | |
|---|---|---|---|
| | 2 Hours | 4 Hours | 8 Hours |
| 0 | 92.23 | 89.75 | 80.65 |
| 7.4 | 90.76 | 86.62 | 78.24 |
| 22.2 | 91.58 | 85.25 | 77.27 |
| 67 | 89.08 | 86.7 | 74.9 |
| 200 | 87.54 | 87.28 | 75.25 |
| 600 | 88.53 | 87.28 | 76.52 |

TABLE 18

Percentage of Viable CD34 Positive/CD38 Positive Cells from Donor HD8

| Concentration of Compound 1 (nM) | Percentage of Viable CD34 Positive/CD38 Positive Cells (Donor 8) Exposure Time | | |
|---|---|---|---|
| | 2 Hours | 4 Hours | 8 Hours |
| 0 | 94.74 | 96.82 | 88.39 |
| 7.4 | 93.97 | 95.2 | 86.63 |
| 22.2 | 94.59 | 90.58 | 87.98 |
| 67 | 91.28 | 92.96 | 84.53 |
| 200 | 89.66 | 92.97 | 86.63 |
| 600 | 89.83 | 91.4 | 84.28 |

TABLE 19

Percentage of Viable CD34 Positive/CD38 Negative Cells from Donor HD9

| Concentration of Compound 1 (nM) | Percentage of Viable CD34 Positive/CD38 Negative Cells (Donor 9) Exposure Time | | |
|---|---|---|---|
| | 2 Hours | 4 Hours | 8 Hours |
| 0 | 88.68 | 87.31 | 83.93 |
| 7.4 | 90.39 | 88.17 | 77.71 |
| 22.2 | 89.97 | 88.84 | 75.31 |
| 67 | 89.34 | 88.3 | 71.7 |
| 200 | 88.75 | 89.04 | 70.69 |
| 600 | 88.83 | 88.33 | 70.81 |

TABLE 20

Percentage of Viable CD34 Positive/CD38 Positive Cells from Donor HD9

| Concentration of Compound 1 (nM) | Percentage of Viable CD34 Positive/CD38 Positive Cells (Donor 9) Exposure Time | | |
|---|---|---|---|
| | 2 Hours | 4 Hours | 8 Hours |
| 0 | 92.48 | 92.38 | 92.4 |
| 7.4 | 92 | 92.52 | 87.38 |
| 22.2 | 90.41 | 94.48 | 87.5 |
| 67 | 90.17 | 93.34 | 83.86 |
| 200 | 89.24 | 93.44 | 84.26 |
| 600 | 88.98 | 91.69 | 82.42 |

Even though early apoptosis was not detected at the 2-, 4-, or 8-hour time points, colony forming assays of the same cells showed impairment of BFU-E and CFU-GM growth after 8 hours of exposure to Compound 1. At concentrations higher than 80 nM, the number of colonies was reduced by more than 50%. Nevertheless, the effects were lower than those observed when Compound 1 was maintained in the MethoCult medium throughout the 14-day incubation period without compound washout (Continuous condition).

The effect of Compound 1 on hematopoietic progenitors was explored further using samples from donors HD46, HD47, HD48, and HD50. The number of BFU-E colonies was reduced by more than 50% at concentrations of Compound 1≥111 nM with 8 hours exposure (p<0.01 and 0.001), with individual IC50 values ranging from 30 to 150 nM. The reduction in the number of CFU GM colonies formed with 8 hours exposure to 1000 nM Compound 1 ranged from 31% to 46% for the four donors (p<0.01) and ranged from 22% to 46% at 333 nM Compound 1 (p<0.05) (FIGS. 33A-C). Results shown are the mean values for the four donors; error bars represent standard error of the (SEM).

FIGS. 33A and 33B provide, colony numbers after pre-incubation of bone marrow CD34+ cells with Compound 1 for 4 or 8 hours, respectively, in Iscove's medium, followed by incubation in MethoCult medium without Compound 1 for 14 days. FIG. 33C provides colony numbers after incubation of bone marrow CD34+ cells in MethoCult medium in continuous presence of Compound 1 for 14 days. The number of myeloid and erythroid colonies was appreciably diminished at concentrations ≥111 nM in the samples exposed to Compound 1 for the entire 14-day incubation period.

Conclusions.

The goal of induction therapy in AML is to achieve complete remission (CR). A CR is defined as neutrophils greater than 1×10$^9$ cells/L in the peripheral blood, less than 5% bone marrow blasts, and no evidence of extramedullary disease. Chemotherapy is given to "empty" the bone marrow of all hematopoietic cells (both benign and malignant) and to allow the surviving hematopoietic stem cells (HSCs) to repopulate the marrow with normal cells, thereby yielding remission.

Evaluation of Compound 1 toxicity in hematopoietic progenitors was conducted using standardized colony forming assays in CD34+ cells from four healthy donors. Inhibition of granulo-monocytic and erythroid progenitors was observed with IC$_{50}$ values of 82 nM to 135 nM and 32 nM to 131 nM, respectively.

Using cells from four different donors, the response of different exposure times to Compound 1 was also analyzed. The toxicity of Compound 1 was attenuated when the length of time of exposure to this compound was reduced. At 8 hours, the effect was reduced in intensity but, at 4 hours, the effect was absent. Toxicity was greatest after continuous single dose exposure. Signs of apoptosis, as measured by Annexin V flow cytometry, were not evident at 2, 4, or 8 hours at the concentrations of Compound 1 tested (up to 600 nM) in either CD34+/CD38− hematopoietic stem cells (HSC) or CD34+/CD38+ hematopoietic progenitors (HPC). These data suggest that Compound 1 toxicity to hematopoietic progenitors could be effectively managed when dose and time of exposure are reduced.

Example 6

Effect of Compound 1 on Neutrophil Maturation—Healthy Bone Marrow Progenitors Ex Vivo Compound 1 effects on the proliferation of CFU-GM progenitor cells are of special relevance because of the role of these progenitor cells in drug-induced neutropenia. Neutrophils are derived from CFU-GM progenitors occurring through distinct stages, from progenitor cells through myeloblasts (stage I), promyelocytes (stage II) and myelocytes (stage III) that finally mature towards neutrophils with banded or segmented nuclei. The effects of Compound 1 on neutrophil maturation were determined by using two-dimensional cultivation of progenitors followed by flow cytometry. Bone marrow CD34+ cells obtained from healthy volunteers were transferred to tissue culture medium and myeloid differentiation was induced ex vivo by adding stem cell factor (SCF), Fms-related tyrosine kinase 3 ligand (Flt-3 ligand), and granulocyte colony stimulating factor (G-CSF). Concentrations of Compound 1 up to 30 nM and exposure times of 8, 24, and 72 hours starting at Day 0 were selected to evaluate the effect of Compound 1 in this system. After exposure to Compound 1, cells were washed and then incubated in culture medium in the absence of Compound 1 until Day 14. Cell differentiation and apoptosis were measured in a flow cytometry-based method at Days 3, 7, 10, and 14 of culture, with apoptotic and dead cells identified as Annexin V positive and 7-aminoactinomycin D positive. Results showed that viability was decreased only at the highest Compound 1 concentration (30 nM) tested when cells were exposed to the compound for 24 hours and 72 hours (FIG. 34).

In FIG. 34, Bone marrow C34+ cells from healthy donors were incubated with 30 nM Compound 1 or DMSO. Compound 1 was washed out after 8, 24 or 72 hours, the medium was replaced, and the cultures were incubated until Day 14 in the absence of Compound 1 or DMSO. Cells were classified from most immature to most mature as HPC, Stage I, Stage II, Stage III and Stage IV according to their expression of CD34, CD33 and CD11b. Then apoptotic cells from each stage were identified as positive for Annexin V and labeled as AV+HPC, AV+Stage I, AV+Stage II, AV+Stage II and AV+Stage IV. N=1 for each Compound 1 exposure period (8 hours, 24 hours and 72 hours). Representative results are shown for bone marrow progenitors from one of two healthy donors evaluated. There was no reduction in viability at concentrations of ≤3 nM Compound 1 in the 24-hour and 72-hour exposure groups or with any concentration of Compound 1 from 0.03 to 30 nM with the exposure time of 8 hours. After removal of Compound 1, cell viability in the cultures was increased, reaching control values at Day 10 in cultures exposed to Compound 1 for 24 hours. Cell viability increased from 9.6% to 30% (Donor 1) and from 13% to 44% (Donor 2) in cultures exposed to Compound 1 for 72 hours. Apoptosis at 30 nM Compound 1 after 24 or 72 hours of exposure affected all stages of myeloid differentiation but surviving cells were able to proliferate and fully mature to normal neutrophils (FIG. 34).

Summary of Hematopoiesis Studies: In summary, these data indicate that addition of Compound 1 to ex vivo cultures of healthy donor bone marrows resulted in decreased/delayed formation of granulo-monocytic and erythroid colonies by inducing cell growth delay or arrest. The inhibitory growth inflicted on progenitors was greatly reduced when Compound 1 was washed out after up to 8 hours treatment, suggesting that dose-schedule strategies for Compound 1 treatment should allow the survival of hematopoietic stem cells and progenitors, reducing the potential of hematotoxicity in vivo. The effect of Compound 1 on progenitor differentiation was further investigated by analyzing progenitor populations during neutrophil development. Longer treatments (up to 72 hours) with Compound 1 affected all stages of neutrophil differentiation by inducing apoptosis in a portion of the cells; however, the surviving cells were able to proliferate and fully mature to normal neutrophils. These findings suggest the possibility that dosing strategies can be devised for Compound 1, a compound that induces strong apoptosis in AML cell lines and AML patient blasts, that eliminate tumor cells but may spare a portion of the normal hematopoietic stem/progenitor cells and allow reversal of neutropenia.

Example 7

Effect of Compound 1 on In Vitro Viability of MDS Samples

Methods. The effect of Compound 1 on high risk MDS samples was measured in an in vitro liquid culture as well as by colony assays in order to better define its effect on stem/progenitor cells. Bone marrow mononuclear cells (BMMCs) from high risk MDS patients were cultured in vitro in CellGro medium (GellGenix) supplemented with hLDL (40 µg/mL), SCF (50 ng/mL), FLT3L (50 ng/mL), IL-3 (10 ng/mL), IL-6 (25 ng/mL) and TPO (100 ng/mL), all from Peprotech. During culture, cells were exposed to different concentrations of Compound 1 (37, 111, 333 and 1000 nM) or DMSO control. After 24 hours, cells were washed twice to remove compound and maintained in culture up to one week, performing viable cell counting on days 1, 3 and 7. Just after compound washout, 105 cells per condition were collected for colony forming assays and another 105 cells were stained for intracellular flow cytometry.

For colony forming assays cells were seeded in Methocult media (Stem Cell Technologies), incubated at 37° C. during 14 days and scored by automatic counting using StemVision (Stem Cell Technologies).

For intracellular flow cytometry measurement of apoptosis cells were fixed in 1.6% paraformaldehyde, permeabilized in ice cold methanol and stained using a FITC-conjugated anti-active Caspase 3 antibody (Becton Dickinson). A FACSCanto II flow cytometer (Becton Dickinson) was used for flow cytometry data acquisition. Flow cytometry standard (FCS) files were analyzed using Infinicyt software (Cytognos).

Results. As shown in FIG. 35A, the number of viable cells was significantly reduced after 24 hours exposure to concentrations of Compound 1 in a dose dependent manner and this effect was maintained during at least a week. As confirmed by caspase 3 activation, this effect on MDS cells was mediated by induction of apoptosis (FIG. 35B). Compound 1 effects were more acute in MDS progenitor cells measured by colony forming assays (FIG. 35C).

Conclusion. Compound 1 induced a decrease in cell number in MDS samples. This effect was mediated by activation of caspase 3. Compound 1 was also effective decreasing MDS progenitors. This data shows the antiproliferative and apoptotic effect of Compound 1 on MDS samples.

Example 8

Effect of Compound 1 on Cell Survival and Self-Renewal of MDS Patient Samples

Methods. Mouse stromal cells SL/M2 stably expressing human interleukin-3 (IL-3), granulocyte colony stimulating factor (G-CSF) and stem cell factor (SCF) were cultured to confluency, followed by gamma-irradiation. Human CD34+ bone marrow cells isolated from 3 high-risk MDS patients (HR-MDS), 3 secondary AML patients arising from MDS (sAML) and 5 age-matched healthy donors were then cultured with inactivated SL/M2 cells for a week. Next, human progenitor cells were quantified by FACS and cells were plated in methylcellulose for colony forming assay (cell survival assay). After two weeks, 20-25 colonies were picked from each condition, resuspended and replated in fresh methylcellulose for $2^{nd}$ round of colony forming assay (cell self-renewal assay).

Results. In the colony formation assay (FIG. 36A), Compound 1 induced significant cytotoxicity in HR-MDS, sAML and normal bone marrow progenitors. Compound 1 at 10 nM and 100 nM tended to inhibit more specifically the cell survival of HR-MDS and AML progenitors compared to normal bone marrow progenitors. In the colony replating assay (FIG. 36B), Compound 1 at 1 nM and 10 nM significantly reduced the self-renewal of sAML and HR-MDS progenitors more than that of normal bone marrow progenitors.

Conclusion. Compound 1 inhibited the growth of sAML and HR-MDS cells. A therapeutic window was shown, with the reduced effect on normal bone marrow progenitors Example 9

Antitumor Activity of Compound 1 in Acute Myeloid Leukemia Xenograft Mouse Model In this study, Compound 1 antitumor activity in the HL-60 IV AML xenograft model was studies. In this model, HL-60 human AML cells engraft in host BM and internal organs (eg, spleen, liver) and animals develop progressive peripheral leukocytosis. Female severe combined immunodeficiency (SCID) mice were inoculated with HL-60 cells by tail vein injection. To understand the effect of Compound 1 on the xenografted HL-60 cells, animals were dosed intraperitoneal (IP) with vehicle or Compound 1 (0.5, 1, 2.5, and 5 mg/kg) once daily (QD)×5 between Weeks 3 and 4 post-engraftment (AP6516, survival study) or animals were dosed IP twice daily (BID) with vehicle or Compound 1 for 5 or 10 consecutive days (5 mg/kg BIDx5 or 2.5 mg/kg, BIDx10) between Weeks 6 and 8 post-engraftment (Study AP6982, % human CD33+ [hCD33+] cells in BM).

Survival Study

Tumor burden from the peripheral blood of HL-60-bearing animals was assessed by fluorescence-activated cell sorting (FACS) at Week 7 post-tumor cell inoculation. No effect on tumor burden was observed with any of the Compound 1 treatment groups when compared to the vehicle control group. Mice from the vehicle control and Compound 1 treatment groups succumbed to disease burden starting on Day 54 for the vehicle control group and between Day 51 and Day 57 for the Compound 1 treatment groups. No overall survival benefit was observed for Compound 1-treated groups. One mouse (1/8) from the 2.5 mg/kg Compound 1-treated group survived to study termination on Day 162. The positive control fludarabine significantly prolonged survival (median survival 76 days versus the vehicle control group's 67.5 days; p<0.05).

HL-60 Tumor Cells in Bone Marrow

Since no activity was observed with Compound 1 treatment in the HL-60 survival study following 5 consecutive days of treatment at Week 3, experiments were designed to look at endpoints closer to the time of treatment. In this study, different Compound 1 dosing schedules (5 mg/kg, BIDx5 consecutive days versus 2.5 mg/kg, BIDx10 consecutive days) were studied while maintaining the total amount of drug administered constant. Vehicle control animals were treated with 5% N-methyl-2-pyrrolidone (NMP)/45% PEG 400/50% saline. Treatment was initiated 6 weeks post inoculation. Vehicle and Compound 1 treatment groups were terminated either on Day 7 (following 5 consecutive days of 5 mg/kg twice a day [BID] Compound 1) or on Day 11 (following 10 consecutive days of 2.5 mg/kg BID Compound 1) post treatment initiation. The primary endpoint for the study was percentage of hCD33+/CD45+ cells in the BM by FACS analysis. Additional endpoints included cell viability, body weight, and BM histology.

HL-60 cells were identified from femur bone marrow samples by FACS analysis as CD33+/CD45+ with human specific antibodies. The percentage of human CD33+/CD45+ cells in the BM of vehicle-treated animals from the BIDx5 and BIDx10 groups were 47.5±6% and 55.2±6%, respectively. Treatment with 5 mg/kg Compound 1 BIDx5 resulted in a significant 54.0% reduction (p=0.0013) in percentage of human CD33+/CD45+ tumor cells in the BM when compared to the vehicle control group (47.5% versus 21.9% human CD33+/CD45+ cells for the vehicle control and Compound 1 treatment groups, respectively). Treatment with 2.5 mg/kg Compound 1 BIDx10 resulted in a significant 71.5% reduction (p<0.0001) in percentage of human CD33+/CD45+ tumor cells in the BM when compared to the vehicle control group (55.2% versus 15.7% human CD33+/CD45+ cells for the vehicle control and Compound 1 treatment groups, respectively). No significant effect on bone marrow cell viability, as determined by FACS analysis, was observed with Compound 1 treatment but it should be noted that this measurement does not distinguish between mouse and human bone marrow cells. Body weight loss consistent with disease progression was observed in both the vehicle and compound treatment groups; there was no difference noted with Compound 1 treatment.

The alternate femur of vehicle and Compound 1-treated animals was fixed in formalin, embedded in paraffin and processed for hematoxylin and eosin staining. A single tissue section/animal was used for histological analysis and the percent of tumor in viable bone marrow was estimated based on the area occupied by tumor cells. There was a significant 35% reduction (p<0.006 relative to the vehicle control) in the percentage of viable tumor in the bone marrow with Compound 1 (5 mg/kg) BIDx5 treatment. Treatment with 2.5 mg/kg Compound 1 BIDx10 demonstrated a trend towards a decrease in the percentage of viable tumor in the bone marrow (23.5% reduction relative to the vehicle control) but this decrease was not statistically significant. These data are consistent with the reductions observed in the FACS data following Compound 1 treatment; however, the magnitude of the change is less with the histological analysis. This could be due to the small sample area in the histological assessment (one section/mouse) compared to analysis of the entire bone marrow cell population by FACS.

Example 10

A Phase 1, Open-Label, Dose-Finding Study of Compound 1, a Novel Cereblon E3 Ligase Modulating Drug in Subjects With Relapsed or Refractory Acute Myeloid Leukemia Indication: Treatment of relapsed or refractory acute myeloid leukemia (AML).

Objectives
Primary Objectives:
To determine the safety and tolerability of Compound 1.
To define the non-tolerated dose (NTD), the maximum tolerated dose (MTD) and/or the recommended Phase 2 dose (RP2D) of Compound 1.
Secondary Objectives:
To provide information on the preliminary efficacy of Compound 1.
To characterize the pharmacokinetics (PK) of Compound 1.
Study Design
This is an open-label, Phase 1, dose escalation and expansion, first in human clinical study of Compound 1 in subjects with relapsed or refractory AML. The dose escalation part (Part A) of the study will evaluate the safety and tolerability of escalating doses of Compound 1, administered intravenously, and determine the MTD of Compound 1. The expansion part (Part B) will further evaluate the safety and efficacy of Compound 1 administered at or below the MTD in selected expansion cohorts of up to approximately 20 evaluable subjects each in order to determine the RP2D. One or more dosing regimens and/or disease subsets may be selected for cohort expansion. Parts A and B will consist of 3 periods: Screening, Treatment, and Follow-up. Leukemia response will be determined by the Investigator. Disease assessment will be based on the International Working Group Response Criteria in AML (Cheson et al. Revised recommendations of the International Working Group for diagnosis, standardization of response criteria, treatment outcomes, and reporting standards for therapeutic trials in acute myeloid leukemia. *J Clin Oncol* 2003; 21(24):4642-9).
Screening Period
The Screening Period starts 28 days prior to first dose of Compound 1. The informed consent document must be signed and dated by the subject and the administering staff prior to the start of any other study procedures. All screening tests and procedures must be completed within the 28 days prior to the first dose of Compound 1.
Treatment Period
In the Treatment Period, Compound 1 will be administered intravenously on Days 1-5 of each 28 day cycle for up to 4 cycles in the absence of disease progression, relapse, unacceptable toxicity, or subject/physician decision to withdraw. During Part A, 2 additional cycles of treatment beyond Cycle 4 may be allowed if the subject is demonstrating clinical benefit (stable disease or PR) and tolerating the study drug without unacceptable toxicity. Modified dosing schedules (eg, increasing from 5 days to up to 10 days of dosing) may be evaluated in additional cohorts, if necessary, based on toxicity, PK profiles, and PD findings.

All subjects will be required to start calcium, calcitriol, and vitamin D supplementation at least 3 days prior to Day 1 of each cycle and continue until ≥3 days after the last dose of Compound 1 in each cycle (eg, ≥Day 8 when Compound 1 is administered on Days 1-5).

Figure 1:
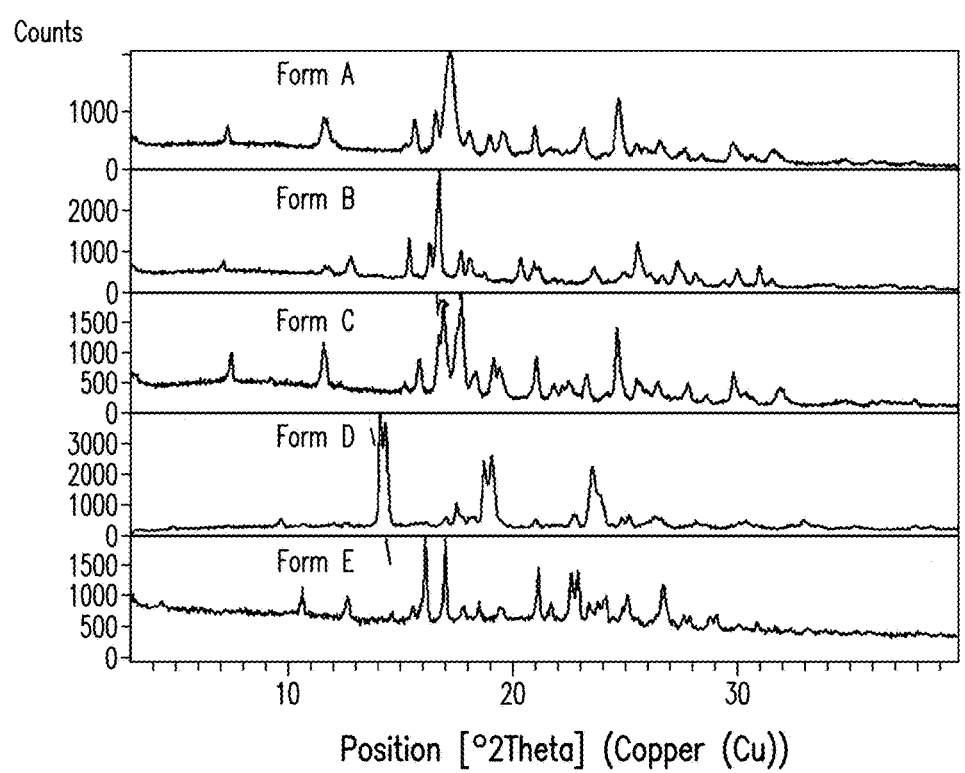
FIG. 1 depicts an X-ray powder diffractogram stack plot of Forms A, B, C, D, and E of Compound 1.

In Cycle 1, a bone marrow evaluation will be performed on Day 28 (±3 days). Based on the Day 28 bone marrow evaluation, subjects with hypoplastic bone marrow, without evidence of persistent leukemia, who have Grade ≥3 neutropenia will be followed for an additional 2 weeks for safety monitoring in Cycle 1 (total duration of 42 days; refer to FIG. 1). An additional bone marrow assessment will be performed at the time of hematologic recovery or Day 42 (±3 days). Thus, in Part A, the window for evaluation of dose-limiting toxicity (DLT) during Cycle 1 will be up to 42 days (28 or 42 days).

Cycles 2 through 4 will be 28 days in length.

Follow-Up Period

In the Follow-up Period, all subjects will be followed for 28 days (±3 days) after the last dose of Compound 1 for safety.

Subjects without documented progression of disease (or relapse) will have efficacy evaluations of complete blood counts and peripheral blood smears performed every subsequent 8 weeks (±1 week) for the 1st year and every 12 weeks (±2 weeks) for the 2nd year or until progression of disease (or relapse), initiation of a new anticancer therapy, withdrawal of consent from the study, death, or the End of Trial, whichever comes first. A bone marrow evaluation will be completed at the end of the 1 st year and as clinically indicated during the Follow-up Period.

All subjects will be followed for survival follow-up according to the schedule for the efficacy long term follow-up for up to 2 years or until death, lost to follow-up, or the End of Trial, whichever occurs first. Survival follow-up may be conducted by record review (including public records) and/or telephone contact with the subject, family, or the subject's treating physician.

Part A-Dose Escalation

During the escalation phase (Part A), a modified accelerated titration design (Simon et al., *J Natl Cancer Inst* 1997; 89(15): 1138-47) will be used to establish initial toxicity. Cohorts of one or more subjects each will be administered Compound 1 at doses that will increase in 100% increments per cohort until ≥2 subjects experience a Compound 1-related Grade ≥2 adverse event in the DLT window (may be different cohorts), or ≥1 subject experiences a DLT within the DLT window. At that time the current cohort and all subsequent cohorts will be expanded enrolling 3 to 6 subjects. A dose escalation schedule with dose increments not to exceed 50% will concurrently be initiated in order to establish the NTD and MTD. The initial dose will be 0.3 mg. Sample dose escalation schemes are shown in FIG. 2. The N,N-dimethylacetamide (DMA) residual solvent in Compound 1 formulation must not exceed the permitted daily exposure (PDE) limits set in the ICH Q3C Impurities: Residual Solvents in order to proceed with dose escalation cohorts above a daily Compound 1 dose of 2.4 mg.

Dose escalation decisions will be made at the discretion of a Safety Review Committee (SRC) that will include Investigators (and/or designated representatives), the Sponsor's study physician, safety physician, and the study manager. Ad hoc attendees may include the study pharmacokineticist, study statistician, and additional study clinical scientists. Other internal and external experts may be consulted by the SRC, as necessary.

The SRC may decide to evaluate a higher dose cohort, additional subjects within a dose cohort, intermediate dose cohorts, smaller dose increments, alternate dosing schedules (eg, increasing from 5 to up to 10 days of Compound 1 administration), and/or declare an MTD based on their review of available clinical and laboratory safety data, PK profiles, and PD findings. In the event that an alternate dosing schedule is evaluated, the starting dose and schedule will not exceed the dose intensity of a dose cohort that has previously met the criteria for dose escalation After the first dose is administered in any cohort during dose escalation, subjects in each cohort are observed for at least 28 days and up to 42 days (Cycle 1, DLT window) before the next higher, dose cohort can begin. No more than one subject per day will be enrolled in a given dose escalation cohort. A subject evaluable for DLT is defined as one that:

Has received at least 80% of the total planned Cycle 1 dose (eg, 4 complete Compound 1 doses for a 5-day dose schedule; in case of a missed dose, ≥4 doses to be completed on or before Day 7) of Compound 1 during Cycle 1 without experiencing a DLT, or Experienced a DLT after receiving at least one dose (or fraction thereof) of Compound 1.

In the event that an alternate dose schedule (eg, increasing from 5 days to up to 10 days of dosing) is evaluated in Part A, the same criteria for determining DLT-evaluable subjects will be applied. Subjects non evaluable for DLT will be replaced.

A dose will be considered intolerable if >33% of evaluable subjects in a dose cohort experience DLT during Cycle 1. The MTD will be defined as the last dose below the NTD, at which ≤33% of evaluable subjects experienced DLT during Cycle 1. If 2 or more of 6 evaluable subjects experience DLTs in the first dose cohort, a lower dose cohort may be explored at the discretion of the SRC (ie, 0.1 mg Compound 1). An intermediate dose of Compound 1 (one between the NTD and the last dose level before the NTD) may be evaluated to accurately determine the MTD.

Intra-subject dose escalation will not be allowed during the DLT assessment period; however, in Cycles ≥2, subjects without evidence of disease progression who are tolerating their assigned dose of Compound 1 may (at the Investigator's discretion) escalate to the highest dose level shown to be adequately tolerated by at least one cohort of subjects in this study (ie, ≤33% of evaluable subjects having experienced a DLT at that dose level).

Part B-Cohort Expansion

Following completion of dose escalation (Part A), additional subjects may be enrolled into an expansion phase (Part B) with up to approximately 20 evaluable subjects in each cohort. Expansion may occur at the MTD and schedule established in the dose escalation phase, and/or at an alternative tolerable dose and schedule, based on review of safety, PK, and PD data from Part A. The SRC will select the doses and schedules of interest for cohort expansion. One or more dosing regimens may be selected for cohort expansion. The SRC will continue to review safety data regularly throughout the study and make recommendations about study continuation and dose modification, as appropriate.

Study Population

Men and women, 18 years or older, with relapsed or refractory AML as defined by World Health Organization criteria (Lowenberg, Acute myeloid leukemia: the challenge of capturing disease variety. *Hematology ASH Education Program* 2008; 2008(1): 1-11) who are not suitable for other established therapies, will be enrolled in the study.

Length of Study

Enrollment is expected to take approximately 18 to 24 months to complete (12 to 15 months for dose escalation, and 6 to 9 months for expansion). Completion of active treatment and post treatment follow-up is expected to take an additional 6 to 24 months. The entire study is expected to last up to approximately 3 to 4 years.

The End of Trial is defined as either the date of the last visit of the last subject to complete the post-treatment follow-up, or the date of receipt of the last data point from the last subject that is required for primary, secondary and/or exploratory analysis, as prespecified in the protocol, whichever is the later date.

Study Treatments

Compound 1 for IV injection, labeled appropriately for investigational use will be supplied as per the regulations of the relevant country health authority. Study drug will be administered as outlined in the Treatment Period section above.

Study treatment may be discontinued if there is evidence of clinically significant disease progression (or relapse), unacceptable toxicity or subject/physician decision to withdraw. Subjects may continue to receive study drugs beyond disease progression at the discretion of the Investigator.

Overview of Key Efficacy Assessments

The primary efficacy variable is leukemia response rate. All treated subjects will be included in the efficacy analyses. Leukemia response will be determined by the Investigator. Assessment will be based on the International Working Group Response Criteria in AML (Cheson, *J Clin Oncol* 2003; 21(24):4642-9).

A descriptive analysis of evidence of antileukemic activity will be provided based on clinical, laboratory, molecular, and cytogenetic assessments by Investigator, which includes assessment of bone marrow blast percentage, bone marrow cytogenetics, molecular genetic studies to evaluate molecular responses, bone marrow flow cytometry, platelet count, and absolute neutrophil count.

Response criteria will be summarized by best overall response categories: complete remission rate (CRR), and objective response rate (ORR). The ORR includes all responses of complete remission (CR) (ie, morphologic leukemia-free state, morphologic CR, cytogenetic CR, molecular CR, and morphologic CR with incomplete blood recovery), and partial remission.

The efficacy variable of focus will be ORR and CRR. Other measures of clinical activity including overall survival (OS), relapse free survival (RFS), progression-free survival (PFS), event-free survival, duration of remission, duration of response, and time to remission/response will be summarized.

Overview of Key Safety Assessments

The safety variables for this study include adverse events, safety clinical laboratory variables, 12-lead electrocardiograms, Eastern Cooperative Oncology Group Performance Status, left ventricular ejection fraction assessments, physical examinations, vital signs, exposure to study treatment, assessment of concomitant medications, and pregnancy testing for females of childbearing potential.

Overview of Key Pharmacokinetic Assessments

The plasma PK parameters determined for Compound 1 will be maximum observed plasma concentration (Cmax), area under the plasma concentration-time curve from time 0 to 24 hours postdose (AUC24), terminal-phase elimination half-life (t1/2), total plasma clearance (CL), time to perak (maximum) plasma concentration (tmax), volume of distribution at the steady state (Vss). Selected PK parameters (eg, Cmax, AUC24, t1/2) will be estimated for R- and S-enantiomers of Compound 1 as appropriate.

Statistical Methods

Statistical analyses will be performed by dose level (Part A) and cohort (Part B) as needed or applicable. All analyses will be descriptive in nature.

All summaries of safety data will be conducted using subjects receiving any Compound 1 (the Treated Population).

The efficacy variables of primary interest are the ORR and CRR. Other preliminary efficacy variables including OS, RFS, PFS, event-free survival, duration of remission, duration of response, and time to remission/response will be summarized. Efficacy analysis will be repeated for the Treated Population and Efficacy Evaluable Population (received a baseline leukemia assessment evaluation, at least one cycle of study treatment or at least 80% of scheduled doses in Cycle 1, and one on study leukemia assessment evaluation), with the result using the Treated Population considered primary.

All biomarker-related data presentations will be based on treated subjects with at least one biomarker assessment, unless specified otherwise. Descriptive statistics will be presented for baseline and change from baseline of continuous biomarker endpoints, by dosing regimens and/or disease subsets, and overall.

Exploration of PK, PD, safety and activity relationships will be assessed.

The study will be conducted in compliance with International Conference on Harmonisation of Technical Requirements for Registration of Pharmaceuticals for Human Use/Good Clinical Practice and applicable regulatory requirements.

Inclusion Criteria

Subjects must satisfy the criteria below to be enrolled in dose escalation (Part A) or dose expansion (Part B) of this study.

1. Men and women ≥18 years of age, at the time of signing the ICD.

2. Subject must understand and voluntarily sign an ICD prior to any study-related assessments/procedures being conducted.

3. Subject is willing and able to adhere to the study visit schedule and other protocol requirements.

4. Relapsed or refractory AML as defined by World Health Organization criteria (Lowenberg, *Hematology ASH Education Program* 2008; (1): 1-11) who are not suitable for other established therapies.

5. Eastern Cooperative Oncology Group Performance Status (ECOG PS) of 0 to 2.

6. At least 4 weeks (from first dose) has elapsed from donor lymphocyte infusion (DLI) without conditioning.

7. Subjects must have the following screening laboratory values:

Corrected serum Ca or free (ionized) serum Ca within normal limits (WNL).

Corrected Ca (mg/dL)=Total Ca (mg/dL)−0.8 (albumin [g/dL]−4)

Total White Blood Cell count (WBC)<25×10$^9$/L prior to first infusion. Prior or concurrent treatment with hydroxyurea to achieve this level is allowed.

Potassium and magnesium within normal limits or correctable with supplements.

Aspartate aminotransferase/serum glutamic oxaloacetic transaminase (AST/SGOT) or alanine aminotransferase/serum glutamate pyruvic transaminase (ALT/SGPT)≤2.5× Upper Limit of Normal (ULN).

Uric acid ≤7.5 mg/dL (446 µmol/L). Prior and/or concurrent treatment with hypouricemic agents (eg, allopurinol, rasburicase) are allowed.

Serum bilirubin ≤1.5×ULN.

Estimated serum creatinine clearance of ≥60 mL/min using the Cockcroft-Gault equation.

INR <1.5×ULN and PTT <1.5×ULN.

8. Per Compound 1 Pregnancy Prevention Plan (PPP):

a). Females of childbearing potential (FCBP) must undergo pregnancy testing based on the frequency outlined in PPP and pregnancy results must be negative.

b). Unless practicing complete abstinence from heterosexual intercourse, sexually active FCBP must agree to use adequate contraceptive methods as specified in PPP.

FCBP must agree to use two reliable forms of contraception simultaneously (or to practice complete abstinence), without interruption, for 28 days before starting Compound 1, throughout the entire duration of Compound 1 treatment, during dose interruptions and for at least 28 days after the last dose of Compound 1.

Complete abstinence is only acceptable in cases where this is the preferred and usual lifestyle of the subject.

Periodic abstinence (calendar ovulation, symptothermal, post-ovulation methods) and withdrawal are not acceptable.

c). Unless practicing complete abstinence from heterosexual intercourse, sexually active males (including those who have had a vasectomy) must use barrier contraception (condoms) when engaging in sexual activity with FCBP as specified in PPP.

Complete abstinence is only acceptable in cases where this is the preferred and usual lifestyle of the subject.

d). Females must agree to abstain from breastfeeding or providing breast milk for the duration specified in the PPP.

e). Males must agree not to donate semen or sperm for the duration specified in the PPP.

f). All subjects must:

Understand that Compound 1 could have a potential teratogenic risk.

Agree to abstain from donating blood for the duration specified in the PPP.

Be counseled about pregnancy precautions and risks of fetal exposure.

Exclusion Criteria

The presence of any of the following will exclude a subject from enrollment:

1. Subjects with acute promyelocytic leukemia (APL)
2. Subjects with clinical symptoms suggesting active central nervous system (CNS) leukemia or known CNS leukemia. Evaluation of cerebrospinal fluid is only required if there is clinical suspicion of CNS involvement by leukemia during screening.
3. Subjects with immediately life-threatening, severe complications of leukemia such as disseminated/uncontrolled infection, uncontrolled bleeding, and/or uncontrolled disseminated intravascular coagulation.
4. Disorders or conditions disrupting normal calcium homeostasis or preventing calcium supplementation including:

Any known condition disrupting calcium absorption.

Clinical evidence of hypo- or hyperparathyroidism.

Bisphosphonate or denosumab therapy within last 4 weeks prior to starting Compound 1.

Active or recent kidney stones (≤1 year prior to starting Compound 1).

Serum 25-hydroxyvitamin D level <12 ng/mL (30 nmol/L).

5. Impaired cardiac function or clinically significant cardiac diseases, including any of the following:

Left ventricular ejection fraction (LVEF)<45% as determined by multiple gated acquisition (MUGA) scan or echocardiogram (ECHO).

Complete left bundle branch or bifascicular block.

Congenital long QT syndrome.

Persistent or clinically meaningful ventricular arrhythmias.

QTcF ≥470 msec on Screening electrocardiogram (ECG) (mean of triplicate recordings performed ≥72 hours prior to Day 1).

Unstable angina pectoris or myocardial infarction ≤3 months prior to starting Compound 1.

6. Patients with prior autologous hematopoietic stem cell transplant who, in the investigator's judgment, have not fully recovered from the effects of the last transplant (eg, transplant related side effects).
7. Prior allogeneic hematopoietic stem cell transplant (HSCT) with either standard or reduced intensity conditioning ≤6 months prior to starting Compound 1.
8. Subjects on systemic immunosuppressive therapy post HSCT at the time of screening, or with clinically significant graft-versus-host disease (GVHD). The use of topical steroids for ongoing skin or ocular GVHD is permitted.
9. Prior systemic cancer-directed treatments or investigational modalities ≤5 half lives or 4 weeks prior to starting Compound 1, whichever is shorter. Hydroxyurea is allowed to control peripheral leukemia blasts.
10. Leukapheresis ≤2 weeks prior to starting Compound 1.
11. Major surgery ≤2 weeks prior to starting Compound 1. Subjects must have recovered from any clinically significant effects of recent surgery.
12. Pregnant or nursing females.
13. Known human immunodeficiency virus (HIV) infection.
14. Known chronic, active hepatitis B or C (HBV/HCV) infection.
15. Ongoing treatment with chronic, therapeutic dosing of anti-coagulants (eg, warfarin, low molecular weight heparin, Factor Xa inhibitors).
16. History of concurrent second cancers requiring active, ongoing systemic treatment.
17. Subject has a known allergy/hypersensitivity to calcium, calcitriol, and/or vitamin D supplements or any of their ingredients.
18. Subject has any significant medical condition, laboratory abnormality, or psychiatric illness that would prevent the subject from participating in the study.
19. Subject has any condition including the presence of laboratory abnormalities, which places the subject at unacceptable risk if he/she were to participate in the study.
20. Subject has any condition that confounds the ability to interpret data from the study.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed:

1. A method for treating, managing, or ameliorating a hematological cancer comprising administering to a subject in need thereof 2-(4-chlorophenyl)-N-((2-(2,6-dioxopiperidin-3-yl)-1-oxoisoindolin-5-yl)methyl)-2,2-difluoroacetamide, which has the following structure:

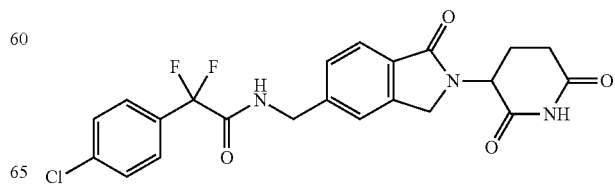

or a stereoisomer or mixture of stereoisomers, isotopologue, pharmaceutically acceptable salt, tautomer, solvate, hydrate, co-crystal, clathrate, or polymorph thereof (Compound 1), wherein Compound 1 is administered to the subject in a dose of about 0.1 mg to about 20 mg, and the subject is further administered one or more of calcium, calcitriol, or vitamin D supplementation.

2. The method of claim 1, wherein the hematological cancer is acute myeloid leukemia.

3. The method of claim 2, wherein the acute myeloid leukemia is refractory or relapsed acute myeloid leukemia.

4. The method of claim 1, wherein Compound 1 is administered on days 1 to 5 of a 28 day treatment cycle.

5. The method of claim 4, wherein the treatment cycle comprises a rest period of 23 days.

6. The method of claim 1, wherein Compound 1 is administered on days 1 to 5 of a 42 day treatment cycle.

7. The method of claim 1, wherein Compound 1 is administered on days 1 to 3 of a 28 day treatment cycle.

8. The method of claim 1, wherein Compound 1 is administered on days 1 to 5 and days 15 to 19 of a 28 day treatment cycle.

9. The method of claim 4, wherein the treatment cycle is repeated at least once.

10. The method of claim 4, wherein the treatment cycle is repeated 2 to 4 times.

11. The method of claim 1, wherein Compound 1 is administered in a dose of about 0.1 mg to about 10 mg.

12. The method of claim 1, wherein Compound 1 is administered in a dose from about 0.3 mg to about 8.1 mg.

13. The method of claim 1, wherein Compound 1 is administered in a dose of about 0.3 mg, 0.6 mg, 1.2 mg, 2.4 mg, 3.6 mg, 5.4 mg or 8.1 mg.

14. The method of claim 1, wherein Compound 1 is administered in a dose of about 0.6 mg, 1.2 mg, 1.8 mg, 2.4 mg, or 3.6 mg.

15. The method of claim 1, wherein the subject is administered one or more of calcium, calcitriol, or vitamin D supplementation prior to administration of Compound 1.

16. The method of claim 1, wherein the subject is administered one or more of calcium, calcitriol, or vitamin D supplementation at least 3 days prior to administration of Compound 1 on day 1 of the cycle.

17. The method of claim 1, wherein the subject does not have a disorder disrupting normal calcium homeostasis or preventing calcium supplementation.

18. The method of claim 1 comprising administering a polymorph of (2-(4-chlorophenyl)-N-((2-(2,6-dioxopiperidin-3-yl)-1-oxoisoindolin-5-yl)methyl)-2,2-difluoroacetamide).

19. The method of claim 1 comprising administering an amorphous form of (2-(4-chlorophenyl)-N-((2-(2,6-dioxopiperidin-3-yl)-1-oxoisoindolin-5-yl)methyl)-2,2-difluoroacetamide).

20. The method of claim 1 comprising administering a lyophilized formulation of Compound 1, wherein the lyophilized formulation comprises Compound 1, a buffer and a bulking agent.

21. The method of claim 1, further comprising administering a therapeutically effective amount of a second active agent or a supportive care therapy.

22. The method of claim 1, wherein the subject is a patient 18 years or older.

23. The method of claim 1, wherein the hematological cancer is myelodysplastic syndrome.

24. The method of claim 23, wherein the myelodysplastic syndrome is refractory or relapsed myelodysplastic syndrome.

25. The method of claim 23, wherein Compound 1 is administered on days 1 to 5 of a 28 day treatment cycle.

26. The method of claim 23, wherein Compound 1 is administered on days 1 to 5 of a 42 day treatment cycle.

27. The method of claim 23, wherein Compound 1 is administered on days 1 to 3 of a 28 day treatment cycle.

28. The method of claim 23, wherein Compound 1 is administered on days 1 to 5 and days 15 to 19 of a 28 day treatment cycle.

29. The method of claim 25, wherein the treatment cycle is repeated at least once.

30. The method of claim 25, wherein the treatment cycle is repeated 2 to 4 times.

31. The method of claim 23, wherein Compound 1 is administered in a dose of about 0.1 mg to about 10 mg.

32. The method of claim 23, wherein Compound 1 is administered in a dose from about 0.3 mg to about 8.1 mg.

33. The method of claim 23, wherein Compound 1 is administered in a dose of about 0.3 mg, 0.6 mg, 1.2 mg, 2.4 mg, 3.6 mg, 5.4 mg or 8.1 mg.

34. The method of claim 23, wherein Compound 1 is administered in a dose of about 0.6 mg, 1.2 mg, 1.8 mg, 2.4 mg, or 3.6 mg.

35. The method of claim 23, wherein the subject is administered one or more of calcium, calcitriol, or vitamin D supplementation.

36. The method of claim 35, wherein the subject is administered one or more of calcium, calcitriol, or vitamin D supplementation prior to administration of Compound 1.

37. The method of claim 35, wherein the subject is administered one or more of calcium, calcitriol, or vitamin D supplementation at least 3 days prior to administration of Compound 1 on day 1 of the cycle.

38. The method of claim 23, wherein the subject does not have a disorder disrupting normal calcium homeostasis or preventing calcium supplementation.

39. The method of claim 23 comprising administering a polymorph of (2-(4-chlorophenyl)-N-((2-(2,6-dioxopiperidin-3-yl)-1-oxoisoindolin-5-yl)methyl)-2,2-difluoroacetamide).

40. The method of claim 23 comprising administering an amorphous form of (2-(4-chlorophenyl)-N-((2-(2,6-dioxopiperidin-3-yl)-1-oxoisoindolin-5-yl)methyl)-2,2-difluoroacetamide).

41. The method of claim 23 comprising administering a lyophilized formulation of Compound 1, wherein the lyophilized formulation comprises Compound 1, a buffer and a bulking agent.

42. The method of claim 23, further comprising administering a therapeutically effective amount of a second active agent or a supportive care therapy.

43. The method of claim 23, wherein the subject is a patient 18 years or older.

* * * * *